(12) United States Patent
Kanner et al.

(10) Patent No.: US 7,192,731 B2
(45) Date of Patent: Mar. 20, 2007

(54) METHODS FOR EFFICIENT EXTRACTION OF CAROTENOIDS USING AN ESTERASE

(75) Inventors: Joseph Kanner, Rehovot (IL); Rina Granit, Rehovot (IL); Arieh Levy, Rehovot (IL)

(73) Assignee: The State of Israel, Ministry of Agriculture & Rural Development, Agricultural Research Organization, (A.R.O.), Volcani Center, Beit-Dagan (IL)

(*) Notice: Subject to any disclaimer, the term of this patent is extended or adjusted under 35 U.S.C. 154(b) by 220 days.

(21) Appl. No.: 10/661,606

(22) Filed: Sep. 15, 2003

(65) Prior Publication Data

US 2004/0166199 A1 Aug. 26, 2004

Related U.S. Application Data

(63) Continuation-in-part of application No. PCT/IL02/00398, filed on May 21, 2002, which is a continuation of application No. 09/915,527, filed on Jul. 27, 2001, now abandoned.

(60) Provisional application No. 60/292,953, filed on May 24, 2001.

(51) Int. Cl.
*C12Q 1/44* (2006.01)
(52) U.S. Cl. .................. 435/19; 435/67; 424/760; 585/351
(58) Field of Classification Search ............ 435/19, 435/67; 424/760; 585/351
See application file for complete search history.

(56) References Cited

U.S. PATENT DOCUMENTS

| | | | |
|---|---|---|---|
| 4,844,934 A * | 7/1989 | Lueddecke et al. ......... 426/540 |
| 5,789,647 A | 8/1998 | Heidlas et al. |
| 5,916,791 A | 6/1999 | Hirschberg et al. |
| 5,935,808 A | 8/1999 | Hirschberg et al. |
| 6,200,597 B1 * | 3/2001 | Mehta et al. ............... 424/450 |
| 6,218,599 B1 | 4/2001 | Hirschberg et al. |
| 6,350,890 B1 * | 2/2002 | Kiy et al. .................. 554/167 |
| 6,428,816 B1 | 8/2002 | Schlipalius et al. |
| 2003/0017239 A1 * | 1/2003 | Bodor et al. ............... 426/250 |
| 2003/0054070 A1 * | 3/2003 | Bridges et al. .............. 426/73 |
| 2004/0147005 A1 * | 7/2004 | Zorn et al. ................. 435/198 |
| 2004/0166199 A1 | 8/2004 | Kanner et al. |

FOREIGN PATENT DOCUMENTS

| | | |
|---|---|---|
| FR | 2818992 | 5/2002 |
| JP | 51-142020 | 6/1976 |
| JP | 59-091155 | 5/1984 |
| JP | 62-115067 | 5/1987 |
| SU | 1568310 | 4/1995 |
| WO | WO 02/094982 | 11/2002 |
| WO | WO 2005/017142 | 2/2005 |
| WO | WO 2005/026739 | 3/2005 |

OTHER PUBLICATIONS

Kanner J. et al. Carotenoids Extraction From Orange Peel by Treatments With Enzymes and d-Limonene. Int Frucht Saft Union (Berlin) 1984 vol. 18, pp. 219-225.*
Breithaupt D. et al. Enzymatic Hydrolysis of Carotenoid Fatty Acid Esters of Red Pepper by a Lipase from *Candida rugosa*. Z Naturforsch 55(11-12)971-975.*
Fernandez X. et al. Effect of Alkali Saponification, Enzymatic Hydrolysis and Storage Time on the Total Carotenoid Concentration of Costa Rican Crude Palm Oil. J of Food Composition and Analysis 2000 13(2)179-187.*
Khachik F et al. Identification, Quantification, and Relative concentrations of Carotenoids and Their Metabolites in Human Milk and Serum. Anal Chem 1997 vol. 69, pp. 1873-1881.*
Aakermann et al. "Enzymatic Hydrolysis of Esters of Alkali Labile Carotenols", Biocatalysis and Biotransformation, 13: 157-163, 1996.
Breithaupt et al. "Carotenol Fatty Acid Esters: Easy Substrates for Digestive Enzymes?", Comparative Biochemistry and Physiology, Part B, 132: 721-728, 2002.
Zorn et al. "Enzymatic Hydrolysis of Carotenoid Esters of Marigold Flowers (*Tagetes erecta* L.) and Red Paprika (*Capsicum Annuum* L.) by Commercial Lipases and Pleurotus Sapidus Extracellular Lipase", Enzyme and Microbial Technology, 32: 623-628, 2003. Abstract, p. 624, § Joining l-h & r-h col., § Joining p. 625, 626.
Liu et al. "Enzymatic Hydrolysis, Extraction, and Quantitation of Retinol and Major Carotenoids in Mature Human Milk", Journal of Nutritional Biochemisty, 9(3): 178-183, 1998. Abstract, Fig. 1, § Joining p. 180, 181.
Santamaria et al. "Selective Enzyme-Mediated Extraction of Capsaicinoids and Carotenoids From Chili Guajillo Puya (*Capsicum annuum* L.) Using Ethanol as Solvent", Journal of Agricultural and Food Chemistry, 48(7): 3063-3067, 2000. Abstract, § Joining l-h &r-h cols. on p. 3064.

(Continued)

*Primary Examiner*—Ralph Gitomer

(57) ABSTRACT

A method of increasing a fraction of free carotenoids in a source of carotenoids in which at least some of the carotenoids are fatty acid esterified carotenoids is disclosed. The method is effected by contacting the source of carotenoids with an effective amount of an esterase under conditions effective in deesterifying the fatty acid esterified carotenoids, thereby increasing the fraction of free carotenoids in the source of carotenoids.

26 Claims, 17 Drawing Sheets

OTHER PUBLICATIONS

Breithaupt "Enzymatic Hydrolysis of Carotenoid Fatty Acid Esters of Red Pepper (*Capsicum annuum* L.) by a Lipase From *Candida rugosa*", Verl. d. Zeitschrift f. Naturforschung, 55(11-12): 971-975, 2000.

Perez-Galvez et al. "Incorporation of Carotenoids From Paprika Oleoresin Into Human Chylomicrons", Br. J. Nutr., 89(6): 787-793, 2003. Abstract.

Kanner et al. "Carotenoids Extraction From Orange Peel by Treatment With Enzymes and D-Limonene", Int. Fruchtsaft Union, 18: 219-225, 1984.

Lauridsen et al. "Hydrolysis of Tocopheryl and Retinyl Esters by Porcine Carboxyl Ester Hydrolase Is Affected by Their Carboxylate Moiety and Bile Acids", Journal of Nutritional Biochemistry, 12: 219-224, 2001.

Lindstrom et al. "Concerted Action of Human Carboxyl Ester Lipase and Pancreatic Lipase During Lipid Digestion In Vitro: Importance of the Physicochemical State of the Substrate", Biochim. Biophys. Acta, 959(2): 178-184, 1988. Abstract.

Breithaupt et al. "Carotenoid Esters in Vegetables and Fruits: A Screening With Emphasis on β-Cryptoxanthin Esters", J. Agric. Food Chem., 49: 2064-2070, 2001.

Orlich et al. "*Candida rugosa* Lipase Reactions in Nonionic W/O-Microemulsion With A Technical Surfactant", Enzyme and Microbial Technology, 28: 42-48, 2001. Abstract.

Martin et al. "Yellow Pigments of Dioscorea Bulbifera", Journal of Agriculture and Food Chemistry, 22(2): 335-337, 1974. Abstract, p. 335, r-h col., 1st §, p. 337, r-h col., 3rd §.

Salo-Väänänen et al. "Simultaneous HPLC Analysis of Fat-Soluble Vitamins in Selected Animal Products After Small-Scale Extraction", Food Chemistry, 71(4): 535-543, 2000. Abstract, p. 535, l-h col., Lines 1-4, p. 536, l-h col., last §, p. 537, r-h col., 2nd §, p. 538, l-h col., Lines 8-10, Fig. 2.

* cited by examiner

DAYS STORAGE

| Emulsion | 0 days | 10 days | 20 days | 30 days |
|---|---|---|---|---|
| Deesterified oleoresin 0.15% Tween | 1.402 | 1.377 | 1.317 | 1.216 |
| Deesterified oleoresin 0.03% Tween | 1.352 | 1.326 | 1.206 | 1.147 |
| Untreated oleoresin 0.15%Tween | 1.220 | 1.159 | 1.17 | 1.061 |
| Untreated oleoresin 0.03% Tween | 0.912 | 0.662 | 0.618 | 0.621 |

Note: Values in OD at 474 nm

Figure 12

Figure 14a  Extraction of deesterified oleoresin with and without alkaline conditions: Carotenoids, %composition.

| CAROTENOID | pH adjusted | Without pH adjustment |
|---|---|---|
| Capsorubin | 1.22±0.23% | 1.08±0.20% |
| Violaxathin | 2.36±0.21% | 2.13±0.30% |
| Capsanthin | 42.20±1.30% | 38.73±1.10% |
| Zeaxanthin+ capsolutein | 19.33±0.74% | 17.62±0.80% |
| β cryptoxanthin | 5.94±0.33% | 6.38±0.40% |
| β carotene | 7.97±0.20% | 8.50±0.32% |
| Other Carotenoids | 20.98±3.01% | 25.56±3.12% |

Figure 14b  Extraction of deesterified oleoresin with and without alkaline conditions: mg/gram deesterified extract.

| Carotenoid | pH adjusted | Without pH adjustment |
|---|---|---|
| Capsorubin | 2.56±0.48 | 0.81±0.15 |
| Violaxanthin | 4.95±0.44 | 1.59±0.22 |
| Capsanthin | 88.6±2.73 | 29.00±0.825 |
| Zeaxanthin+ capsolutein | 40.59±1.55 | 13.20±0.60 |
| β cryptoxanthin | 12.47±0.69 | 4.78±0.30 |
| β carotene | 16.73±0.42 | 6.37±0.31 |
| Other Carotenoids | 44.00±6.30 | 19.17±2.34 |
| Total carotenoids | 209.9±12.61 | 74.92±4.74 |
| Enrichment (deesterified/untreated) | 2.84 fold (209.9/74 mg/g) | 1.01 fold (74.9/74 mg/g) |
| Vitamin E | 20.30 | 5.00 |
| Enrichment (deesterified/untreated) | 3.7 fold (20.3/5.5 mg/g) | 0.9 fold (5.0/5.5 mg/g) |

Figure 17 Enzymatically deesterified carotenoids: %composition (wt/wt):

| Component | Without Vitamin E depletion | Vitamin E depletion by Florisil column |
|---|---|---|
| Capsorubin | 1.22±0.23% | 1.68±0.20% |
| Violaxanthin | 2.36±0.21% | 2.70±0.30% |
| Capsanthin | 42.20±1.30% | 46.00±2.10% |
| Zeaxanthin+ capsolutein | 19.33±0.74% | 19.70±0.80% |
| $\beta$ cryptoxanthin | 5.94±0.33% | 5.50±0.40% |
| $\beta$ carotene | 7.97±0.20% | 3.89±0.33% |
| Other Carotenoids | 20.98±3.01% | 20.53±4.13% |
| Total carotenoids | 210.00±10.30mg/g | 204.00±6.30mg/g |
| Vitamin E | 20.30 mg/g | 0.50mg/g |

US 7,192,731 B2

METHODS FOR EFFICIENT EXTRACTION OF CAROTENOIDS USING AN ESTERASE

This is a Continuation-in-Part of PCT/IL02/00398, filed May 21, 2002, which claims priority from U.S. patent application Ser. No. 09/915,527, filed Jul. 27, 2001, now abandoned and U.S. Provisional Patent Application No. 60/292,953, filed May 24, 2001, now expired.

FIELD AND BACKGROUND OF THE INVENTION

The present invention relates to a novel method of increasing the bioavailability of carotenoids. More particularly, the present invention relates to methods of extracting oleoresin, increasing the content of free carotenoids in sources of carotenoids rich in fatty acid esterified carotenoids, red pepper in particular. The present invention further relates to the extraction of free carotenoids from the sources of carotenoids rich in fatty acid esterified carotenoids and to food and feed additives that comprise free carotenoids.

Carotenoids, Chemistry and Biochemistry:

The carotenoids are isoprenoid compounds, with an extensive conjugated double bond system, and are biosynthesized from acetyl coenzyme-A via mevalonic acid as a branch of the great isoprenoid or terpenoid pathway (Britton, 1996). They are divided into two main classes; carotenes [acyclic (lycopene) and cyclic (β-carotene)], and xanthophylls (e.g., capsanthin). In contrast to carotenes, which are pure polyene hydrocarbons, xanthophylls also contain hydroxy, epoxy and keto groups. Only plants, and microorganisms synthesize carotenoids, however they are reach by feed and food animal or human tissues, which have the ability to absorb, modify and store these compounds (Goodwin; 1980).

Of the over 640 carotenoids found in nature, about 20 are present in a typical human diet. Of these carotenoids, only 14 and some of their metabolites have been identified in blood and tissues (Gerster, 1997; Khackick et al., 1995; Oshima, et al., 1997).

As part of the light-harvesting antenna, carotenoids can absorb photons and transfer the energy to chlorophyll, thus assisting in the harvesting of light in the range of 450–570 nm [see, Cogdell R J and Frank H A (1987) How carotenoids function in photosynthetic bacteria. Biochim Biophys Acta 895: 63–79; Cogdell R (1988) The function of pigments in chloroplasts. In: Goodwin T W (ed) Plant Pigments, pp 183–255. Academic Press, London; Frank H A, Violette C A, Trautman J K, Shreve A P, Owens T G and Albrecht A C (1991) Carotenoids in photosynthesis: structure and photochemistry. Pure Appl Chem 63: 109–114; Frank H A, Farhoosh R, Decoster B and Christensen R L (1992) Molecular features that control the efficiency of carotenoid-to-chlorophyll energy transfer in photosynthesis. In: Murata N (ed) Research in Photosynthesis, Vol I, pp 125–128. Kluwer, Dordrecht; and, Cogdell R J and Gardiner A T (1993) Functions of carotenoids in photosynthesis. Meth Enzymol 214:185–193]. Although carotenoids are integral constituents of the protein-pigment complexes of the light-harvesting antennae in photosynthetic organisms, they are also important components of the photosynthetic reaction centers.

Most of the total carotenoids is located in the light harvesting complex II [Bassi R, Pineaw B, Dainese P and Marquartt J (1993) Carotenoid binding proteins of photosystem II. Eur J Biochem 212: 297–302]. The identities of the photosynthetically active carotenoproteins and their precise location in light-harvesting systems are not known. Carotenoids in photochemically active chlorophyll-protein complexes of the thermophilic cyanobacterium *Synechococcus* sp. were investigated by linear dichroism spectroscopy of oriented samples [see, Breton J and Kato S (1987) Orientation of the pigments in photosystem II: low-temperature linear-dichroism study of a core particle and of its chlorophyll-protein subunits isolated from *Synechococcus* sp. Biochim Biophys Acta 892: 99–107]. These complexes contained mainly a β-carotene pool absorbing around 505 and 470 nm, which is oriented close to the membrane plane. In photochemically inactive chlorophyll-protein complexes, the β-carotene absorbs around 495 and 465 nm, and the molecules are oriented perpendicular to the membrane plane.

Evidence that carotenoids are associated with cyanobacterial photosystem (PS) II has been described [see, Suzuki R and Fujita Y (1977) Carotenoid photobleaching induced by the action of photosynthetic reaction center II: DCMU sensitivity. Plant Cell Physiol 18: 625–631; and, Newman P J and Sherman L A (1978) Isolation and characterization of photosystem I and II membrane particles from the blue-green alga *Synechococcus cedrorum*. Biochim Biophys Acta 503: 343–361]. There are two β-carotene molecules in the reaction center core of PS II [see, Ohno T, Satoh K and Katoh S (1986) Chemical composition of purified oxygen-evolving complexes from the thermophilic cyanobacterium *Synechococcus* sp. Biochim Biophys Acta 852: 1–8; Gounaris K, Chapman D J and Barber J (1989) Isolation and characterization of a D1/D2/cytochrome b-559 complex from *Synechocystis* PCC6803. Biochim Biophys Acta 973: 296–301; and, Newell R W, van Amerongen H, Barber J and van Grondelle R (1993) Spectroscopic characterization of the reaction center of photosystem II using polarized light: Evidence for β-carotene excitors in PS II reaction centers. Biochim Biophys Acta 1057: 232–238] whose exact function(s) is still obscure [reviewed by Satoh K (1992) Structure and function of PS II reaction center. In: Murata N (ed) Research in Photosynthesis, Vol. 11, pp. 3–12. Kluwer, Dordrecht]. It was demonstrated that these two coupled β-carotene molecules protect chlorophyll P680 from photodamage in isolated PS II reaction centers [see, De Las Rivas J, Telfer A and Barber J (1993) 2-coupled β-carotene molecules protect P680 from photodamage in isolated PS II reaction centers. Biochim. Biophys. Acta 1142: 155–164], and this may be related to the protection against degradation of the D1 subunit of PS II [see, Sandmann G (1993) Genes and enzymes involved in the desaturation reactions from phytoene to lycopene. (abstract), 10th International Symposium on Carotenoids, Trondheim CL1–2]. The light-harvesting pigments of a highly purified, oxygen-evolving PS II complex of the thermophilic cyanobacterium *Synechococcus* sp. consists of 50 chlorophyll α and 7 β-carotene, but no xanthophyll, molecules [see, Ohno T, Satoh K and Katoh S (1986) Chemical composition of purified oxygen-evolving complexes from the thermophilic cyanobacterium *Synechococcus* sp. Biochim Biophys Acta 852: 1–8]. β-carotene was shown to play a role in the assembly of an active PS II in green algae [see, Humbeck K, Romer S and Senger H (1989) Evidence for the essential role of carotenoids in the assembly of an active PS II. Planta 179: 242–250].

Isolated complexes of PS I from *Phormidium luridum*, which contained 40 chlorophylls per P700, contained an average of 1.3 molecules of β-carotene [see, Thornber J P, Alberte R S, Hunter F A, Shiozawa J A and Kan K S (1976) The organization of chlorophyll in the plant photosynthetic unit. Brookhaven Symp Biology 28: 132–148]. In a preparation of PS I particles from *Synechococcus* sp. strain PCC 6301, which contained 130±5 molecules of antenna chlorophylls per P700, 16 molecules of carotenoids were detected [see, Lundell D J, Glazer A N, Melis A and Malkin R (1985) Characterization of a cyanobacterial photosystem I complex. J Biol Chem 260: 646–654]. A substantial content of β-carotene and the xanthophylls cryptoxanthin and isocryptoxanthin were detected in PS I pigment-protein complexes of the thermophilic cyanobacterium *Synechococcus elongatus* [see, Coufal J, Hladik J and Sofrova D (1989) The carotenoid content of photosystem 1 pigment-protein complexes of the cyanobacterium *Synechococcus elongatus*. Photosynthetica 23: 603–616]. A subunit protein-complex structure of PS I from the thermophilic cyanobacterium *Synechococcus* sp., which consisted of four polypeptides (of 62, 60, 14 and 10 kDa), contained approximately 10 β-carotene molecules per P700 [see, Takahashi Y, Hirota K and Katoh S (1985) Multiple forms of P700-chlorophyll α-protein complexes from *Synechococcus* sp.: the iron, quinone and carotenoid contents. Photosynth Res 6: 183–192]. This carotenoid is exclusively bound to the large polypeptides which carry the functional and antenna chlorophyll α. The fluorescence excitation spectrum of these complexes suggested that β-carotene serves as an efficient antenna for PS I.

As mentioned, an additional essential function of carotenoids is to protect against photooxidation processes in the photosynthetic apparatus that are caused by the excited triplet state of chlorophyll. Carotenoid molecules with π-electron conjugation of nine or more carbon-carbon double bonds can absorb triplet-state energy from chlorophyll and thus prevent the formation of harmful singlet-state oxygen radicals. In *Synechococcus* sp. the triplet state of carotenoids was monitored in closed PS II centers and its rise kinetics of approximately 25 nanoseconds is attributed to energy transfer from chlorophyll triplets in the antenna [see, Schlodder E and Brettel K (1988) Primary charge separation in closed photosystem II with a lifetime of 11 nanoseconds. Flash-absorption spectroscopy with oxygen-evolving photosystem II complexes from *Synechococcus*. Biochim Biophys Acta 933: 22–34]. It is conceivable that this process, that has a lower yield compared to the yield of radical-pair formation, plays a role in protecting chlorophyll from damage due to over-excitation.

The protective role of carotenoids in vivo has been elucidated through the use of bleaching herbicides such as norflurazon that inhibit carotenoid biosynthesis in all organisms performing oxygenic photosynthesis [reviewed by Sandmann G and Boger P (1989) Inhibition of carotenoid biosynthesis by herbicides. In: Boger P and Sandmann G (Eds.) Target Sites of Herbicide Action, pp 25–44. CRC Press, Boca Raton, Fla.]. Treatment with norflurazon in the light results in a decrease of both carotenoid and chlorophyll levels, while in the dark, chlorophyll levels are unaffected. Inhibition of photosynthetic efficiency in cells of *Oscillatoria agardhii* that were treated with the pyridinone herbicide, fluridone, was attributed to a decrease in the relative abundance of myxoxanthophyll, zeaxanthin and β-carotene, which in turn caused photooxidation of chlorophyll molecules [see, Canto de Loura I, Dubacq J P and Thomas J C (1987) The effects of nitrogen deficiency on pigments and lipids of cianobacteria. Plant Physiol 83: 838–843].

It has been demonstrated in plants that zeaxanthin is required to dissipate, in a nonradiative manner, the excess excitation energy of the antenna chlorophyll [see, Demmig-Adams B (1990) Carotenoids and photoprotection in plants: a role for the xanthophyll zeaxanthin. Biochim Biophys Acta 1020: 1–24; and, Demmig-Adams B and Adams W W III (1990) The carotenoid zeaxanthin and high-energy-state quenching of chlorophyll fluorescence. Photosynth Res 25: 187–197]. In algae and plants a light-induced deepoxidation of violaxanthin to yield zeaxanthin, is related to photoprotection processes [reviewed by Demmig-Adams B and Adams W W III (1992) Photoprotection and other responses of plants to high light stress. Ann Rev Plant Physiol Plant Mol Biol 43: 599–626]. The light-induced deepoxidation of violaxanthin and the reverse reaction that takes place in the dark, are known as the "xanthophyll cycle" [see, Demmig-Adams B and Adams W W III (1992) Photoprotection and other responses of plants to high light stress. Ann Rev Plant Physiol Plant Mol Biol 43: 599–626]. Cyanobacterial lichens, that do not contain any zeaxanthin and that probably are incapable of radiation energy dissipation, are sensitive to high light intensity; algal lichens that contain zeaxanthin are more resistant to high-light stress [see, Demmig-Adams B, Adams W W III, Green T G A, Czygan F C and Lange O L (1990) Differences in the susceptibility to light stress in two lichens forming a phycosymbiodeme, one partner possessing and one lacking the xanthophyll cycle. Oecologia 84: 451–456; Demmig-Adams B and Adams W W III (1993) The xanthophyll cycle, protein turnover, and the high light tolerance of sun-acclimated leaves. Plant Physiol 103: 1413–1420; and, Demmig-Adams B (1990) Carotenoids and photoprotection in plants: a role for the xanthophyll zeaxanthin. Biochim Biophys Acta 1020: 1–24]. In contrast to algae and plants, cyanobacteria do not have a xanthophyll cycle. However, they do contain ample quantities of zeaxanthin and other xanthophylls that can support photoprotection of chlorophyll.

Several other functions have been ascribed to carotenoids. The possibility that carotenoids protect against damaging species generated by near ultra-violet (UV) irradiation is suggested by results describing the accumulation of β-carotene in a UV-resistant mutant of the cyanobacterium *Gloeocapsa alpicola* [see, Buckley C E and Houghton J A (1976) A study of the effects of near UV radiation on the pigmentation of the blue-green alga *Gloeocapsa alpicola*. Arch Microbiol 107: 93–97]. This has been demonstrated more elegantly in *Escherichia coli* cells that produce carotenoids [see, Tuveson R W and Sandmann G (1993) Protection by cloned carotenoid genes expressed in *Escherichia coli* against phototoxic molecules activated by near-ultraviolet light. Meth Enzymol 214: 323–330]. Due to their ability to quench oxygen radical species, carotenoids are efficient anti-oxidants and thereby protect cells from oxidative damage. This function of carotenoids is important in virtually all organisms [see, Krinsky N I (1989) Antioxidant functions of carotenoids. Free Radical Biol Med 7: 617–635; and, Palozza P and Krinsky N I (1992) Antioxidant effects of carotenoids in vivo and in vitro—an overview. Meth Enzymol 213: 403–420]. Other cellular functions could be affected by carotenoids, even if indirectly.

In flowers and fruits carotenoids facilitate the attraction of pollinators and dispersal of seeds. This latter aspect is strongly associated with agriculture. The type and degree of pigmentation in fruits and flowers are among the most important traits of many crops. This is mainly since the colors of these products often determine their appeal to the consumers and thus can increase their market worth.

Carotenoids have important commercial uses as coloring agents in the food industry since they are non-toxic [see, Bauernfeind J C (1981) Carotenoids as colorants and vitamin A precursors. Academic Press, London]. The red color of the tomato fruit is provided by lycopene which accumulates during fruit ripening in chromoplasts. Tomato extracts, which contain high content (over 80% dry weight) of lycopene, are commercially produced worldwide for industrial use as food colorant. Furthermore, the flesh, feathers or eggs of fish and birds assume the color of the dietary carotenoid provided, and thus carotenoids are frequently used in dietary additives for poultry and in aquaculture. Certain cyanobacterial species, for example *Spirulina* sp. [see, Sommer T R, Potts W T and Morrissy N M (1990) Recent progress in processed microalgae in aquaculture. Hydrobiologia 204/205: 435–443], are cultivated in aquaculture for the production of animal and human food supplements. Consequently, the content of carotenoids, primarily of β-carotene, in these cyanobacteria has a major commercial implication in biotechnology.

Most carotenoids are composed of a $C_{40}$ hydrocarbon backbone, constructed from eight $C_5$ isoprenoid units and contain a series of conjugated double bonds. Carotenes do not contain oxygen atoms and are either linear or cyclized molecules containing one or two end rings. Xanthophylls are oxygenated derivatives of carotenes. Various glycosilated carotenoids and carotenoid esters have been identified. The $C_{40}$ backbone can be further extended to give $C_{45}$ or $C_{50}$ carotenoids, or shortened yielding apocarotenoids. Some nonphotosynthetic bacteria also synthesize $C_{30}$ carotenoids. General background on carotenoids can be found in Goodwin T W (1980) The Biochemistry of the Carotenoids, Vol. 1, 2nd Ed. Chapman and Hall, New York; and in Goodwin T W and Britton G (1988) Distribution and analysis of carotenoids. In: Goodwin T W (ed) Plant Pigments, pp 62–132. Academic Press, New York.

More than 640 different naturally-occurring carotenoids have been so far characterized, hence, carotenoids are responsible for most of the various shades of yellow, orange and red found in microorganisms, fungi, algae, plants and animals. Carotenoids are synthesized by all photosynthetic organisms as well as several nonphotosynthetic bacteria and fungi, however they are also widely distributed through feeding throughout the animal kingdom.

Carotenoids are synthesized de novo from isoprenoid precursors only in photosynthetic organisms and some microorganisms, they typically accumulate in protein complexes in the photosynthetic membrane, in the cell membrane and in the cell wall.

In the biosynthesis pathway of β-carotene, four enzymes convert geranylgeranyl pyrophosphate of the central isoprenoid pathway to β-carotene. Carotenoids are produced from the general isoprenoid biosynthetic pathway. While this pathway has been known for several decades, only recently, and mainly through the use of genetics and molecular biology, have some of the molecular mechanisms involved in carotenoids biogenesis, been elucidated. This is due to the fact that most of the enzymes which take part in the conversion of phytoene to carotenes and xanthophylls are labile, membrane-associated proteins that lose activity upon solubilization [see, Beyer P, Weiss G and Kleinig H (1985) Solubilization and reconstitution of the membrane-bound carotenogenic enzymes from daffodile chromoplasts. Eur J Biochem 153: 341–346; and, Bramley P M (1985) The in vitro biosynthesis of carotenoids. Adv Lipid Res 21: 243–279].

Carotenoids are synthesized from isoprenoid precursors. The central pathway of isoprenoid biosynthesis may be viewed as beginning with the conversion of acetyl-CoA to mevalonic acid. $D^3$-isopentenyl pyrophosphate (IPP), a $C_5$ molecule, is formed from mevalonate and is the building block for all long-chain isoprenoids. Following isomerization of IPP to dimethylallyl pyrophosphate (DMAPP), three additional molecules of IPP are combined to yield the $C_{20}$ molecule, geranylgeranyl pyrophosphate (GGPP). These 1'-4 condensation reactions are catalyzed by prenyl transferases [see, Kleinig H (1989) The role of plastids in isoprenoid biosynthesis. Ann Rev Plant Physiol Plant Mol Biol 40: 39–59]. There is evidence in plants that the same enzyme, GGPP synthase, carries out all the reactions from DMAPP to GGPP [see, Dogbo O and Camara B (1987) Purification of isopentenyl pyrophosphate isomerase and geranylgeranyl pyrophosphate synthase from *Capsicum* chromoplasts by affinity chromatography. Biochim Biophys Acta 920: 140–148; and, Laferriere A and Beyer P (1991) Purification of geranylgeranyl diphosphate synthase from *Sinapis alba* etioplasts. Biochim Biophys Acta 216: 156–163].

The first step that is specific for carotenoid biosynthesis is the head-to-head condensation of two molecules of GGPP to produce prephytoene pyrophosphate (PPPP). Following removal of the pyrophosphate, GGPP is converted to 15-cis-phytoene, a colorless $C_{40}$ hydrocarbon molecule. This two-step reaction is catalyzed by the soluble enzyme, phytoene synthase, an enzyme encoded by a single gene (crtB), in both cyanobacteria and plants [see, Chamovitz t), Misawa N, Sandmann G and Hirschberg J (1992) Molecular cloning and expression in *Escherichia coli* of a cyanobacterial gene coding for phytoene synthase, a carotenoid biosynthesis enzyme. FEBS Lett 296: 305–310; Ray J A, Bird C R, Maunders M, Grierson D and Schuch W (1987) Sequence of pTOM5, a ripening related cDNA from tomato. Nucl Acids Res 15: 10587–10588; Camara B (1993) Plant phytoene synthase complex—component 3 enzymes, immunology, and biogenesis. Meth Enzymol 214: 352–365]. All the subsequent steps in the pathway occur in membranes. Four desaturation (dehydrogenation) reactions convert phytoene to lycopene via phytofluene, ζ-carotene, and neurosporene. Each desaturation increases the number of conjugated double bonds by two such that the number of conjugated double bonds increases from three in phytoene to eleven in lycopene.

Relatively little is known about the molecular mechanism of the enzymatic dehydrogenation of phytoene [see, Jones B L and Porter J W (1986) Biosynthesis of carotenes in higher plants. CRC Crit Rev Plant Sci 3: 295–324; and, Beyer P, Mayer M and Kleinig H (1989) Molecular oxygen and the state of geometric iosomerism of intermediates are essential in the carotene desaturation and cyclization reactions in daffodil chromoplasts. Eur J Biochem 184: 141–150]. It has been established that in cyanobacteria, algae and plants the first two desaturations, from 15-cis-phytoene to ζ-carotene, are catalyzed by a single membrane-bound enzyme, phytoene desaturase [see, Jones B L and Porter J W (1986) Biosynthesis of carotenes in higher plants. CRC Crit Rev Plant Sci 3: 295–324; and, Beyer P, Mayer M and Kleinig H (1989) Molecular oxygen and the state of geometric iosomerism of intermediates are essential in the carotene desaturation and cyclization reactions in daffodil chromoplasts. Eur J Biochem 184: 141–150]. Since the ζ-carotene product is mostly in the all-trans configuration, a cis-trans isomerization is presumed at this desaturation step. The primary structure of the phytoene desaturase polypeptide in cyanobacteria is conserved (over 65% identical residues) with that of algae and plants [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966; Pecker 1, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht]. Moreover, the same inhibitors block phytoene desaturase in the two systems [see, Sandmann G and Boger P (1989) Inhibition of carotenoid biosynthesis by herbicides. In: Boger P and Sandmann G (eds) Target Sites of Herbicide Action, pp 25–44. CRC Press, Boca Raton, Fla.]. Consequently, it is very likely that the enzymes catalyzing the desaturation of phytoene and phytofluene in cyanobacteria and plants have similar biochemical and molecular properties, that are distinct from those of phytoene desaturases in other microorganisms. One such a difference is that phytoene desaturases from *Rhodobacter capsulatus, Erwinia* sp. or fungi convert phytoene to neurosporene, lycopene, or 3,4-dehydrolycopene, respectively.

Desaturation of phytoene in daffodil chromoplasts [see, Beyer P, Mayer M and Kleinig H (1989) Molecular oxygen and the state of geometric iosomerism of intermediates are essential in the carotene desaturation and cyclization reactions in daffodil chromoplasts. Eur J Biochem 184: 141–150], as well as in a cell free system of *Synechococcus* sp. strain PCC 7942 [see, Sandmann G and Kowalczyk S (1989) In vitro carotenogenesis and characterization of the phytoene desaturase reaction in *Anacystis*. Biochem Biophys Res Corn 163: 916–921], is dependent on molecular oxygen as a possible final electron acceptor, although oxygen is not directly involved in this reaction. A mechanism of dehydrogenase-electron transferase was supported in cyanobacteria over dehydrogenation mechanism of dehydrogenase-monooxygenase [see, Sandmann G and Kowalczyk S (1989) In vitro carotenogenesis and characterization of the phytoene desaturase reaction in *Anacystis*. Biochem Biophys Res Corn 163: 916–921]. A conserved FAD-binding motif exists in all phytoene desaturases whose primary structures have been analyzed [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966; Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht]. The phytoene desaturase enzyme in pepper was shown to contain a protein-bound FAD [see, Hugueney P, Romer S, Kuntz M and Camara B (1992) Characterization and molecular cloning of a flavoprotein catalyzing the synthesis of phytofluene and ζ-carotene in *Capsicum* chromoplasts. Eur J Biochem 209: 399–407]. Since phytoene desaturase is located in the membrane, an additional, soluble redox component is predicted. This hypothetical component could employ NAD(P)$^+$, as suggested [see, Mayer M P, Nievelstein V and Beyer P (1992) Purification and characterization of a NADPH dependent oxidoreductase from chromoplasts of *Narcissus pseudonarcissus*—a redox-mediator possibly involved in carotene desaturation. Plant Physiol Biochem 30: 389–398] or another electron and hydrogen carrier, such as a quinone. The cellular location of phytoene desaturase in *Synechocystis* sp. strain PCC 6714 and *Anabaena variabilis* strain ATCC 29413 was determined with specific antibodies to be mainly (85%) in the photosynthetic thylakoid membranes [see, Serrano A, Gimenez P, Schmidt A and Sandmann G (1990) Immunocytochemical localization and functional determination of phytoene desaturase in photoautotrophic prokaryotes. J Gen Microbiol 136: 2465–2469].

In cyanobacteria algae and plants ζ-carotene is converted to lycopene via neurosporene. Very little is known about the enzymatic mechanism, which is predicted to be carried out by a single enzyme [see, Linden H, Vioque A and Sandmann G (1993) Isolation of a carotenoid biosynthesis gene coding for ζ-carotene desaturase from *Anabaena* PCC 7120 by heterologous complementation. FEMS Microbiol Lett 106: 99–104]. The deduced amino acid sequence of ζ-carotene desaturase in *Anabaena* sp. strain PCC 7120 contains a dinucleotide-binding motif that is similar to the one found in phytoene desaturase.

Two cyclization reactions convert lycopene to β-carotene. Evidence has been obtained that in *Synechococcus* sp. strain PCC 7942 [see, Cunningham F X Jr, Chamovitz D, Misawa N, Gantt E and Hirschberg J (1993) Cloning and functional expression in *Escherichia coli* of a cyanobacterial gene for lycopene cyclase, the enzyme that catalyzes the biosynthesis of β-carotene. FEBS Lett 328: 130–138], as well as in plants [see, Camara B and Dogbo O (1986) Demonstration and solubilization of lycopene cyclase from *Capsicum* chromoplast membranes. Plant Physiol 80: 172–184], these two cyclizations are catalyzed by a single enzyme, lycopene cyclase. This membrane-bound enzyme is inhibited by the triethylamine compounds, CPTA and MPTA [see, Sandmann G and Boger P (1989) Inhibition of carotenoid biosynthesis by herbicides. In: Boger P and Sandmann G (eds) Target Sites of Herbicide Action, pp 25–44. CRC Press, Boca Raton, Fla.]. Cyanobacteria carry out only the β-cyclization and therefore do not contain ε-carotene, δ-carotene and α-carotene and their oxygenated derivatives. The β-ring is formed through the formation of a "carbonium ion" intermediate when the C-1,2 double bond at the end of the linear lycopene molecule is folded into the position of the C-5,6 double bond, followed by a loss of a proton from C-6. No cyclic carotene has been reported in which the 7,8 bond is not a double bond. Therefore, full desaturation as in lycopene, or desaturation of at least half-molecule as in neurosporene, is essential for the reaction. Cyclization of lycopene involves a dehydrogenation reaction that does not require oxygen. The cofactor for this reaction is unknown. A dinucleotide-binding domain was found in the lycopene cyclase polypeptide of *Synechococcus* sp. strain PCC 7942, implicating NAD(P) or FAD as coenzymes with lycopene cyclase.

The addition of various oxygen-containing side groups, such as hydroxy-, methoxy-, oxo-, epoxy-, aldehyde or carboxylic acid moieties, form the various xanthophyll species. Little is known about the formation of xanthophylls. Hydroxylation of β-carotene requires molecular oxygen in a mixed-function oxidase reaction.

Clusters of genes encoding the enzymes for the entire pathway have been cloned from the purple photosynthetic bacterium *Rhodobacter capsulatus* [see, Armstrong G A, Alberti M, Leach F and Hearst J E (1989) Nucleotide sequence, organization, and nature of the protein products of the carotenoid biosynthesis gene cluster of *Rhodobacter capsulatus*. Mol Gen Genet 216: 254–268] and from the nonphotosynthetic bacteria *Erwinia herbicola* [see, Sandmann G, Woods W S and Tuveson R W (1990) Identification of carotenoids in *Erwinia herbicola* and in transformed *Escherichia coli* strain. FEMS Microbiol Lett 71: 77–82; Hundle B S, Beyer P, Kleinig H, Englert H and Hearst J E (1991) Carotenoids of *Erwinia herbicola* and an *Escherichia coli* HB101 strain carrying the *Erwinia herbicola* carotenoid gene cluster. Photochem Photobiol 54: 89–93; and, Schnurr G, Schmidt A and Sandmann G (1991) Mapping of a carotenogenic gene cluster from *Erwinia herbicola* and functional identification of six genes. FEMS Microbiol Lett 78: 157–162] and *Erwinia uredovora* [see, Misawa N, Nakagawa M, Kobayashi K, Yamano S, Izawa I, Nakamura K and Harashima K (1990) Elucidation of the *Erwinia uredovora* carotenoid biosynthetic pathway by functional analysis of gene products in *Escherichia coli*. J Bacteriol 172: 6704–6712]. Two genes, al-3 for GGPP synthase [see, Nelson M A, Morelli G, Carattoli A, Romano N and Macino G (1989) Molecular cloning of a *Neurospora crassa* carotenoid biosynthetic gene (albino-3) regulated by blue light and the products of the white collar genes. Mol Cell Biol 9: 1271–1276; and, Carattoli A, Romano N, Ballario P, Morelli G and Macino G (1991) The *Neurospora crassa* carotenoid biosynthetic gene (albino 3). J Biol Chem 266: 5854–5859] and al-1 for phytoene desaturase [see, Schmidhauser T J, Lauter F R, Russo VEA and Yanofsky C (1990) Cloning sequencing and photoregulation of al-1, a carotenoid biosynthetic gene of *Neurospora crassa*. Mol Cell Biol 10: 5064–5070] have been cloned from the fungus *Neurospora crassa*. However, attempts at using these genes as heterologous molecular probes to clone the corresponding genes from cyanobacteria or plants were unsuccessful due to lack of sufficient sequence similarity.

The first "plant-type" genes for carotenoid synthesis enzyme were cloned from cyanobacteria using a molecular-genetics approach. In the first step towards cloning the gene for phytoene desaturase, a number of mutants that are resistant to the phytoene-desaturase-specific inhibitor, norflurazon, were isolated in *Synechococcus* sp. strain PCC 7942 [see, Linden H, Sandmann G, Chamovitz D, Hirschberg J and Boger P (1990) Biochemical characterization of *Synechococcus* mutants selected against the bleaching herbicide norflurazon. Pestic Biochem Physiol 36: 46–51]. The gene conferring norflurazon-resistance was then cloned by transforming the wild-type strain to herbicide resistance [see, Chamovitz D, Pecker I and Hirschberg J (1991) The molecular basis of resistance to the herbicide norflurazon. Plant Mol Biol 16: 967–974; Chamovitz D, Pecker I, Sandmann G, Boger P and Hirschberg J (1990) Cloning a gene for norflurazon resistance in cyanobacteria. Z Naturforsch 45c: 482–486]. Several lines of evidence indicated that the cloned gene, formerly called pds and now named crtP, codes for phytoene desaturase. The most definitive one was the functional expression of phytoene desaturase activity in transformed *Escherichia coli* cells [see, Linden H, Misawa N, Chamovitz D, Pecker I, Hirschberg J and Sandmann G (1991) Functional complementation in *Escherichia coli* of different phytoene desaturase genes and analysis of accumulated carotenes. Z Naturforsch 46c: 1045–1051; and, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966]. The crtP gene was also cloned from *Synechocystis* sp. strain PCC 6803 by similar methods [see, Martinez-Ferez I M and Vioque A (1992) Nucleotide sequence of the phytoene desaturase gene from *Synechocystis* sp. PCC 6803 and characterization of a new mutation which confers resistance to the herbicide norflurazon. Plant Mol Biol 18: 981–983].

The cyanobacterial crtP gene was subsequently used as a molecular probe for cloning the homologous gene from an alga [see, Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht] and higher plants [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536; and, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966]. The phytoene desaturases in *Synechococcus* sp. strain PCC 7942 and *Synechocystis* sp. strain PCC 6803 consist of 474 and 467 amino acid residues, respectively, whose sequences are highly conserved (74% identities and 86% similarities). The calculated molecular mass is 51 kDa and, although it is slightly hydrophobic (hydropathy index –0.2), it does not include a hydrophobic region which is long enough to span a lipid bilayer membrane. The primary structure of the cyanobacterial phytoene desaturase is highly conserved with the enzyme from the green alga *Dunalliela bardawil* (61% identical and 81% similar; [see, Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht]) and from tomato [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966], pepper [see, Hugueney P, Romer S, Kuntz M and Camara B (1992) Characterization and molecular cloning of a flavoprotein catalyzing the synthesis of phytofluene and ζ-carotene in *Capsicum* chromoplasts. Eur J Biochem 209: 399–407] and soybean [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536] (62–65% identical and ~79% similar; [see, Chamovitz D (1993) Molecular analysis of the early steps of carotenoid biosynthesis in cyanobacteria: Phytoene synthase and phytoene desaturase. Ph.D. Thesis, The Hebrew University of Jerusalem]). The eukaryotic phytoene desaturase polypeptides are larger (64 kDa); however, they are processed during import into the plastids to mature forms whose sizes are comparable to those of the cyanobacterial enzymes.

There is a high degree of structural similarity in carotenoid enzymes of *Rhodobacter capsulatus*, *Erwinia* sp. and *Neurospora crassa* [reviewed in Armstrong G A, Hundle B S and Hearst J E (1993) Evolutionary conservation and structural similarities of carotenoid biosynthesis gene products from photosynthetic and nonphotosynthetic organisms. Meth Enzymol 214: 297–311], including in the crtI gene-product, phytoene desaturase. As indicated above, a high degree of conservation of the primary structure of phytoene desaturases also exists among oxygenic photosynthetic organisms. However, there is little sequence similarity, except for the FAD binding sequences at the amino termini, between the "plant-type" crtP gene products and the "bacterial-type" phytoene desaturases (crtI gene products; 19–23% identities and 42–47% similarities). It has been hypothesized that crtP and crtI are not derived from the same ancestral gene and that they originated independently through convergent evolution [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966]. This hypothesis is supported by the different dehydrogenation sequences that are catalyzed by the two types of enzymes and by their different sensitivities to inhibitors.

Although not as definite as in the case of phytoene desaturase, a similar distinction between cyanobacteria and plants on the one hand and other microorganisms is also seen in the structure of phytoene synthase. The crtB gene (formerly psy) encoding phytoene synthase was identified in the genome of *Synechococcus* sp. strain PCC 7942 adjacent to crtP and within the same operon [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536]. This gene encodes a 36-kDa polypeptide of 307 amino acids with a hydrophobic index of −0.4. The deduced amino acid sequence of the cyanobacterial phytoene synthase is highly conserved with the tomato phytoene synthase (57% identical and 70% similar; Ray J A, Bird C R, Maunders M, Grierson D and Schuch W (1987) Sequence of pTOM5, a ripening related cDNA from tomato. Nucl Acids Res 15: 10587–10588]) but is less highly conserved with the crtB sequences from other bacteria (29–32% identical and 48–50% similar with ten gaps in the alignment). Both types of enzymes contain two conserved sequence motifs also found in prenyl transferases from diverse organisms [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536; Carattoli A, Romano N, Ballario P, Morelli G and Macino G (1991) The *Neurospora crassa* carotenoid biosynthetic gene (albino 3). J Biol Chem 266: 5854–5859; Armstrong G A, Hundle B S and Hearst J E (1993) Evolutionary conservation and structural similarities of carotenoid biosynthesis gene products from photosynthetic and nonphotosynthetic organisms. Meth Enzymol 214: 297–311; Math S K, Hearst J E and Poulter C D (1992) The crtE gene in *Erwinia herbicola* encodes geranylgeranyl diphosphate synthase. Proc Natl Acad Sci USA 89: 6761–6764; and, Chamovitz D (1993) Molecular analysis of the early steps of carotenoid biosynthesis in cyanobacteria: Phytoene synthase and phytoene desaturase. Ph.D. Thesis, The Hebrew University of Jerusalem]. It is conceivable that these regions in the polypeptide are involved in the binding and/or removal of the pyrophosphate during the condensation of two GGPP molecules.

The crtQ gene encoding ζ-carotene desaturase (formerly zds) was cloned from *Anabaena* sp. strain PCC 7120 by screening an expression library of cyanobacterial genomic DNA in cells of *Escherichia coli* carrying the *Erwinia* sp. crtB and crtE genes and the cyanobacterial crtP gene [see, Linden H, Vioque A and Sandmann G (1993) Isolation of a carotenoid biosynthesis gene coding for ζ-carotene desaturase from *Anabaena* PCC 7120 by heterologous complementation. FEMS Microbiol Lett 106: 99–104]. Since these *Escherichia coli* cells produce ζ-carotene, brownish-red pigmented colonies that produced lycopene could be identified on the yellowish background of cells producing ζ-carotene. The predicted ζ-carotene desaturase from *Anabaena* sp. strain PCC 7120 is a 56-kDa polypeptide which consists of 499 amino acid residues. Surprisingly, its primary structure is not conserved with the "plant-type" (crtP gene product) phytoene desaturases, but it has considerable sequence similarity to the bacterial-type enzyme (crtI gene product) [see, Sandmann G (1993) Genes and enzymes involved in the desaturation reactions from phytoene to lycopene. (abstract), 10th International Symposium on Carotenoids, Trondheim CL1–2]. It is possible that the cyanobacterial crtQ gene and crtI gene of other microorganisms originated in evolution from a common ancestor.

The crtL gene for lycopene cyclase (formerly lcy) was cloned from *Synechococcus* sp. strain PCC 7942 utilizing essentially the same cloning strategy as for crtP. By using an inhibitor of lycopene cyclase, 2-(4-methylphenoxy)-triethylamine hydrochloride (MPTA), the gene was isolated by transformation of the wild-type to herbicide-resistance [see, Cunningham F X Jr, Chamovitz D, Misawa N, Gantt E and Hirschberg J (1993) Cloning and functional expression in *Escherichia coli* of a cyanobacterial gene for lycopene cyclase, the enzyme that catalyzes the biosynthesis of β-carotene. FEBS Lett 328: 130–138]. Lycopene cyclase is the product of a single gene product and catalyzes the double cyclization reaction of lycopene to β-carotene. The crtL gene product in *Synechococcus* sp. strain PCC 7942 is a 46-kDa polypeptide of 411 amino acid residues. It has no sequence similarity to the crty gene product (lycopene cyclase) from *Erwinia uredovora* or *Erwinia herbicola*.

The gene for β-carotene hydroxylase (crtZ) and zeaxanthin glycosilase (crtX) have been cloned from *Erwinia herbicola* [see, Hundle B, Alberti M, Nievelstein V, Beyer P, Kleinig H, Armstrong G A, Burke D H and Hearst J E (1994) Functional assignment of *Erwinia herbicola* Eho10 carotenoid genes expressed in *Escherichia coli*. Mol Gen Genet 254: 406–416; Hundle B S, Obrien D A, Alberti M, Beyer P and Hearst J E (1992) Functional expression of zeaxanthin glucosyltransferase from *Erwinia herbicola* and a proposed diphosphate binding site. Proc Natl Acad Sci USA 89: 9321–9325] and from *Erwinia uredovora* [see, Misawa N, Nakagawa M, Kobayashi K, Yamano S, Izawa I, Nakamura K and Harashima K (1990) Elucidation of the *Erwinia uredovora* carotenoid biosynthetic pathway by functional analysis of gene products in *Escherichia coli*. J Bacteriol 172: 6704–6712].

Carotenoids as Antioxidants:

Most carotenoids are efficient antioxidants, quenching singlet oxygen ($^1O_2$) and scavenging peroxyl radicals (Sies and Stahl, 1995). $^1O_2$, $O_2^-$, $H_2O_2$ and peroxyl radicals are reactive oxygen species generated in biological cells. All these species may react with DNA, proteins and lipids impairing their physiological functions (Halliwell, 1996). Such processes are discussed as initial events in the pathogenesis of several diseases including cancer, cardiovascular diseases, or age-related system degeneration. Carotenoids inactivate singlet oxygen via physical or chemical quenching. The efficacy of physical quenching exceeds that of chemical quenching by far, 99.9%, and involves that transfer of excitation energy from $^1O_2$ to the carotenoid. In the process of physical quenching the carotenoid remains intact, so that it can undergo further cycles of singlet oxygen quenching. Methylene blue was used as a sensitizer to study the consumption of carotenoids during photooxidation of human plasma and LDL (Ojima et al., 1993). Lycopene, β-carotene and xanthophylls were found to decrease photooxidation in blood plasma while they remained unchanged (Wagner et al., 1993). Hirayama et al. (1994) investigated the singlet oxygen quenching ability of 18 carotenoids and reported that the xanthophylls conjugated keto group enhanced quenching, while hydroxy, epoxy and methoxy groups showed lesser effects.

Capsanthin and capsorubin were found to act as better singlet oxygen quenchers than β-carotene. Previous studies show that β-carotene is a good scavenger of hypochlorite and others have demonstrated its scavenging ability of nitrogen dioxide. (Kanner et al., 1983, Everett et al., 1996).

Carotenoids are efficient scavengers of peroxyl radicals, especially at low oxygen tension (Burton and Ingold, 1984; Kennedy and Liebler, 1992). The interaction of carotenoids with peroxyl radicals generated by the azo compounds AMVN and AAPH in a phosphatidylcholine liposome system were investigated by Lin et al. (1992). In this system the xanthophylls astaxanthin, zeaxanthin and cantaxanthin were more efficient free radical scavengers than β-carotene. However, investigating the reaction of carotenoids with peroxyl free radical in emulsion showed that lycopene and β-carotene are better scavengers than several xanthophylls (Woodall et al., 1997). Matsufuji et al. (1998) investigated the radical scavenging ability of carotenoids in methyl linoleate emulsion and demonstrated that capsanthin acts better than lutein, zeaxanthin and β-carotene.

Oxidative modification of low-density lipoproteins (LDL), which is thought to be a key step in early atherosclerosis, is protected by the lipoprotein-associated antioxidants. LDL contains about 1 carotenoid and 12 α-tocopherol molecules per LDL particle, a relatively small number compared with about 2,300 molecules of oxidizable lipid in each LDL particle (Romanchik et al., 1995). Some antioxidant supplements, such as α-tocopherol consistently appear to enhance the ability of LDL to resist oxidation, (Esterbauer et al., 1991; Aviram, 1999). However, β-carotene shows less consistent protective ability (Gaziano et al., 1995; Reaven et al., 1994). In contrast, Lin et al. (1998) showed that depletion of β-carotene in healthy women increased the susceptibility of LDL to oxidation, whereas a normal intake provide protection to LDL. Most recently, dietary supplementation with β-carotene, but not lycopene was shown to inhibit endothelial cell—mediated ex-vivo per oxidation of LDL (Dugas et al., 1999). Mixture of carotenoids have been found to be more effective than any single carotenoid in protecting liposomes against lipid peroxidation (Stahl et al., 1998), and as antioxidants in membranes and LDL. Moreover, it has been reported that carotenoids enhance vitamin E antioxidant efficiency (Bohm et al., 1997; Fuhrman et al., 1997; Fuhrman and Aviram, 1999).

Atherosclerosis and LDL Oxidation as Affected by Carotenoids During Atherogenesis:

Atherosclerosis is the major cause of morbidity and mortality in the western world and its pathogenesis involves complicated interacting among cells of the arterial wall, blood cells, and plasma lipoproteins (Ross, 1993). Macrophage cholesterol accumulation and foam cell formation are the indications of early atherogenesis with most of the cholesterol in these cells derived from plasma low-density lipoproteins (LDL). The most studied modification of LDL with a potential pathological significance is LDL oxidation (Steinberg et al., 1989). The involvement of oxidized LDL in atherosclerosis is suggested from its presence in the atherosclerotic lesion in human and of the apolipoprotein E deficient ($E^o$) mice (Yla-Herttula et al., 1989; Aviram et al., 1995), from the increased susceptibility to oxidation of LDL derived from atherosclerotic patients and also from the anti-atherogenecity of several dietary antioxidants (Steinberg et al., 1992; Frankel et al., 1993; Aviram, 1996).

High-density lipoproteins (HDL) are associated with anti-atherogenic activity and HDL levels are inversely related to the risk of developing atherosclerosis. Paraoxonase, an enzyme, physically associated in serum with HDL, has been shown to be inversely related to the risks of atherogenesis (Watson et al., 1995; Aviram, 1999). The LDL oxidation hypothesis of atherosclerosis raised an extensive investigation into the role of antioxidants against LDL oxidation as a possible preventive treatment for atherosclerosis. Efforts are made to identify natural food products, which offer antioxidant defense against LDL oxidation.

Consumption of flavonoids in the diet has been shown to be inversely associated with morbidity from coronary heat disease, (Hertog et al., 1993; Knekt et al., 1996). Flavonoids extracted from red wine protected LDL oxidation where added in-vitro (Frankel et al., 1993) and consumption of red wine was shown to inhibit LDL oxidation ex-vivo (Kondo, 1994; Fuhrman et al., 1995).

Carotenoid consumption has been shown in previous epidemiological studies to be associated with reduced cardiovascular mortality (Kohlmeier and Hasting, 1995). However, several dietary intervention trials involving β-carotene have yielded inconclusive results (Mayne, 1996). Lee et al. (1999) reported that among healthy women given a β-carotene supplement for a limited time, no benefit or harm was observed regarding incidence of cancer and of cardiovascular diseases. Lower serum lycopene levels were associated with increase risk and mortality from coronary heart disease in a cross sectional study of Lithuanian and Swedish populations (Kristenson et al., 1997; Rao and Agarwal, 1999). Iribarren et al. (1997) found the xanthophylls lutein and zeaxanthin to be the carotenoid with the strongest inverse association with extreme carotid artery intima-medial thickening.

Cancer and the Effects of Carotenoids:

Cancer development is characterized by specific cellular transformations followed by uncontrolled cell growth and invasion of the tumor site with a potential for subsequent detachment, transfer into the blood stream and metastases formation at distal site(s) (Ilyas et al., 1999). All these stages involve a number of cellular alterations including changes in proliferation rates, inactivation of tumor suppressor genes and inhibition of apoptosis (Goldsworthy et al., 1996; Knudsen et al., 1999; Ilyas et al., 1999).

Dietary exposures provide one of the environmental factors believed to be significant in the etiology of a number of epithelioid cancer cases, notably oral and colon carcinomas. Cancer inhibitory properties for a number of micronutrients with antioxidant properties have been demonstrated in recent years mainly in experimental animal models (Jain et al., 1999), in cell culture studies (Schwartz and Shklar, 1992), and in some human studies (Schwartz et al., 1991). Epidemiological evidence links nutrition rich in vegetables and fruits, with reduced risks of degenerative disease, the evidence is particular compelling for cancer (Block et al., 1992). Epidemiological studies suggest that the incidence of human cancer is inversely correlated with the dietary intake of carotenoids and their concentration in plasma (Ziegler, 1988). A variety of carotenoids are present in commonly eaten foods and these compounds accumulate in tissues and blood plasma. Animal studies and cultured cell studies have shown that many carotenoids such as α-carotene, β-cryptoxanthin, astaxanthin and lycopene have anticarcinogenic activities. (Murakoshi et al., 1992; Tanaka et al., 1995; Levy et al., 1995). However, there have been contradictory reports concerning the use of β-carotene for cancer prevention (Hannekens et al., 1996). A multicenter case-control study to evaluate the relation between antioxidant status and cancer has shown that lycopene but not β-carotene, contribute to the protective effect of vegetable consumption (Kohlmeier et al., 1997).

The putative biological mechanisms of cancer inhibition of the antioxidant micronutrients are:

(1) Enhancement of production of cytotoxic immune cells and production of cytokines (Schwartz et al., 1990).

(2) Activation of cancer suppressor genes such as wild p53 (Schwartz et al., 1993), or deactivation of oncogenes such as Ha-ras and mutated p53 (Schwartz et al., 1992).

(3) Inhibition of angiogenesis-stimulating factors involved with tumor angiogenesis (Schwartz and Shklar, 1997).

Primary prevention or drug-based therapeutics of oral and colon cancer is a public health goal but still not feasible despite major advances in understanding of the mechanisms at the genetic, germline, somatic, immunologic and angiogenic levels. Therefore, a great interest in preventive nutrition has arisen focusing on the role of dietary components with antioxidant activity such as several vitamins and carotenoids, to prevent cancer (Weisburger, 1999).

Oral Cancer:

The frequency of oral cancer is 4–5% of all cancer cases in the western world. Squamous cell carcinoma (SCC) make up 95% of oral cancer cases. Risk factors in oral cancer include tobacco as a major risk factor, and alcohol abuse, especially when used in combination with tobacco (De Stefani et al., 1998; Hart et al., 1999; Schildt et al., 1998; Dammer et al., 1998; Bundgaard et al., 1995). Viral Infections, particularly with several species of Human Papilloma Virus (HPV) have been associated with both benign and malignant oral lesions (Smith et al., 1998).

Leukoplakia is the most common pre-neoplastic condition. Leukoplakia presents as white lesions on the oral mucosa, while erythroleukoplakia is a variant of leukoplakia in which the clinical presentation includes erythematous area as well. When biopsied, leukoplakia may show a spectrum of histologic changes ranging from hyperkeratosis, dysplasia to carcinoma-in-situ or even invasive carcinoma. Dysplastic changes are more frequent in erythroleokoplakia. Leukoplakia is considered a pre-neoplastic lesion, which carries a 15% risk for malignant transformation over time if dysplasia is not diagnosed in the initial biopsy, and up to 36% transformation for lesions with dysplasia at the time of first biopsy (Mao, 1997). Leukoplakia is associated with the use of tobacco in the majority of cases, but cases of leukoplakia in non-smoking women, have a higher risk. When leukoplakia is diagnosed, the treatment protocol consists of cessation of risk habits, and frequent follow-up, including repeated biopsies. No effective long-term preventive treatment is yet available.

Ki67, PCNA, CyclinD1, p53, p16, and p21 are all cell cycle associated proteins, which are over-expressed in oral cancer and pre-cancer, and are associated with a negative prognosis in cancer cases (Schoelch et al., 1999; Yao et al., 1999; Birchall et al., 1999).

The Role of Carotenoids in the Prevention of Oral Cancer:

Vitamin A and its derivatives, by way of systemic administration or topical application have been shown to be beneficial in regressing leukoplakia. In cases of oral cancer, vitamin-A and its derivatives have been shown to reduce the risk of secondary cancer (Hong et al., 1990; Gravis et al., 1999). However, in long term use they are associated with significant side effects, and the lesions tend to recur when treatment is discontinued. Beta-carotenes are not associated with significant side effects, and there is evidence from experimental studies that indicate they may be effective in inhibiting malignant transformation, however, there is contradictory data regarding their efficiency in clinical use for oral cancer and pre-cancer (Stich et al., 1998). A recent study has shown significantly lower levels of serum β-carotene and of tissue β-carotene in smokers, which are at risk for developing oral cancer (Cowan et al., 1999).

The prognosis of oral cancer is generally poor. The mean five-year survival of oral cancer cases is only about 50%, and although much improved diagnostic and treatment tools have been introduced, survival has not improved over the last two decades.

Treatment consists of surgery radiation and chemotherapy, and in most cases is associated with severe effects on the quality of life, such as impaired esthetics, mastication, and speech.

In view of the poor prognosis of oral cancer, prevention and regression at the pre-malignant stage is of enormous importance. However when a pre-malignant lesion such as leukoplakia is identified, very few efficient treatment modalities are yet available for routine practice. Therefore, a continuing effort is necessary to identify new compounds that will be able to regress existing lesions and prevent their transformation into malignancy, with minimal or no side effects, to allow for long term use in patients at risk. It is also important to find chemopreventing agents that will reduce the risk for secondary cancer in patients with primary oral cancer, which is as high as 36%.

Colon Cancer:

Colon cancer is the third most common form of cancer and the overall estimated new cases per year worldwide represent about 10% of all new cancer cases. The disease is most frequent in Occidental countries including Israel. Epidemiological studies have emphasized the major role of diet in the ethiology of colon cancer. Attempts to identify causative or protective factors in epidemiological and experimental studies have led to some discrepancies. Nonetheless, prospects for colorectal cancer control are bright and a number of possible approaches could prove fruitful. Bras and associates (1999) have recently demonstrated that in familial adenomatous polyposis patients, a population highly prone to develop colorectal cancer, exhibit an imbalance in the pro-oxidant/antioxidant status. In addition, the levels of ascorbate and tocopherol were considerably lower in this population. Collins et al. (1998) have shown in populations from five different European countries that the mean 8-oxodeoxyguanosine (8-oxo-dG) concentrations in lymphocyte DNA showed a significant positive correlation with colorectal cancer. It would appear that patients with colonic cancer undergo a significant reduction in their antioxidant reserve compared to healthy subjects. These studies support the notion that one approach to identify protective factors in colorectal canter will be those that provide a balanced oxidative status, or fit the antioxidant hypothesis. This hypothesis proposes that vitamin C, vitamin E, and carotenoids occurring in fruits and vegetables afford protection against cancer by preventing oxidative damage to lipids and to DNA.

The Role of Carotenoids in the Prevention of Colon Cancer:

Recent studies suggest a protective effect of carotenoids and antioxidants, lycopene and lycopene-rich tomatoes against various cancers, among them, colon cancer.

Rats with induced colon cancer fed lycopene or tomato juice/water solution, had shown a lower colon cancer incidence than the control group. The protective effect against colon preneoplasia associated with enhanced antioxidant properties was observed in a study where rats were administered a carcinogen and administered lycopene in the form of 6% oleoresin supplementation (Jain et al., 1999). Chemoprevention by lycopene of mouse lung neoplasia has also been reported (Kim et al., 1997). Kim et al. (1988) assessed the effect of carotenoids, such as fucoxanthin, lutein and phenolics such curcumin and its derivative tetrahydrocurcumin (THC) on colon cancer development in mice. Flucoxanthin, lutein, carcumin and THC significantly decreased the number of aberrant crypt foci compared to the control group. Proliferation rate was lower following this treatment, with higher effectiveness seen by THC. A similar effect was reported by Narisawa and associates (1996) with the exception for β-carotene.

Human studies conducted by Pappalardo et al., (1997), compared the status of carotenoids in tissue and plasma in healthy subjects and subjects with pre-cancer and cancerous lesions. The cancer subjects had lower levels of carotenoid than those of healthy subjects.

Genetic and Breeding of Red Pepper:

Red pepper is one of the richest sources of carotenoids among vegetable crops. Most of the domesticated varieties of red pepper belong to the species *Capsicum annuum*; pepper breeding has focused and evolved mainly on the development of cultivars and varieties suited for use as a vegetable, spice condiment, ornamental or medicinal plant. Few studies have been devoted to the improvement of the chemical and nutritional composition of peppers (Bosland, 1993; Poulos, 1994). Capsanthin is the predominant carotenoid of the red pepper fruit and its content is controlled by major genes and polygenes; several genes have been identified along its biosynthetic pathway (Lefebvre, 1998).

Carotenoids from Red Pepper Fruits:

Red pepper fruits, especially from paprika cultivars are used in the form of powders and oleoresins as food colorants. These products are very rich in carotenoids, some of them specific to pepper fruits. The keto carotenoid, capsanthin, occur only in red pepper, represents 50% the carotenoids in the vegetable and contribute to the red color. Zeaxanthin and lutein, β-carotene and β-cryptoxanthin are the additional carotenoids found in red pepper at concentrations of 20%, 10% and 5%, respectively (Levy et al., 1995). Capsanthin accounts for 30–60% of total carotenoids in fully ripe fruits. The capsanthin is esterified with fatty acids (nonesterified 20%; monoesterified 20–30%; diesterified 40–50%). The fatty acids of esterified capsanthins are chiefly lauric (12:0), myristic (14:0) and palmitic (16:0) acid.

Increasing the carotenoid concentration in high-pigment fruits of red pepper by genetic manipulation seems to improve not only the quality of the fruit as a food colorant but also as an important source of carotenoids, particularly, capsanthin. It was found that the breeding line 4126 contains about 240 mg carotenoids/100 grams fresh weight of which 120 mg are capsanthin (Levy et al., 1995). Tomatoes contain about 5 mg lycopene/100 grams fresh weight, and only in special breeding lines, levels of 15 mg lycopene/100 grams fresh weight are achieved. These enormous differences in carotenoid content emphasizes the high potential of red pepper cultivars as an appropriate food source with high carotenoid concentration.

Bioavailability of Carotenoids:

As a result of their lipophilic nature, carotenoids are often found complexed in the food matrix with proteins, lipids and or fiber. Several steps are necessary for carotenoid absorption to occur. The food matrix must be digested and the carotenoids must be released, physically and biochemically, and combined with lipids and bile salts to form micelles. The micelles must move to the intestinal brush border membrane for absorption and be transported into the enterocyte for subsequent processing. The chylomicrons move to the liver and are transported by lipoproteins for distribution to the different organs. Part of the carotenoids in chylomicrons remnants are taken up by extra-hepatic tissues before hepatic uptake (Lee et al., 1999). Thus, many factors influence absorption and hence bioavailability of dietary carotenoids. Humans absorb a variety of carotenoids intact, and some carotenoids such, as β-carotene, β-cryptoxanthin and α-carotene can contribute to the vitamin A status of the individual (Olson, 1999). Mathews-Roth et al. (1990) studied the absorption and distribution of ($^{14}$C) canthaxanthin, a typical xanthophyll, and ($^{14}$C) lycopene, an acyclic hydrocarbon carotenoid, in rats and rhesus monkeys. They showed that the liver accumulated the largest amount of both, however clearance of lycopene was much slower than canthaxanthin. Stahl and Sies (1992) showed that the lycopene concentration in human plasma was increased by the consumption of heat-processed tomato juice. Recently it was found in humans that in a single ingestion of paprika juice containing 34.2 μmole capsanthin and a week later tomato soup, containing 186.3 μmole lycopene, resulted in elevation of plasma carotenoids from both sources. The plasma contain only deesterified carotenoids including non-esterified capsanthin. The results also show that capsanthin disappear from the plasma more rapidly than lycopene (Oshima et al., 1997). Rainbow trout were fed diet supplemented with canthaxanthin and oleoresin paprika. Canthaxanthin was more efficient absorbed in the flesh of rainbow trout than paprika carotenoids (Akhtar et al., 1999).

Bioavailability of Carotenoids Esteriflied with Fatty Acids:

The bioavailability of paprika carotenoids in human and animal were shown to be lower than β-carotene or canthaxanthin (Akhtar et al., 1999). One of the reason to this reduced absorption seems to occur because most of the carotenoids are in an ester form with fatty acids. It is shown herein that pancreatic lipase catalyze the deesterification of paprika carotenoids to a very limited extent. This could explain the low bioavailability of carotenoids from paprika in animals.

Thus although the red pepper fruit is the richest in carotenoids of all other sources, the bioavailability of red pepper carotenoids is poor because red pepper carotenoids are esterified with fatty acids, which prevent their efficient uptake in the gut.

Enzymatic Treatment of Esterified Carotenoids:

Several studies have indicated that esterified carotenoids may be substrates for enzymatic hydrolysis. Japanese Laid-Open Patent No. 59-91155 to Masahiro et al. teaches a method for manufacture of a stable, odorless pigment from natural carotenoid-containing materials by transesterification. The authors demonstrated that molecular distillation, using a thin-film or falling film apparatus, may be used to purify carotenoids following the chemical conversion of odiferous unsaturated fatty acid residues of oleoresin to saturated fatty acids, and that a lipase from *Candida cylindracea* (renamed *Candida rugosa*) can be useful as an auxilliary agent in the transesterification. Although the resultant transesterified, fatty acid-containing carotenoid pigments disclosed are more stable, and less odiferous than the native pigments, the production of free carotenoids is not mentioned.

Lipase is known to be important in the in-vivo hydrolysis of esters of Vitamin A (Harrison, J Nutr 2000; 130:

340S–344S). Similarly, lipase has been used in the synthesis of Vitamin A, in the acylation and esterification of Vitamin A precursors (U.S. Pat. No. 5,902,738 to Orsat et al; Maugard et al, Biotechnol Prog 2000; 16:358–362), and in the esterification of the carotenoid (3R, 3'R, 6'R) lutein to (3R, 3'R) zeaxanthin (Khachik F, J Nat Prod; 2003:66: 67–70).

In an attempt to identify the key lipases responsible for metabolism of carotenoids in the gut, Breithaupt et al. (Compar. Biochem and Physiol PartB 2002; 132:721–28) compared the substrate specificity of a number of lipases towards various red and yellow carotenoids and derivatives (Vitamin A). They found that whereas the retinyl palmitate was readily hydrolyzed by pancreatic lipase, carotenoid diesters were poor substrates for pancreatic lipase and Candida rugosa lipase. Results with cholesterol esterase were better, but no quantitative deesterification, similar to the results with retinyl palmitate, was observed.

Breithaupt (Breithaupt, D E, et al, Z. Naturforsch 2000; 55:971–75) and Khachik (Khachik F, et al, Anal Chem 1997; 69:1873–81) describe partial hydrolysis of natural carotenoids using lipase. Khachik et al. used lipase for analysis of the carotenoid and carotenoid metabolites in human milk and serum. Breithaupt used *C. rugosa* lipase for enzymatic treatment of natural esterified red and green pepper carotenoids, but was only partially successful, producing a preparation comprising a mixture of deesterified and esterified carotenoids, as analyzed by HPLC. Similar inability to demonstrate efficient, quantitative enzymatic hydrolysis of natural carotenoids had been reported using *Pseudomonas fluorescens* cholesterol esterase (Jacobs, et al, Comp Biochem Physiol 1982; 72B:157–160). In describing his failure to reduce the contamination of the carotenoid product with mono- and diesterified carotenoids, Breithaupt hypothesized that the persistence of mono- and diesterified derivatives of the red-pepper carotenoid capsanthin was due to substrate specificity of the lipase, concluding that "neither diesterified nor monoesterified carotenoids are preferred substrates" (Breithaupt, D E Z. Naturforsch 55c; page 974, right column to page 975, left column).

There is thus a widely recognized need for, and it would be highly advantageous to have, a method of efficient deesterification of esterified carotenoids devoid of the limitations inherent in chemical saponification, so as to render such carotenoids bioavailable to human and animal.

SUMMARY OF THE INVENTION

According to one aspect of the present invention there is provided a method of extracting red pepper oleoresin, the method comprising homogenizing red-pepper fruits in water into a juice; centrifuging the juice so as to obtain a pellet; mixing the pellet with ethanol and ethyl acetate; homogenizing the pellet with the ethanol and the ethyl acetate; removing dry material; and evaporating solvents so as to obtain red pepper oleoresin.

According to further features in preferred embodiments of the invention described below, a weight ratio between the red-pepper fruits and the water is 80–120 parts of fruit to 20–60 parts of water.

According to still further features in the described preferred embodiments the red-pepper fruits are frozen.

According to still further features in the described preferred embodiments the red-pepper fruits are fresh.

According to still further features in the described preferred embodiments the juice is centrifuged at 20,000–30,000 g for 10–30 minutes.

According to still further features in the described preferred embodiments the pellet is mixed with 1–3 parts of the ethanol and 5–15 parts of the ethyl acetate.

According to still further features in the described preferred embodiments removing the dry material is by centrifugation.

According to still further features in the described preferred embodiments evaporating the solvents is at 40–50° C.

According to still further features in the described preferred embodiments evaporating the solvents is under vacuum.

According to another aspect of the present invention there is provided a method of determining an efficiency of an esterase in increasing a fraction of free carotenoids in a source of carotenoids in which at least some of the carotenoids are fatty acid esterified carotenoids, the method comprising contacting the source of carotenoids with the esterase under preselected experimental conditions; and using a carotenoids detection assay for determining the efficiency of the esterase in increasing the fraction of the free carotenoids in the source of carotenoids.

According to still another aspect of the present invention there is provided a method of screening for esterases efficient in increasing a fraction of free carotenoids in a source of carotenoids in which at least some of the carotenoids are fatty acid esterified carotenoids, the method comprising contacting the source of carotenoids separately with each of the esterases under preselected experimental conditions; and using a carotenoids detection assay for determining the efficiency of each of the esterases in increasing the fraction of the free carotenoids in the source of carotenoids, thereby screening for esterases efficient in increasing the fraction of free carotenoids in the source of carotenoids.

According to yet another aspect of the present invention there is provided a method of optimizing reaction conditions for increasing a fraction of free carotenoids in a source of carotenoids in which at least some of the carotenoids are fatty acid esterified carotenoids, via an esterase, the method comprising contacting the source of carotenoids with the esterase under different preselected experimental conditions; and using a carotenoids detection assay for determining the efficiency of the esterase in increasing the fraction of the free carotenoids in the source of carotenoids under each of the different preselected experimental conditions, thereby optimizing the reaction conditions for increasing the fraction of free carotenoids in the source of carotenoids in which at least some of the carotenoids are fatty acid esterified carotenoids via the esterase.

According to still another aspect of the present invention there is provided a method of increasing a fraction of free carotenoids in a source of carotenoids in which at least some of the carotenoids are fatty acid esterified carotenoids, the method comprising contacting the source of carotenoids with an effective amount of an esterase under conditions effective in deesterifying the fatty acid esterified carotenoids, thereby increasing the fraction of free carotenoids in the source of carotenoids.

According to yet another aspect of the present invention there is provided a method of increasing a fraction of free carotenoids in a source of carotenoids in which at least some of the carotenoids are fatty acid esterified carotenoids, the method comprising contacting the source of carotenoids with an effective amount of an esterase under conditions effective in deesterifying the fatty acid esterified carotenoids, wherein the conditions effective in deesterifying the fatty acid esterified carotenoids are characterized by addition of at least one additive selected from the group consisting of a cellulose degrading enzyme, a protein degrading enzyme, a pectin degrading enzyme, an emulsifier; and at least one metal ion, thereby increasing the fraction of free carotenoids in the source of carotenoids.

According to still another aspect of the present invention there is provided a method of increasing a fraction of free carotenoids in a source of carotenoids in which at least some of the carotenoids are fatty acid esterified carotenoids, the method comprising contacting the source of carotenoids with an effective amount of an esterase under conditions effective in deesterifying the fatty acid esterified carotenoids, so as to produce a source of at least partially deesterified carotenoids, and extracting said source of at least partially deesterified carotenoids with ethyl acetate under alkaline conditions, thereby increasing the fraction of free carotenoids in the source of carotenoids.

According to another aspect of the present invention there is provided a method of increasing a fraction of free carotenoids in a source of carotenoids in which at least some of the carotenoids are fatty acid esterified carotenoids, the method comprising contacting the source of carotenoids with an effective amount of an immobilized esterase under conditions effective in deesterifying the fatty acid esterified carotenoids, thereby increasing the fraction of free carotenoids in the source of carotenoids.

According to still another aspect of the present invention there is provided a method of increasing a fraction of free carotenoids in a source of carotenoids in which at least some of the carotenoids are fatty acid esterified carotenoids, the method comprising contacting the source of carotenoids with an effective amount of an esterase and a recycled emulsifier under conditions effective in deesterifying the fatty acid esterified carotenoids, thereby increasing the fraction of free carotenoids in the source of carotenoids.

According to yet another aspect of the present invention there is provided a method of reducing a fraction of Vitamin E in a source of carotenoids in which at least some of the carotenoids are fatty acid esterified carotenoids, the method comprising contacting the source of carotenoids with an effective amount of an esterase under conditions effective in deesterifying the fatty acid esterified carotenoids, so as to produce a source of at least partially deesterified carotenoids, and chromatographically extracting the fraction of Vitamin E away from said source of at least partially deesterified carotenoids, thereby reducing the fraction of Vitamin E in the source of carotenoids.

According to further features in preferred embodiments of the invention described below, the method further comprising extracting free carotenoids from the source of carotenoids.

According to an additional aspect of the present invention there is provided a source of carotenoids having an increased fraction of free carotenoids and produced by the method described herein.

According to an additional aspect of the present invention there is provided a food additive comprising the source of carotenoids having an increased fraction of free carotenoids as described herein.

According to an additional aspect of the present invention there is provided a feed additive comprising the source of carotenoids having an increased fraction of free carotenoids as described herein.

According to still another aspect of the present invention there is provided a composition of matter comprising enzymatically deesterified red carotenoids, the composition of matter characterized by at least about 40 percent by weight capsanthin, at least about 15 percent by weight zeaxanthin and capsolutein, at least about 2 percent by weight violaxanthin, at least about 1 percent by weight capsorubin, at least about 5 percent by weight beta cryptoxanthin and at least about 3 percent by weight beta carotene, and wherein said composition of matter is characterized by antioxidant activity, as measured by lipid oxidation.

According to further features in preferred embodiments of the invention described below, the source of carotenoids is characterized in that a majority of the carotenoids in the source of carotenoids are the fatty acid esterified carotenoids.

According to still further features in the described preferred embodiments the source of carotenoids is red pepper.

According to still further features in the described preferred embodiments the source of carotenoids is red pepper powder.

According to still further features in the described preferred embodiments the source of carotenoids is paprika.

According to still further features in the described preferred embodiments the source of carotenoids is red pepper oil extract.

According to still further features in the described preferred embodiments the source of carotenoids is red pepper oleoresin.

According to still further features in the described preferred embodiments the source of carotenoids is selected from the group consisting of apple, apricot, avocado, blood orange cape gooseberry, carambola, chilli, clementine, kumquat, loquat, mango, minneola, nectarine, orange, papaya, peach, persimmon, plum, potato, pumpkin, tangerine and zucchini. According to still further features in the described preferred embodiments the esterase is selected from the group consisting of a lipase, a carboxyl ester esterase and a chlorophylase, preferably a lipase.

According to still further features in the described preferred embodiments the lipase is selected from the group consisting of bacterial lipase, yeast lipase, mold lipase and animal lipase.

According to still further features in the described preferred embodiments the esterase is an immobilized esterase.

According to still further features in the described preferred embodiments the preselected experimental conditions, the different preselected experimental conditions and/or the conditions effective in deesterifying the fatty acid esterified carotenoids, comprise at least one of addition of a cellulose degrading enzyme; addition of a pectin degrading enzyme; addition of an emulsifier; and addition of at least one metal ion.

According to still further features in the described preferred embodiments the at least one metal ion is selected from the group consisting of $Ca^{++}$ and $Na^+$.

According to still further features in the described preferred embodiments the addition of the at least one metal ion is by addition of at least one salt of said metal ion.

According to still further features in the described preferred embodiments the at least one salt is selected from the group consisting of $CaCl_2$ and NaCl.

According to still further features in the described preferred embodiments the cellulose degrading enzyme is selected from the group consisting of Cl type beta-1,4 glucanase, exo-beta-1,4 glucanase, endo-beta-1,4 glucanase and beta-glucosidase.

According to still further features in the described preferred embodiments the proteins degrading enzyme is selected from the group consisting of tripsin, papain, chymotripsins, ficin, bromelin, cathepsins and rennin.

According to still further features in the described preferred embodiments the pectin degrading enzyme is selected from the group consisting of a pectin esterase, pectate lyase and a polygalacturonase.

According to still further features in the described preferred embodiments the emulsifier is a non-ester emulsifier. According to still further features in the described preferred embodiments the emulsifier is lecithin.

According to still further features in the described preferred embodiments the emulsifier is deoxycholate.

According to still further features in the described preferred embodiments the emulsifier is a non-ionic detergent, such as, but not limited to, polyoxyethylensorbitane monolaurate (TWEEN-20).

According to still further features in the described preferred embodiments the emulsifier is derived from bile, gum—Arabic or sodium salt of free fatty acids.

According to yet further features in the described preferred embodiments the emulsifier is a recycled emulsifier.

According to still further features in the described preferred embodiments the carotenoids detection assay is a chromatography assay.

According to still further features in the described preferred embodiments the chromatography assay is selected from the group consisting of thin layer chromatography and high performance liquid chromatography.

According to still another aspect of the present invention there is provided an article of manufacture comprising a packaging material and at least one antioxidant unit dosage, the antioxidant unit dosage comprising a composition of matter comprising at least about 40 percent by weight capsanthin, at least about 15 percent by weight zeaxanthin and capsolutein, at least about 2 percent by weight violaxanthin, at least about 1 percent by weight capsorubin, at least about 5 percent by weight beta cryptoxanthin, at least about 3 percent by weight beta carotene and at least 10 mg per gram Vitamin E and a pharmaceutically acceptable carrier in each single unit dosage, and wherein the packaging material comprises a label or package insert indicating that the composition of matter is for increasing antioxidant levels in a subject.

According to further features in the described preferred embodiments the article of manufacture of comprises about 20 mg per gram Vitamin E.

According to still further features in the described preferred embodiments the composition of matter further comprises a pharmaceutically acceptable excipient selected from the group consisting of carboxymethylcellulose, microcrystalline cellulose, starch, and modified starch.

According to yet further features in the described preferred embodiments the antioxidant unit dosage is designed for oral administration.

According to still further features in the described preferred embodiments the antioxidant unit dosage is selected from the group consisting of a tablet, a caplet, and a capsule.

According to further features in the described preferred embodiments the composition of matter is in the form of a liquid dosage form.

The present invention successfully addresses the shortcomings of the presently known configurations by providing methods of determining an efficiency of an esterase in increasing a fraction of free carotenoids in a source of carotenoids in which at least some of the carotenoids are fatty acid esterified carotenoids; screening for esterases efficient in increasing a fraction of free carotenoids in a source of carotenoids in which at least some of the carotenoids are fatty acid esterified carotenoids; optimizing reaction conditions for increasing a fraction of free carotenoids in a source of carotenoids in which at least some of the carotenoids are fatty acid esterified carotenoids, via an esterase; and increasing a fraction of free carotenoids in a source of carotenoids in which at least some of the carotenoids are fatty acid esterified carotenoids; and a source of carotenoids having an increased fraction of free carotenoids, which can serve as a food and/or feed additive; and a rich source from which one can extract to purification desired carotenoids.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice In the drawings:

FIG. 7a shows an HPLC chromatogram following extraction of oleoresin with freshly prepared immobilized lipase. FIGS. 7b and 7c show the HPLC chromatograms of fresh samples of oleoresin following extraction with recycled immobilized lipase collected by precipitation after use. Note the identity of HPLC profile using fresh immobilized lipase (FIG. 7a), once recycled immobilized lipase (FIG. 7b) and twice recycled immobilized lipase (FIG. 7c), indicating no significant loss of enzyme activity.

FIG. 9a shows an HPLC chromatogram following extraction of oleoresin with freshly prepared deoxycholate. FIGS. 9b to 9d show the HPLC chromatograms of fresh samples of oleoresin following extraction with recycled deoxycholate recycled by dehydration of the aqueous phase by lyophyllization or oven drying after use. Note the identity of HPLC profile using fresh deoxycholate (FIG. 9a), once recycled deoxycholate (FIG. 9b), twice recycled deoxycholate (FIG. 9c) and thrice recycled deoxycholate (FIG. 9d), indicating no significant loss, and an apparent increase, of emulsification activity with recycling.

FIG. 12 is a Table showing the superior stability of enzymatically deesterified paprika oleoresin, by maintenance of color in water. The absorbance at 474 nm (red color) of a paprika oleoresin emulsion prepared in water (1 mg/100 ml water) containing 0.15% or 0.03% Tween-20 detergent was measured spectrophotometrically. Note the superior color stability of the deesterified oleoresin in low detergent (0.03%) conditions, over 30 days storage.

FIG. 13a shows a chromatogram of enzymatically deesterified paprika oleoresin carotenoids extracted with hexane. FIG. 13b shows a chromatogram of enzymatically deesterified paprika oleoresin carotenoids extracted with with ethyl-acetate. FIG. 13c shows a chromatogram of enzymatically deesterified paprika oleoresin carotenoids extracted with ethyl acetate, with pH adjustment to pH 9.5, and FIG. 13d shows a chromatogram of enzymatically deesterified paprika oleoresin carotenoids extracted with ethyl acetate, without pH adjustment. 20 mg of paprika oleoresin containing 74 µg total carotenoids/mg oil was deesterified in the presence of lipase, deoxycholate and water by shaking for 24 hours at 37° C. Ethyl acetate or hexane extraction, as describe in Materials and Experimental Methods hereinbelow, was then performed, either with (FIG. 13c) or without (FIG. 13d) adjustment of pH to 9.5 with NaOH. Note the identity of all of the HPLC chromatograms.

FIGS. 14a and 14b are Tables showing the effect of pH adjustment on the efficiency of carotenoid and Vitamin E extraction following enzymatic deesterification. FIG. 14a compares the carotenoid composition following enzymatic deesterification of oleoresin, as described hereinabove, and alkaline treatment (pH adjustment) or no treatment (unadjusted). FIG. 14b compares the composition (mg/g oil) of extracted carotenoids by mass. Note both the enrichment of capsanthin, Vitamin E and other carotenoids by percent, and the greatly superior recovery of total carotenoids and Vitamin E (FIG. 14b) with alkaline treatment.

FIG. 17 is a Table showing the composition of enzymatically deesterified carotenoids containing Vitamin E and depleted of Vitamin E, in percentage composition (wt/wt).

DESCRIPTION OF THE PREFERRED EMBODIMENTS

Figure 1:
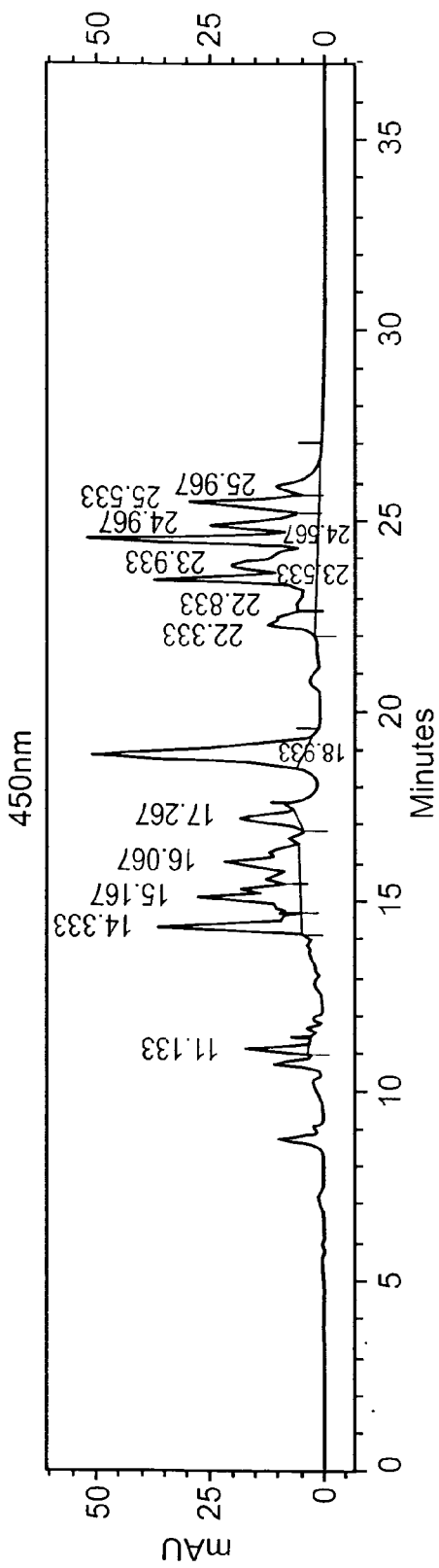
FIG. 1 is a HPLC chromatogram of natural red pepper carotenoids (obtained from oleoresin).

The present invention is of methods of (i) determining an efficiency of an esterase in increasing a fraction of free carotenoids in a source of carotenoids in which at least some of the carotenoids are fatty acid esterified carotenoids; (ii) screening for esterases efficient in increasing a fraction of free carotenoids in a source of carotenoids in which at least some of the carotenoids are fatty acid esterified carotenoids; (iii) optimizing reaction conditions for increasing a fraction of free carotenoids in a source of carotenoids in which at least some of the carotenoids are fatty acid esterified carotenoids, via an esterase; (iv) increasing a fraction of free carotenoids in a source of carotenoids in which at least some of the carotenoids are fatty acid esterified carotenoids; and (iv) an efficient method of extracting red pepper oleoresin. The present invention is further of a source of carotenoids having an increased fraction of free carotenoids, which can serve as a food and/or feed additive and as a rich source from which to extract to substantial purification desired carotenoids.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of extracting red pepper oleoresin. The red pepper fruit can be either fresh or frozen. The method is effected by homogenizing red-pepper fruits in water into a juice; centrifuging the juice so as to obtain a pellet; mixing the pellet (either directly or after freezing) with ethanol and ethyl acetate; homogenizing the pellet with the ethanol and the ethyl acetate; removing dry material; and evaporating solvents so as to obtain red pepper oleoresin.

As is further detailed and exemplified hereinbelow, esterified carotenoids can be deesterified from the pellet (directly or after freezing), or, preferably, from the oleoresin derived therefrom via extraction as descried above, by a lipase preferably in the presence of a cellulase and a pectinase.

Preferably, a weight ratio between the red-pepper fruits and the water is 80–120 parts of fruit to 20–60 parts of water. Still preferably, the juice is centrifuged at 20,000–30,000 g for 10–30 minutes. Yet preferably, the pellet is mixed with 1–3 parts of the ethanol and 5–15 parts of the ethyl acetate. Still preferably, removing the dry material is by centrifugation. Preferably, evaporating the solvents is at 40–50° C. and preferably under vacuum.

According to another aspect of the present invention there is provided a method of determining an efficiency of an esterase in increasing a fraction of free carotenoids in a source of carotenoids in which at least some of the carotenoids are fatty acid esterified carotenoids. The method according to this aspect of the present invention is effected by contacting the source of carotenoids with the esterase under preselected experimental conditions; and using a carotenoids detection assay for determining the efficiency of the esterase in increasing the fraction of the free carotenoids in the source of carotenoids.

According to still another aspect of the present invention there is provided a method of screening for esterases efficient in increasing a fraction of free carotenoids in a source of carotenoids in which at least some of the carotenoids are fatty acid esterified carotenoids. The method according to this aspect of the present invention is effected by contacting the source of carotenoids separately with each of the esterases under preselected experimental conditions; and using a carotenoids detection assay for determining the efficiency of each of the esterases in increasing the fraction of the free carotenoids in the source of carotenoids, thereby screening for esterases efficient in increasing the fraction of free carotenoids in the source of carotenoids.

According to yet another aspect of the present invention there is provided a method of optimizing reaction conditions for increasing a fraction of free carotenoids in a source of carotenoids in which at least some of the carotenoids are fatty acid esterified carotenoids, via an esterase. The method according to this aspect of the present invention is effected by contacting the source of carotenoids with the esterase under different preselected experimental conditions; and using a carotenoids detection assay for determining the efficiency of the esterase in increasing the fraction of the free carotenoids in the source of carotenoids under each of the different preselected experimental conditions, thereby optimizing the reaction conditions for increasing the fraction of free carotenoids in the source of carotenoids in which at least some of the carotenoids are fatty acid esterified carotenoids via the esterase.

Preferably, the carotenoids detection assay is a chromatography assay, such as, but not limited to, thin layer chromatography (TLC) and high performance liquid chromatography (HPLC). These assays are well known for, and are frequently used in the characterization of different carotenoids.

According to still another aspect of the present invention there is provided a method of increasing a fraction of free carotenoids in a source of carotenoids in which at least some of the carotenoids are fatty acid esterified carotenoids. The method according to this aspect of the present invention is effected by contacting the source of carotenoids with an effective amount of an esterase under conditions effective in deesterifying the fatty acid esterified carotenoids, thereby increasing the fraction of free carotenoids in the source of carotenoids. Once freed, individual non-esterified carotenoids or groups of similar non-esterified carotenoids can be extracted and purified to substantial homogeneity using methods well known in the art, such as, but not limited to, extraction with organic solvents followed by phase separation, various chromatographies, etc.

The source of carotenoids, rich in free, non-esterified carotenoids, produced by the method of the present invention, and/or the free carotenoids further purified therefrom can be used as food and/or feed additives in human or animal diet, to serve as natural antioxidants and/or food, animal and cosmetic natural colorants.

A preferred source of carotenoids according to the present invention is characterized in that a majority of the carotenoids in the source of carotenoids are fatty acid esterified carotenoids, such as, for example, red pepper derived carotenoids. Red pepper is one of the richest sources of carotenoids among vegetable crops. Most of the domesticated varieties of red pepper belong to the species *Capsicum annuum*; pepper breeding has focused and evolved mainly on the development of cultivars and varieties suited for use as a vegetable, spice condiment, ornamental or medicinal plant. Few studies have been devoted to the improvement of the chemical and nutritional composition of peppers (Bosland, 1993; Poulos, 1994). Capsanthin is the predominant carotenoid of the red pepper fruit and its content is controlled by major genes and polygenes; several genes have been identified along its biosynthetic pathway (Lefebvre, 1998).

Red pepper fruits, especially from paprika cultivars are used in the form of powders and oleoresins as food colorants. These products are very rich in carotenoids, some of them specific to pepper fruits. The keto carotenoid, capsanthin, occur only in red pepper, represents 50% the carotenoids in the vegetable and contribute to the red color. Zeaxanthin and lutein, $\beta$-carotene and $\beta$-cryptoxanthin are the additional carotenoids found in red pepper at concentrations of 20%, 10% and 5%, respectively (Levy et al., 1995). Capsanthin accounts for 30–60% of total carotenoids in fully ripe fruits. The capsanthin is esterified with fatty acids (nonesterified 20%; monoesterified 20–30%; diesterified 40–50%). The fatty acids of esterified capsanthins are chiefly lauric (12:0), myristic (14:0) and palmitic (16:0) acid. The bioavailability of fatty acids esterified carotenoids is, nevertheless, very low.

Other plant species that containing fatty acid esterified carotenoids, including, but not limited to, apple, apricot, avocado, blood orange cape gooseberry, carambola, chilli, clementine, kumquat, loquat, mango, minneola, nectarine, orange, papaya, peach, persimmon, plum, potato, pumpkin, tangerine and zucchini, can also be used as a source of carotenoids for the present invention. The esterified carotenoids content of these fruits are described in Dietmar E. Breithaupt and Ameneh Bamedi "Carotenoid ester in vegetables and fruits: A screening with emphasis on beta-cryptoxanthin esters" J. Agric. Food Chem. 2001, 49, 2064–2070, which is incorporated herein by reference.

Any type of esterase that can deesterify fatty acid esterified carotenoids can be used to implement the present invention. Methods for screening for most efficient esterases and suitable conditions for their activity with respect to different types of substrates (carotenoids sources) are also described herein. The esterase of choice can be, for example, a lipase, a carboxyl ester esterase or a chlorophylase, preferably a lipase. Enzymes species belonging to these families are known to deesterify a wide range of fatty acid esters, i.e., to have a wide range of substrate specificity. Different lipases can be used in the method of the present invention, including, for example, those obtained from bacterial, yeast or animal sources. The esterase used while implementing the methods of the present invention can be free in solution or, in order to improve the accessibility to the esterase and its re-use, it can be immobilized on various carrier materials. Methods for immobilization of esterases on solid matrices, their use in catalytic rections, recovery and reuse are described extensively in the literature (see, for example, U.S. patent application Ser. No. 5,902,738 to Orsat, et al., which is incorporated herein by reference). Briefly, the immobilization can be effected covalently or non-covalently, preferably non-covalently, by simple adsorption on a suitable carrier material having a large surface. Since esterase and carrier material are insoluble in organic solvents, no measurable desorption takes place during the reaction. Suitable carrier materials are many of the usual, inexpensive filter aids, adsorbents, ion exchangers and chromatography materials, such as Florisil.RTM., diatomaceous earth, bentonite, cellulose, molecular sieve, Amberlite.RTM., Amberlyst.RTM., silica gel or aluminum oxide and the like, as well as other inexpensive materials having large surface areas, such as sand, sintered glass or hollow fibres and the like. Alternatively, commercially available, already immobilized esterase preparations preparations can also be used, for example the lipase preparations from Meito Sangyo and Boehringer Mannheim GmbH: (Lipase PLC: Lipase PL immobilized on diatomaceous earth; Lipase PLG: Lipase PL immobilized on granulated diatomaceous earth; Lipase L-2 (Chirazyme.RTM. L-2, formerly Novozym.RTM. SP 435, Roche Diagnostics, GmbH, Mannheim, Germany): lipase from *Candida antarctica*, immobilized on macroporous polyacryl. In one preferred embodiment the immobilized lipase is *Candida rugosa* lipase immobilized on porous acrylic beads (Cat # L1150, Sigma Chemicals, St Louis Mo.).

If desired, the immobilization of the esterase can also be effected in the presence of a "cholanic salt" emulsifier (co-immobilization), by means of which the activity can in part be controlled (activator). Suitable cholanic salts are e.g. sodium cholate and sodium deoxycholate. As is further detailed below, an oil-in-water or preferably water-in-oil emulsion of the carotenoid source is prepared in order to enhance catalytic activity of the esterase employed. Other means to enhance enzyme activity can also be practiced, as described hereinbelow.

Figure 7A:
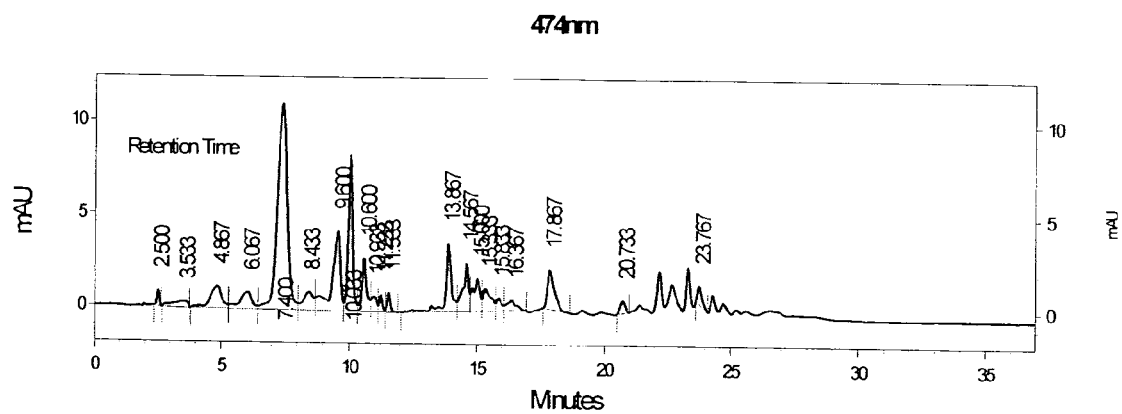
FIGS. 7a–7c are HPLC chromatograms of paprika oleoresin carotenoids extracted with fresh and recycled immobilized *Candida rugosa* lipase. 100 mg equivalent matrix-bound *C. rugosa* lipase was used to extract 20 mg of paprika oleoresin in the presence of deoxycholate and water by shaking for 24 hours at 37° C., followed by ethyl acetate extraction, as describe in Materials and Experimental Methods hereinbelow.
Figure 7B:
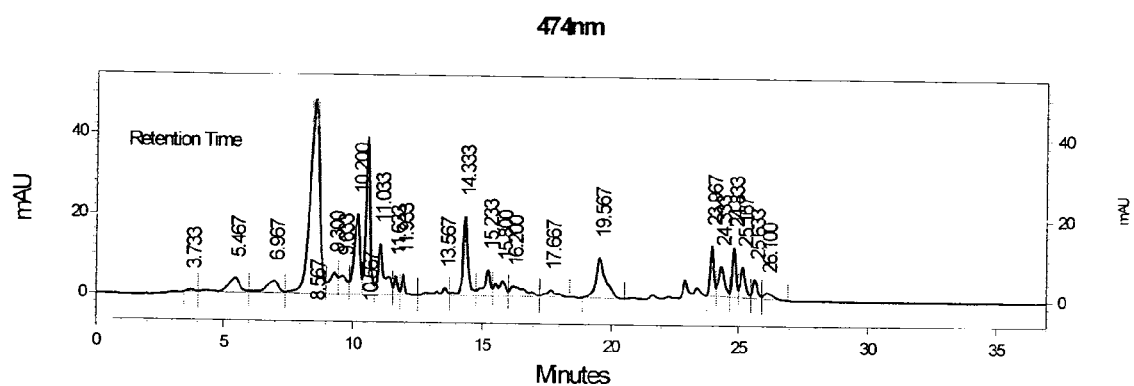
Figure 7C:
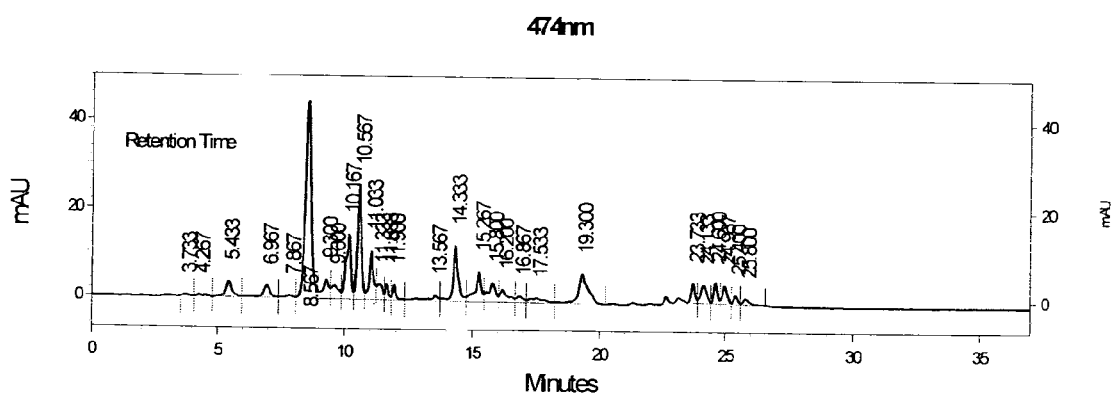

While reducing the present invention to practice, it was uncovered that matrix-bound, immobilized esterases can be recovered from the deesterification reaction mixture, and reused numerous times (see Example 5 hereinbelow). Surprisingly, deesterification efficiency, as measured by comparison of HPLC profiles of the resultant carotenoid fractions, was not significantly affected by using recycled, matrix-bound immobilized lipase (see FIGS. 7a–7c, hereinbelow), retaining greater than 95% original activity. The recovery and reuse of recycled lipase for deesterification of carotenoids is of great advantage not only for the improved simplicity and reduction of costs that it affords, but also for the greatly superior purity of effluent wastes from the deesterification process, which is of crucial environmental and ecological concern.

Thus, according to the present invention, there is provided a method of increasing a fraction of free carotenoids in a source of carotenoids in which at least some of the carotenoids are fatty acid esterifled carotenoids, the method comprising contacting the source of carotenoids with an effective amount of an immobilized esterase under conditions effective in deesterifying the fatty acid esterified carotenoids, thereby increasing the fraction of free carotenoids in the source of carotenoids.

According to one preferred embodiment, the immobilized esterase is selected from the group consisting of an immobilized lipase, an immobilized carboxyl ester esterase and an immobilized chlorophylase. In another, more preferred embodiment, the immobilized esterase is an immobilized lipase, for example, *Candida rugosa* lipase. The immobilized lipase can also be an immobilized bacterial lipase, immobilized yeast lipase, immobilized mold lipase and/or immobilized animal lipase. In a most preferred embodiment the immobilized lipase is a recycled immobilized lipase, as dscribed in detail hereinbelow.

It will be noted, that the deesterification processes for preparing enzymatically deesterified carotenoids may be carried out in batch mode, or in continuous flow cocurrent or counter-current mode. A continuous process can use a reactor containing enzyme catalyst, said reactor being a packed bed, fluidized bed or ebullating bed where the enzyme catalyst remains in the bed and reactants continuously flow through the bed. Batch and continuous processes may be carried out in a single deesterification step or multiple steps. The use of multiple steps permits use of lower enzyme oleoresin ratios in each step, but requires multiple separation steps. Single step batch or cocurrent continuous processes require relatively high ratios of enzyme to oleoresin in the initial reaction mixture, but are generally more economical than multi-step processes. Continuous flow reactors suitable for lipase reactions are described in detail in, for example, U.S. Pat. No. 5,288,619 to Brown et al., incorporated herein by reference.

Lipases typically catalyze the deesterification of triglycerides and diglycerides containing fatty acids bond to glycerol by ester bond. The carotenoids in, for example, paprika are esterified by fatty acids such as myristic, lauric, palmitic stearic, oleic and linoleic acids and for this reason they are different from triglycerides which are the natural substrates for lipases. Lipases are known to hydrolyze emulsified acyl lipids, as they are active on a water/lipid interface. For this reason, deoxycholate improves the reaction of the enzyme and its concentration is important to receive a high reactivity of the enzymes. Lipase catalyzed reactions are accelerated by $Ca^{2+}$ ions since the freed fatty acids are precipitated as insoluble Ca-salts. Introduction of $Ca^{2+}$ ions in the process described herein enhances deesterification.

Thus, according to preferred embodiments of the present invention, the preselected experimental conditions, the different preselected experimental conditions and/or the conditions effective in deesterifying the fatty acid esterified carotenoids, comprise, for example, the addition of a cellulose degrading enzyme; the addition of a proteins degrading enzyme; the addition of a pectin degrading enzyme; the addition of an emulsifier to the reaction mixture; and/or the addition of at least one metal ion to the reaction mixture, e.g., the addition of salts, such as $CaCl_2$ and/or NaCl. Other reaction conditions such as the addition of effectors, temperature, pH, etc., can also be optimized for each combination of enzyme and substrate.

The degrading enzymes used in context of the present invention serve to degrade their respective substrates present in the reaction mixture in order to avoid sequestering effects and reduce the viscosity of the reaction mixture.

The cellulose of choice can be a $C_1$ type beta-1,4 glucanase, exo-beta-1,4 glucanase, endo-beta-1,4 glucanase and/or beta-glucosidase from plant, insect or bacterial source. The proteins degrading enzyme can be, for example, tripsin, papain, chymotripsins, ficin, bromelin, cathepsins and/or rennin. The type and amount of the proteins degrading enzyme is controlled so as to avoid degradation of the esterase itself. The pectin degrading enzyme can, for example, be a pectinestrerase, pectate lyase and/or a polygalacturonase.

Careful attention should be given to the emulsifier of choice. Lipid esterases are water soluble and therefore reside in the water component of the emulsion, yet, their substrates reside in the oily portion of the emulsion. Presently preferred emulsifiers hence include lecithin, deoxycholate, gum Arabic (e.g., 0.5–2.0%), free fatty acid salts (e.g., 0.5–2.0%), bile derived emulsifiers and non-ionic detergents, such as, but not limited to, polyoxyethylensorbitane monolaurate (TWEEN-20). Preferably, the emulsifier employed is a non-ester emulsifier, as ester emulsifiers can adversely affect the reaction as competitive substrates or inhibitors of the esterase of choice. Suitable non-ester emulsifiers include, but are not limited to deoxycholate, gum Arabic (e.g., 0.5–2.0%) and free fatty acid salts (e.g., 0.5–2.0%).

While reducing the present invention to practice, it was uncovered that the effluent liquid phase remaining after removal of immobilized esterase and solvent extraction of the carotenoid fraction following the enzymatic deesterification reaction of the present invention, contained considerable amounts of deoxycholate which, when dried, was reusable. As described in detail hereinbelow (see Example 6), by collection and lyophilization or oven drying of the aqueous effluent from the extraction of carotenoids following enzymatic deesterification, sufficient deoxycholate was recovered to provide efficient emulsification in additional enzymatic deesterification reactions (see FIGS. 9a–9d hereinbelow). Reuse of the recovered, dried emulsifier is effected by reconstitution with water.

As is shown in FIGS. 9a–9d, and FIG. 10 hereinbelow, the efficiency of deesterification of oleoresin carotenoids is not compromised by using recycled deoxycholate. Indeed, an unexpected synergistic result was observed, wherein the deesterification efficiency actually increased with repeated recycling of the deoxycholate (see, for example, FIG. 10). Without wishing to be limited by a single hypothesis, it is postulated that the increased efficiency of deesterifiecation using recovered, reconstituted recycled emulsifier as described herein, can be the result of extraction of natural emulsifiers intrinsic to the starting carotenoid source.

As regarding the reuse of immobilized lipase, the recovery and reuse of recycled emulsifiers, such as deoxycholate, for deesterification of carotenoids is of great advantage not only for the improved simplicity and reduction of costs that it affords, but also for the greatly superior purity of effluent wastes from the deesterification process, which is of crucial environmental and ecological concern, especially where emulsifiers and detergents such as deoxycholate and Tween are involved (see, for example, the guidelines for handling of toxic and hazardous wastes in www.orcbs.msu.edu/newhazard/wastemanual).

Thus, according to the present invention there is provided a method of increasing a fraction of free carotenoids in a source of carotenoids in which at least some of the carotenoids are fatty acid esterified carotenoids, the method comprising contacting the source of carotenoids with an effective amount of an esterase and a recycled emulsifier under conditions effective in deesterifying the fatty acid esterified carotenoids, thereby increasing the fraction of free carotenoids in the source of carotenoids.

In one preferred embodiment, emulsifier is a non-ester emulsifier, such as lecithin, deoxycholate and/or a non-ionic detergent. In yet another embodiment, the emulsifier is derived from bile, gum Arabic or salt of free fatty acids.

It will be appreciated, in the context of the present invention, that traditional extraction processes for the manufacture of concentrated extracts (concentrated several fold as compared with the raw material) involve not only the use of various non-edible solvent systems, but also a large proportion of solvent in relation to the compounds of interest, which must be eliminated from the finished extracts. The last traces of undesirable non-edible solvents are very difficult to separate from the concentrated extract, limiting the potential use of the residual solid for human consumption, and contributing to environmental contamination. Methods relying on high pressure and countercurrent extraction for production of highly concentrated carotenoid extracts have been disclosed (see, for example, U.S. Pat. No. 5,773,075 to Todd, and U.S. Pat. No. 5,789,647 to Heidlas et al), however, they require expensive equipment, involve undesirable temperatures, and are difficult to control.

As described hereinbelow, enzymatically deesterified red pepper oleoresin can be extracted with a non-polar solvent, such as hexane, chloroform, carbon tetrachloride, etc. While reducing the present invention to practice, it was surprisingly uncovered that extraction of the enzymatically deesterified carotenoids with a more polar solvent under mild alkaline conditions provided greatly enhanced efficiency, allowing for previously unattainable concentration and purity of the deesterified carotenoid fraction.

Figure 13A:
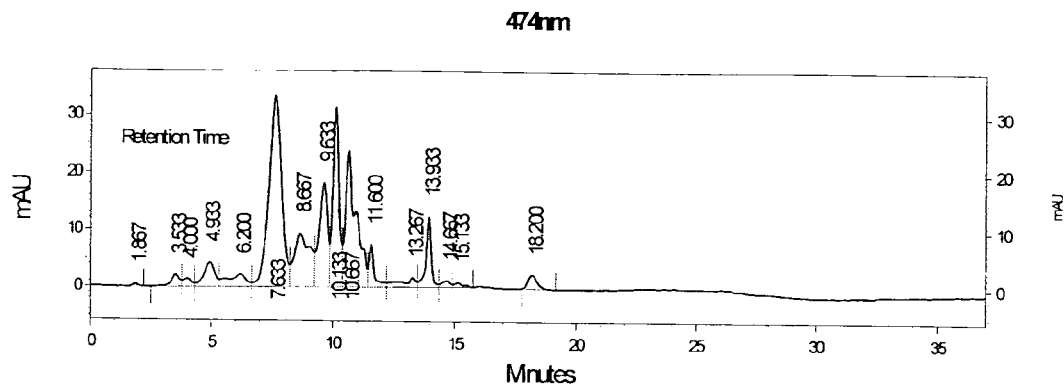
FIGS. 13a–13d are HPLC chromatograms of enzymatically deesterified paprika oleoresin carotenoids extracted under different conditions.

As described in Example 7 hereinbelow, addition of base to make the extraction mixture mildly alkaline, and extraction with a polar solvent such as ethyl acetate, chloroform, etc., results in unexpectedly highly concentrated deesterified red pepper oleoresin oil, comprising exceedingly desirable proportions of deesterified carotenoids. As shown in HPLC chromatograms of FIGS. 13a–13b, ethyl acetate extraction (FIG. 13b) of the enzymatically deesterified red pepper oleoresin results in a concentrated product having a profile of deesterified carotenoids equal to that produced with hexane extraction (FIG. 13a). The volume of the polar solvent (ethyl acetate) required for extraction is significantly less than that for the hexane (3–4 ml/5 ml deesterification reaction vs 7–8 ml/5 ml deesterification reaction). Comparison between the HPLC profiles from ethyl acetate extraction with (FIG. 13b) and without (FIG. 13a) mild alkaline pH adjustment of the extraction mixture reveals similarly efficient separation between the deesterified carotenoids, and their mom- and di-ester forms.

However, comparison of the carotenoid composition (FIGS. 14a and 14b) reveals that extraction with a more polar solvent, under mild alkaline conditions, greatly enriches the carotenoid and Vitamin E content of the resulting deesterified red pepper carotenoid extract. Whereas ethyl acetate extraction without pH adjustment actually reduces the carotenoid concentration (FIG. 14b), mild alkaline conditions improve the efficiency and purity of the extracted carotenoids, immensely (FIG. 14b). It will be noted that Vitamin E concentrations are enhanced even more significantly by mild alkaline ethyl acetate extraction.

Thus, according to the present invention there is provided a method of increasing a fraction of free carotenoids in a source of carotenoids in which at least some of the carotenoids are fatty acid esterified carotenoids, the method comprising contacting the source of carotenoids with an effective amount of an esterase under conditions effective in deesterifying the fatty acid esterified carotenoids, so as to produce a source of at least partially deesterified carotenoids, and extracting the source of at least partially deesterified carotenoids with ethyl acetate under alkaline conditions, thereby increasing the fraction of free carotenoids in the source of carotenoids.

In one preferred embodiment, the alkaline conditions are characterized by pH from about 8.0 to about 10, most preferrably pH 9.5. Further, it will be noted that polar solvents such as alcohols, chloroform, dimethyl chloride, etc can be used in the mild alkaline extraction of the enzymatically deesterified carotenoids. Extraction and washing procedure is described in detail in the Materials and Experimental Procedures section hereinbelow.

It will be noted that the aqueous fraction of the mild alkaline extraction described hereinabove, comprising the free fatty acids released in the deesterification of the carotenoids, can be collected, acidified, and re-extracted with a solvent such as methyl acetate, and concentrated by evaporation. The resulting concentrated source of natural free fatty acids from red pepper oleoresin can be used, for example, as a food additive, a feed additive, or in cosmetic and/or pharmaceutical compositions.

Figure 15A:
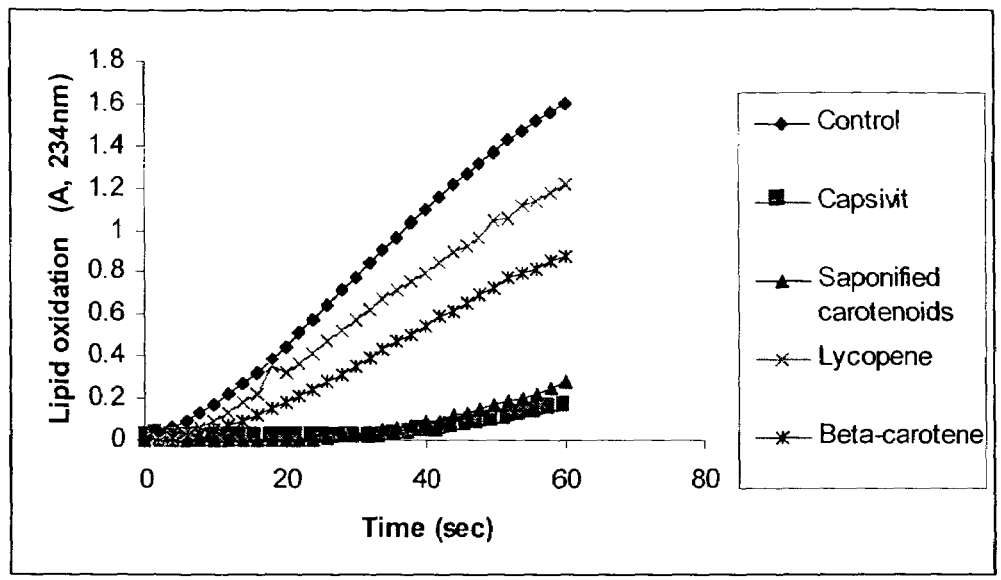
FIGS. 15a and 15b are graphs of inhibition of lipid oxidation, showing the superior antioxidant properties of enzymatically deesterified carotenoids. Lipid oxidation (assayed by met-myoglobin-catalyzed diene conjugation) was measured spectrophotometrically over time. Antioxidant activity of enzymatically deesterified carotenoids (40 µM concentration) containing Vitamin E (Capsivit, closed squares) and lacking Vitamin E (Saponified carotenoids, closed triangles), was compared with that of 40 µM lycopene (x) and beta-carotene (stars). Controls indicate the extent of lipid oxidation without added antioxidants (closed diamonds). Note the superior inhibition of lipid oxidation with enzymatically deesterified carotenoids containing Vitamin E (Capsivit, closed squares) and lacking Vitamin E (Saponified carotenoids, closed triangles), at both blood pH (pH 7.0, FIG. 15a), and stomach acid pH (pH 3, FIG. 15b).
Figure 15B:
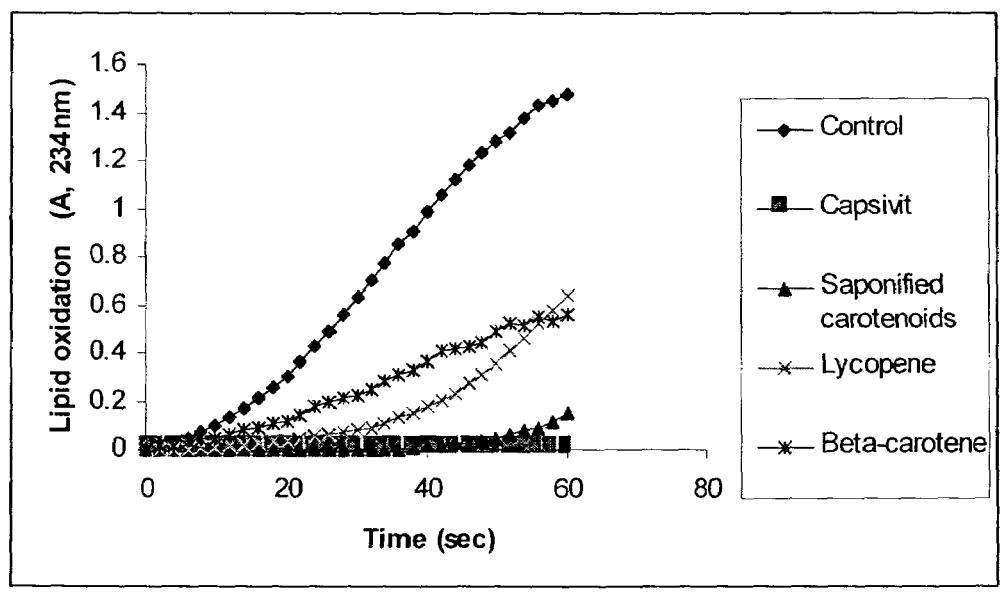

The resultant source of carotenoids highly enriched in deesterified carotenoids and Vitamin E is a superior source of antioxidants (see, for example, FIG. 14). As shown in Example 8 hereinbelow, enzymatically deesterified red pepper oleoresin inhibited lipid oxidation with significantly greater efficiency than other well known carotenoid antioxidants lycopene and beta carotene (see FIGS. 16a and 16b). Further, the novel enzymatically deesterified carotenoid composition described herein exhibits superior antioxidant properties at a variety of pH ranges, similar to those characteristic of different physiological conditions. Thus, at neutral pH, similar to blood and most tissue environments, deesterified carotenoid inhibited lipid oxidation 2–4 fold better than beta-carotene or lycopene, respectively, at 40 μM antioxidant (FIGS. 15a and 16a), and at highly acidic pH, such as in digestion in the stomach, 1–2 fold better, than lycopene or beta-carotene, respectively (FIGS. 15b and 16b).

Thus, according to the present invention there is provided a composition of matter comprising enzymatically deesterified red carotenoids, the composition of matter characterized by at least about 40 percent by weight capsanthin, at least about 15 percent by weight zeaxanthin and capsolutein, at least about 2 percent by weight violaxanthin, at least about 1 percent by weight capsorubin, at least about 5 percent by weight beta cryptoxanthin and at least about 3 percent by weight beta carotene, the composition characterized by antioxidant activity, as measured by lipid oxidation. The source of red carotenoids can be, as detailed above, red pepper carotenoids, paprika oleoresin, red pepper or paprika powder, etc.

As used herein in the specification and in the claims section below, the term "inhibit" and its derivatives refers to suppress or restrain from free expression of activity.

As defined herein in the specification and in the claims section below, the term "about" refers to a value within 0.15 times greater or lesser than the indicated value.

Figure 11A:
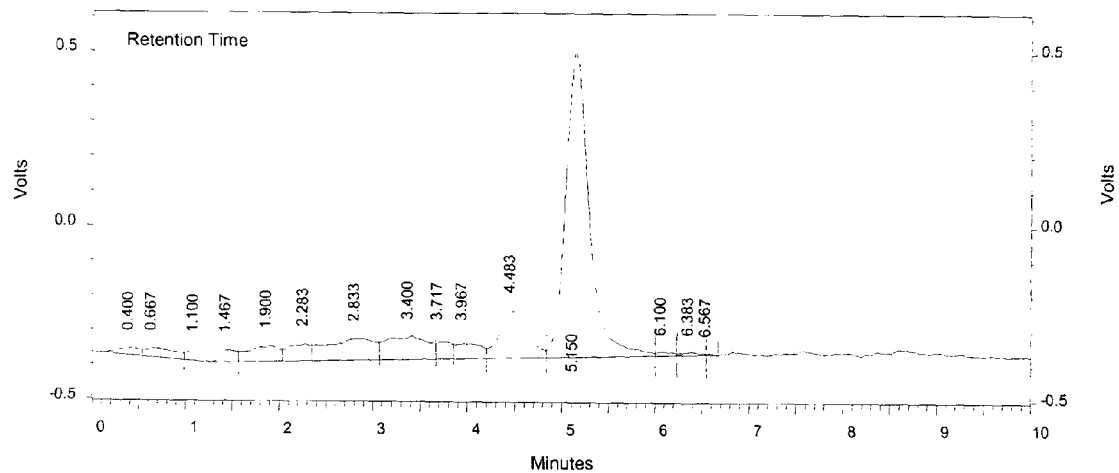
FIGS. 11a and 11b are HPLC chromatograms of de-esterified Paprika oil showing effective Vitamin E removal by Flurasil column. Deesterified Paprika oil, rich in Vitamin E (retention time=5.1 minutes, FIG. 11a) was separated on a Florisil column equilibrated with hexane and washed with hexane to remove yellow carotenoids. Red carotenoids (xanthophylls) were eluted with ethyl acetate, and analyzed on HPLC (FIG. 11b). Note the greater than 40 fold reduction in Vitamin E content of the red carotenoids after Flurasil purification (FIG. 11b, 5.1 minutes retention time).
Figure 11B:
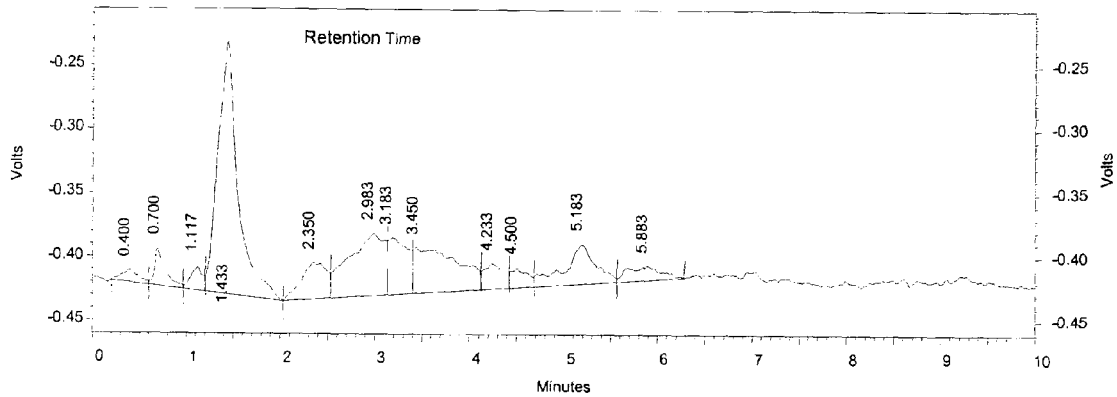

The composition of matter can comprise, or be depleted of, Vitamin E. In one preferred embodiment, the composition of matter comprises at least 5 mg per gram, most preferably 20 mg per gram Vitamin E. Depletion of Vitamin E is effected by passage of the enzymatically deesterified carotenoid preparation, following extraction, over a column of magnesium silicate, as described in Example 8 hereinbelow. Vitamin E is eluted with hexane, while the enriched fraction of deesterified carotenoids remains bound, and can be eluted with further washings with ethyl acetate (See FIGS. 11a and 11b).

Thus, according to one aspect of the present invention there is provided a method of reducing a fraction of Vitamin E in a source of carotenoids in which at least some of the carotenoids are fatty acid esterified carotenoids, the method comprising contacting the source of carotenoids with an effective amount of an esterase under conditions effective in deesterifying the fatty acid esterified carotenoids, so as to produce a source of at least partially deesterified carotenoids, and chromatographically extracting the fraction of Vitamin E away from said source of at least partially deesterified carotenoids, thereby reducing the fraction of Vitamin E in the source of carotenoids.

Similarly, there is provided a food additive and/or a feed additive comprising the composition of matter.

As defined herein in the specification and in the claims section below, the phrase "chromatographically extracting" is defined as separation of a fraction or fractions from other components of a material as a result of differential distribution of solutes as they flow around or over a stationary liquid or solid phase. Well known examples of chromatography include, but are not limited to liquid chromatography, gas chromatography, gas-liquid chromatography, affinity chromatography, paper chromatography, HPLC, etc. In one embodiment, chromatographically extracting the fraction comprises contacting the source of at least partially deesterified carotenoids with a magnesium silicate resin, washing with hexane, and eluting the at least partially deesterified carotenoids with ethyl acetate. In another, more preferred embodiment, the magnesium silicate resin is Florisil (Supelco, Bellefonte, Pa.).

As described in detail in the Background section hereinabove, dietary carotenoid intake has been inversely correlated with the incidence and severity of a number of diseases and conditions, such as cancer, cardiovascular disease, age related degeneration, arthritis, etc., due to the highly efficient antioxidant activity of carotenoids. Thus, carotenoids, which are widely distributed in nature, are natural dietary components, and are well tolerated by human digestion, are in great demand as nutritional supplements, food additives, feed additives, and therapeutic compositions (Hamilton Clin J Oncol Nurs 2001;5:181–2; Brown et al. Clin Excell Nurs Prac 998; 2:10–22). The antioxidant properties and bioavailability of the red carotenoids in the novel enzymatically deesterified carotenoid composition of the present invention clearly surpass those of previously available compositions. For example, a popular antioxidant supplement provides 5,712 mcg. beta carotene, 180 mcg. alpha carotene, 36 mcg. zeaxanthin, 44 mcg. cryptoxanthin, 28 mcg lutein., 100 i.u (150 mg) d-alpha tocopherol succinate (natural vitamin E) (taken twice to four times daily) (AntiOxidant Formula, Pure Encapsulations, Sudbury, Mass.), the carotenoids being in native, mostly esterified form. In sharp contrast, 1 gram of the enzymatically deesterified composition of the present invention comprises nearly 800 times as much zeaxanthin and capsolutein and twice as much beta carotene (FIG. 14b), having enhanced bioavailability in the deesterified form. Vitamin E content of 1 gram of the enzymatically deesterified composition alone is greater than the RDA of 15 mg (10 I.U.)/day (Dietary Ref Intakes for Vitamin C, Vitamin E, Selenium and Carotenoids, Institute of Medicine, 2000; 325–382, Nat'l Academies Press).

Thus, according to another aspect of the present invention there is provided an article of manufacture comprising a packaging material and at least one antioxidant unit dosage, the antioxidant unit dosage comprising a composition of matter comprising at least about 40 percent by weight capsanthin, at least about 15 percent by weight zeaxanthin and capsolutein, at least about 2 percent by weight violaxanthin, at least about 1 percent by weight capsorubin, at least about 5 percent by weight beta cryptoxanthin, at least about 3 percent by weight beta carotene and at least 20 mg per gram Vitamin E and a pharmaceutically acceptable carrier in each single unit dosage. The packaging material comprises a label or package insert indicating that the composition of matter is for increasing antioxidant levels in a subject.

In one preferred embodiment, the composition of matter further comprises a pharmaceutically acceptable excipient selected from the group consisting of carboxymethylcellulose, microcrystalline cellulose, starch, and modified starch.

In another preferred embodiment, the antioxidant unit dosage is designed for oral administration. The antioxidant unit dosage can be selected from the group consisting of a tablet, a caplet and a capsule. The composition of matter can be in liquid dosage form.

The enzymatically deesterified carotenoids of the present invention can be used to produce an antioxidant unit dosage. As used herein a "antioxidant unit dosage" refers to a preparation of one or more of the active ingredients described herein, either carotenoids or physiologically acceptable salts or prodrugs thereof, with other chemical components such as traditional drugs, physiologically suitable carriers and excipients. The purpose of an antioxidant unit dosage is to facilitate administration of antioxidants to a cell or to an organism. Antioxidant unit dosage of the present invention may be manufactured by processes well known in the art, e.g., by means of conventional mixing, dissolving, granulating, dragee-making, levigating, emulsifying, encapsulating, entrapping or lyophilizing processes.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Hereinafter, the phrases "physiologically suitable carrier" and "pharmaceutically acceptable carrier" are interchangeably used and refer to a an approved carrier or a diluent that does not cause significant irritation to an organism and does not abrogate the biological activity and properties of the administered conjugate.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should be suitable for the mode of administration.

Herein the term "excipient" refers to an inert substance added to a pharmaceutical composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols.

Further techniques for formulation and administration of active ingredients may be found in "Remington's Pharmaceutical Sciences," Mack Publishing Co., Easton, Pa., latest edition, which is incorporated herein by reference as if fully set forth herein.

Various routes for the administration of active ingredients are possible, and were previously described, for the purpose of the present invention. The topical carrier is one, which is generally suited for topical active ingredients administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. It is essential, clearly, that the selected carrier does not adversely affect the active agent or other components of the topical formulation, and which is stable with respect to all components of the topical formulation. Preferred water-soluble ointment bases are prepared from polyethylene glycols of varying molecular weight; again, reference may be made to Remington: The Science and Practice of Pharmacy for further information.

Gel formulations are preferred for application to the scalp. As will be appreciated by those working in the field of topical active ingredients formulation, gels are semisolid, suspension-type systems.

Various additives, known to those skilled in the art, may be included in the topical formulations of the invention. For example, solvents may be used to solubilize certain active ingredients substances. Other optional additives include skin permeation enhancers, opacifiers, anti-oxidants, gelling agents, thickening agents, stabilizers, and the like.

Other agents may also be added, such as antimicrobial agents, antifungal agents, antibiotics and anti-inflammatory agents.

Other components, which may be present, include preservatives, stabilizers, surfactants, and the like.

The antioxidant unit dosage herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Other suitable routes of administration may, for example, include oral, rectal, transmucosal, transdermal, intestinal or parenteral delivery, including intramuscular, subcutaneous and intramedullary injections as well as intrathecal, direct intraventricular, intravenous, inrtaperitoneal, intranasal, or intraocular injections.

Compositions of matter for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological saline buffer. For transmucosal administration, penetrants are used in the formulation. Such penetrants are generally known in the art.

For oral administration, the active ingredients can be formulated readily by combining the active ingredients with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The compositions of matter of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The compositions of matter described herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Determination of a therapeutically effective amount is well within the capability of those skilled in the art, especially in light of the detailed disclosure provided herein.

For any active ingredient used in the methods of the invention, the therapeutically effective amount or dose can be estimated initially from activity assays in animals. For example, a dose can be formulated in animal models to achieve a circulating concentration range that includes the $IC_{50}$ as determined by activity assays. Such information can be used to more accurately determine useful doses in humans. In general, dosage is from about 0.01 micrograms to about 100 g per kg of body weight, and may be given once or more daily, weekly, monthly or yearly, or even once every 2 to 20 years.

Toxicity and therapeutic efficacy of the active ingredients described herein can be determined by standard pharmaceutical procedures in experimental animals, e.g., by determining the $IC_{50}$ and the $LD_{50}$ (lethal dose causing death in 50% of the tested animals) for a subject active ingredient. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active moiety which are sufficient to maintain the modulating effects, termed the minimal effective concentration (MEC). The MEC will vary for each preparation, but can be estimated from in vitro data; e.g., the concentration necessary to achieve 50–100% inhibition of lipid oxidation may be ascertained using the assays described herein. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10–90% of the time, preferable between 30–90% and most preferably 50–90%.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions of the invention formulated in a compatible pharmaceutical carrier may also be prepared, placed in an appropriate container, and labeled for treatment of an indicated condition.

The present invention further provides methods of (i) determining an efficiency of an esterase in increasing a fraction of free carotenoids in a source of carotenoids in which at least some of the carotenoids are fatty acid esterified carotenoids; (ii) screening for esterases efficient in increasing a fraction of free carotenoids in a source of carotenoids in which at least some of the carotenoids are fatty acid esterified carotenoids; (iii) optimizing reaction conditions for increasing a fraction of free carotenoids in a source of carotenoids in which at least some of the carotenoids are fatty acid esterified carotenoids, via an esterase; and (iv) increasing a fraction of free carotenoids in a source of carotenoids in which at least some of the carotenoids are fatty acid esterified carotenoids. The present invention further provide a source of carotenoids having an increased fraction of free carotenoids, which can serve as a food and/or feed additive; and a rich source from which one can extract to purification desired carotenoids.

The present invention offers a great advantage over processes for chemical deesterification of carotenoids. For example, alkaline treatment of paprika affects to a great extent the properties of its proteins and antioxidants such as vitamin C and E. It will be appreciated that during heating of paprika to high temperatures, as required in alkaline based deesterification of carotenoids, one or more of the following adverse reactions takes place: (i) destruction of essential amino acids; (ii) conversion of natural amino acids into derivatives which are not metabolized; (iii) decrease of the digestibility of proteins as a result of cross-linking; and, last, but not least, generation of cytotoxic compounds. It will be appreciated in this respect that due to the formation, at high pH values, of enolates, phenolic compounds, including vitamin E and most of the other antioxidants are more rapidly oxidized, in a process that generates free radicals which oxidize and destroy carotenoids (Belitz and Grosch W. Food Chemistry, Springer-Verlag, 1987).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animal Cells—A Manual of Basic Technique"by Freshney, Wiley-Liss, N.Y. (1994), Third Edition; "Current Protocols in Immunology"Volumes I–III Coligan J. E., ed. (1994); Stites et al. (eds), "Basic and Clinical Immunology"(8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis"Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND EXPERIMENTAL PROCEDURES

Materials:

Paprika powder and oleoresin paprika were purchased from Tavlinei-Hanegev, Avshalom. Sodium phosphate, citric acid, TWEEN-20 (polyoxyethylensorbitane monolaurate) and potassium hydroxide were obtained from Merck (Darmstadt, Germany). Deoxycholic acid (sodium salt) BHT (Butylated hydroxy toluene), pancreatic lipase from porcine were obtained from Sigma Chemical Co. (St. Louis, Mo.). The enzymes, lipase A "Amano 6", lipase F-AP15 and lipase AY "Amano 30" (approved for human consumption) were from Amano, Pharmaceuticals Co. LTD (Nishiki, Japan). *Candida rugosa* lipase immobilized on porous acrylic beads was from Sigma (Cat #L1150, Sigma Chemical Co., St Louis Mo.). Pectinase/cellulase, Rohameut Max and protease (Coralase PN-L) were obtained from Rohm Enzyme gmbh (Darmstadt, Germany). HPLC grade ethanol and hexane were from Biolab (Israel) and HPLC acetone from Baker (Deventer, Holland). Ethyl acetate was from BioLab (Israel).

High-Performance Liquid Chromatography (HPLC):

HPLC was conducted on a Shimadzu LC-10 AT equipped with SCL-10A Shimadzu diode array detector. Photodiode array measurements of spectral properties from the individual peaks (from 260 to 540 nm) were determined at the upslope, apex and downslope. The column (Merck RP-18e 3.4×250 mM, 5-μm particles) was used for HPLC separations. The peaks were detected at 450 and 474 nm. The mobile phase were acetone and $H_2O$ with a gradient as suggested by Minguez-Mosquera et al. 1993 (J. Agric. Food Chem. 41, 1616–1620).

Deesterification of Paprika Powder by Enzymes:

Paprika powder (500 mg) was suspended in 9.5 ml water in the presence of Cellulase-Pectinase (100 μl), Lipase (100 mg) and 0.2% deoxycholate (200 mg) at pH 4.93. The suspension was shaken in a heated bath at 37° C. for 24 hours. Carotenoids were extracted from the suspension by addition of ethanol (5 ml) and 5 ml of hexane. The extraction with hexane was done repeatedly until no color could be observed in the extracts.

Deesterification of Paprika Oleoresin by Enzymes:

Paprika oleoresin (20 mg) was mixed with TWEEN-20 (200 μl) or deoxycholate (100 mg) and 10 ml of $H_2O$. The emulsion has been shaken at 37° C. for 24 hours. Extraction of carotenoids was performed by the addition of 4 ml of ethanol and 5 ml of hexane. The extraction with hexane was done repeatedly until no color could be observed in the extracts. The combined hexane extracts were washed with water (25 ml) and dried over anhydrous sodium sulfate for HPLC determination of the carotenoids.

Chemical Deesterification (Chemical Saponification):

Chemical deesterification was performed essentially as described in Ittah et al., J. Agric. Food Chem. 1993, 41, 899–901.

Immobilized Lipase and Recycling:

Immobilized lipase from *Candida rugosa* (Sigma-Aldrich Corp., St Louis, Mo.). Following use in deesterification, the enzyme-bearing beads are recovered by precipitation at 15 K RPM, and stored at 4° C. until reuse.

Recovery and Reconstitution of Deoxycholate:

Deoxycholate was recovered from the pooled aqueous phase of the ethyl acetate extraction by freeze drying (Ilshin Laboratories) or oven drying at 95° C. Briefly, following carotenoid extraction from the deesterified solution, the aqueous phase is collected and dried to a powder. The recovered deoxycholate was reconstituted with water before reuse in enzymatic deesterification. Reconstituted deoxycholate can be reused at least 3 times.

Ethyl Acetate Extraction of Deesterified Carotenoids:

Following deesterification with lipase, the carotenoid fraction was extracted by ethyl acetate, under alkaline pH. First, the lipase reaction mixture was made alkaline with NaOH, to pH 9.5 (with 0.1N NaOH solution) to convert the free fatty acids products to water soluble salts. Ethyl acetate was then added at a ratio of 1 volume ethyl acetate to 5 volumes aqueous deesterification mixture, the phases mixed and allowed to separate. The aqueous phase was removed, the ethyl acetate phase reextracted four times with distilled water (water:ethyl acetate=4:1 volume/volume), followed by drying by addition of superfluous sodium sulfate. Ethyl acetate solvent was then evaporated under vacuum in a Rotovapor (Buchi), to produce paprika oleoresin enriched in free carotenoids. Free fatty acids in the aqueous phase are quantitatively recovered by acidification and extraction with a non-polar solvent such as methyl acetate.

Vitamin E Separation from Deesterified Paprika Oleoresin:

Vitamin E was removed chromatographically from paprika oleoresin by passage though a magnesium-silicate absorbent column (Florisil, Supelco, Bellefonte, Pa.). A 30 cm×1 cm column of Florisil was equilibrated with hexane, and the paprika oleoresin applied to the column (0.5 ml paprika oil diluted with 0.5 ml ethanol at room temperature). The column was then flushed with hexane (flow rate 1 ml/min), until the carotene carotenoids (yellow color) were eluted. The retained carotenoids, including the xanthophylls (capsanthin), were then eluted from the column by extensive washing with ethyl acetate.

Stability of Deesterified Oleoresin in Water:

Stability of paprika oleoresin before and after enzymatic deesterification was assessed spectrophotometrically in a water emulsion containing 0.15% or 0.03% Tween-20 (polyoxyethylene sorbitan monolaurate, Amersham Biosciences Inc, Piscataway, N.J., USA), stored at 4° C. Clarity, as color concentration, was measured in deesterified and untreated oleoresin by visible range spectrophotometry, as absorbance (ΔOD) at 474 nm (red), after subtraction of background at 600–800 nm, in samples removed every 10 days for measurement of color concentration.

Lipid Oxidation Inhibition Assay:

Antioxidant activity was measured by inhibition of metmyoglobin catalyzed lipid oxidation, as changes in diene conjugated products detected at 234 nm. Carotenoids (enzymatically deesterified oleoresin, Vitamin E depleted enzymatically deesterified oleoresin, lycopene, and beta-carotene) were added to concentrations of 10, 20 or 40 µM, as indicated herein, and results compared with oxidation of lipids in control reactions having no added inhibitors, under neutral (pH 7.0) and highly acidic (pH 3.0) conditions.

EXPERIMENTAL RESULTS

Example 1

Efficient Enzymatic Deesterification of Red Pepper Caritenoids

As described hereinabove, carotenoids, although of significant importance to human nutritional and health, are poorly absorbed from natural sources due to the abundance of the mono-, di-, and triesterified forms. Currently, chemical saponification is used for deesterification, but is both costly and harsh to the resulting carotenoids. In an effort to provide a gentle, more efficient method of deesterification of natural carotenoids, red pepper extracts were reacted with lipases and the resultant carotenoids analyzed by HPLC.

FIG. 1 demonstrates a chromatogram of HPLC fractionation of natural red pepper (paprika) carotenoids. The main carotenoid is capsanthin. The free unesterified capsanthin was eluted at about 9 min. Most of the capsanthin is esterified as monoesters and diesters. The mono esters were eluted in three major peaks after β-cryptoxanthin (14.33 min) and before β-carotene (18.9 min). The diesters were eluted as 7 major peaks between 22–26 min.

Figure 2:
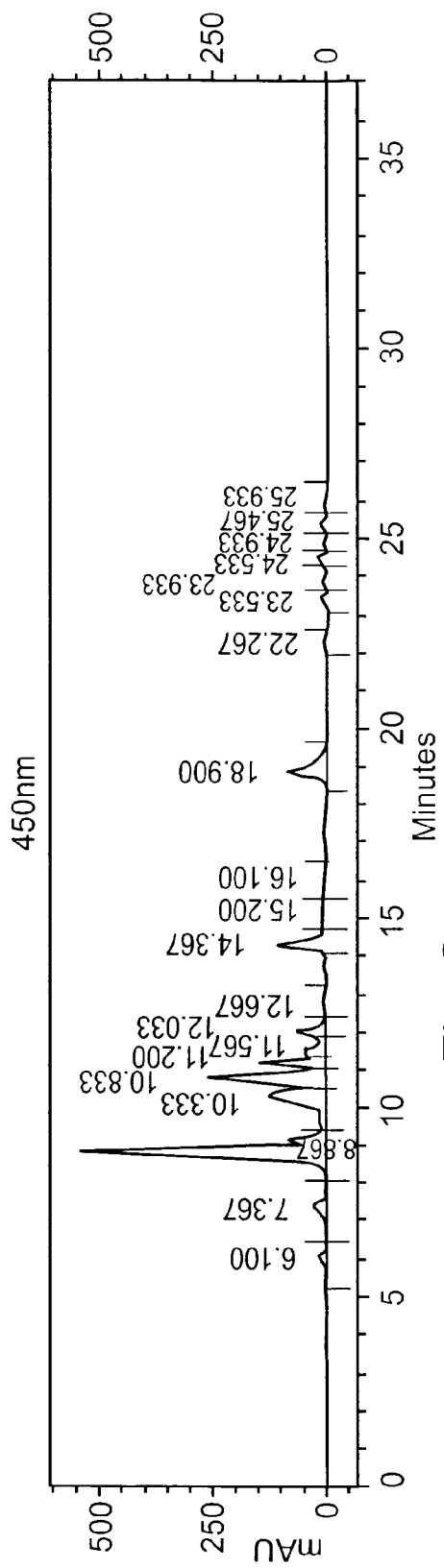
FIG. 2 is a HPLC chromatogram of natural red pepper (paprika) carotenoids following chemical saponification, the chromatogram contains mostly about 9 peaks of: (i) capsanthin (6.1 min); (ii) violaxanthin (7.36 min); (iii) capsanthin (8.89 min); (iv) cis-capsanthin (10.33); (v) capsolutein (10.83 min); (vi) Zeaxanthin (11.2 min); (vii) cis-Zeaxanthin (12.0 min); (viii) $\beta$-crypotxanthin (14.36 min); and (ix) $\beta$-carotene.

FIG. 2 demonstrates that following chemical saponification all the peaks of red pepper (paprika) diesters and monoesters carotenoids disappeared and the chromatogram contains mostly about 9 peaks of: (i) capsanthin (6.1 min); (ii) violaxanthin (7.36 min); (iii) capsanthin (8.89 min); (iv) cis-capsanthin (10.33); (v) capsolutein (10.83 min); (vi) Zeaxanthin (11.2 min); (vii) cis-Zeaxanthin (12.0 min); (viii) β-crypotxanthin (14.36 min); and (ix) β-carotene. The disadvantages of chemical saponification are discussed hereinabove.

Figure 3:
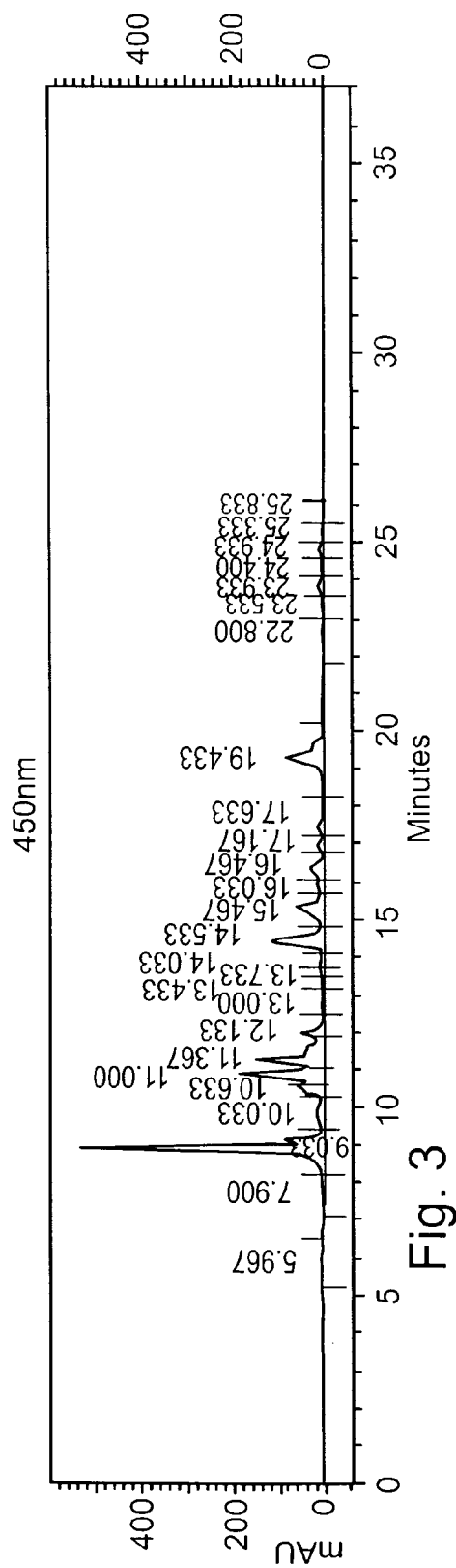
FIG. 3 is a HPLC chromatogram of natural red pepper (paprika) carotenoids following treatment with pectinase, protease, cellulase and lipase in the presence of deoxycholate.

FIG. 3 demonstrates that incubation of red pepper (paprika) at 37° C. for 24 hours with a pectinase/cellulase [Rohament max (Rohm) 0.1% by weight], a protease [Corolase PN-L (Rohm) 0.1% by weight] that macerate the pectins, proteins and cellulose, respectively, and a lipase (amano 30, 0.1% by weight), results in deesterification of the monoesters and diesters to the free carotenoids yielding a chromatogram which is similar to the chromatogram obtained via chemical deesterification (FIG. 2).

Figure 4:
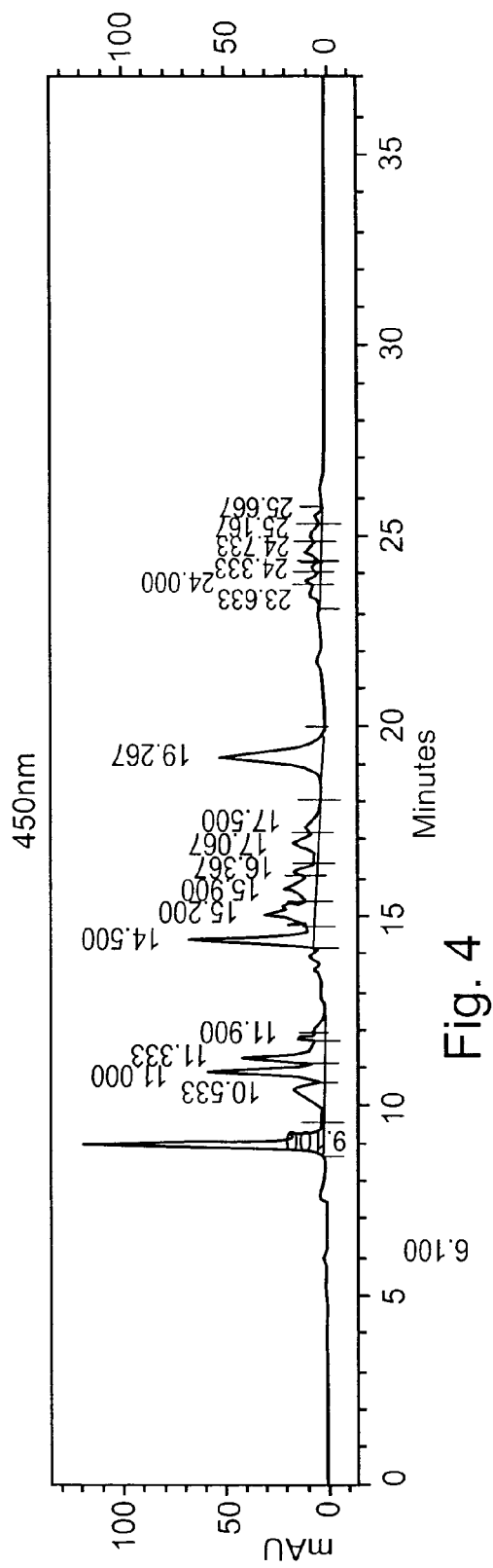
FIG. 4 is a HPLC chromatogram of paprika oleoresin carotenoids following treatment with deoxycholate and lipase.

FIG. 4 demonstrates deesterification of paprika oleoresin following incubation of the oleoresin in the presence of deoxycholate (4% by weight) and lipase (amano 30, 0.1% by weight) for 24 hours at 37° C.

Similar assays conducted with other lipases: pancreatic lipase, lipase A "Amano 6", lipase F-AP15 gave far poorer results.

Figure 5A:
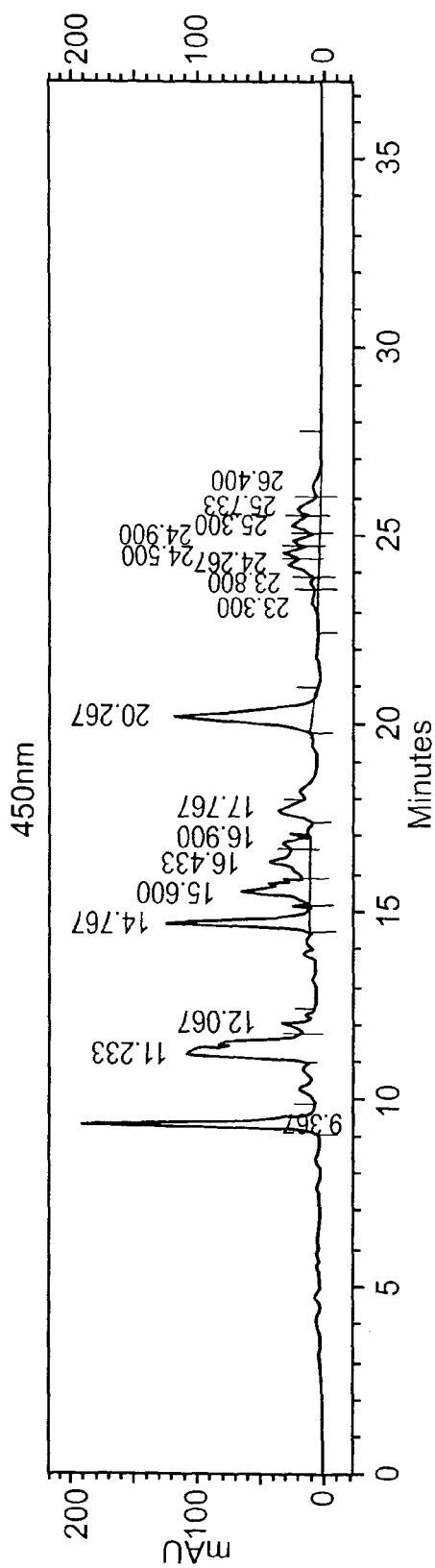
FIGS. 5a–c are HPLC chromatograms of paprika oleoresin carotenoids following treatment with varying concentarations of deoxycholate (2%, 3% and 4%, respectively) and lipase.
Figure 5B:
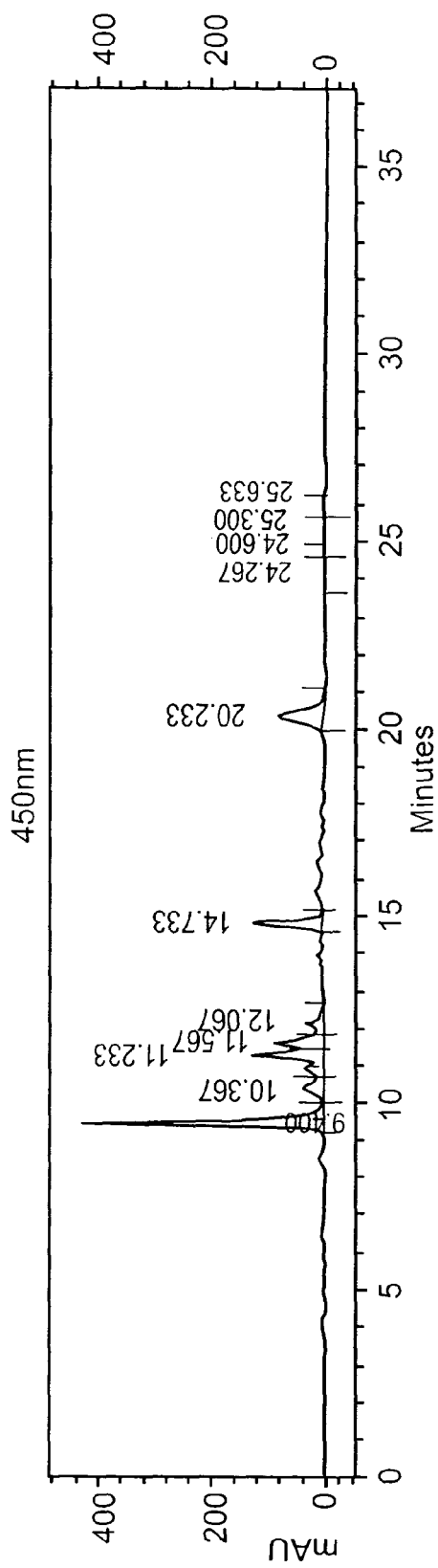
Figure 5C:
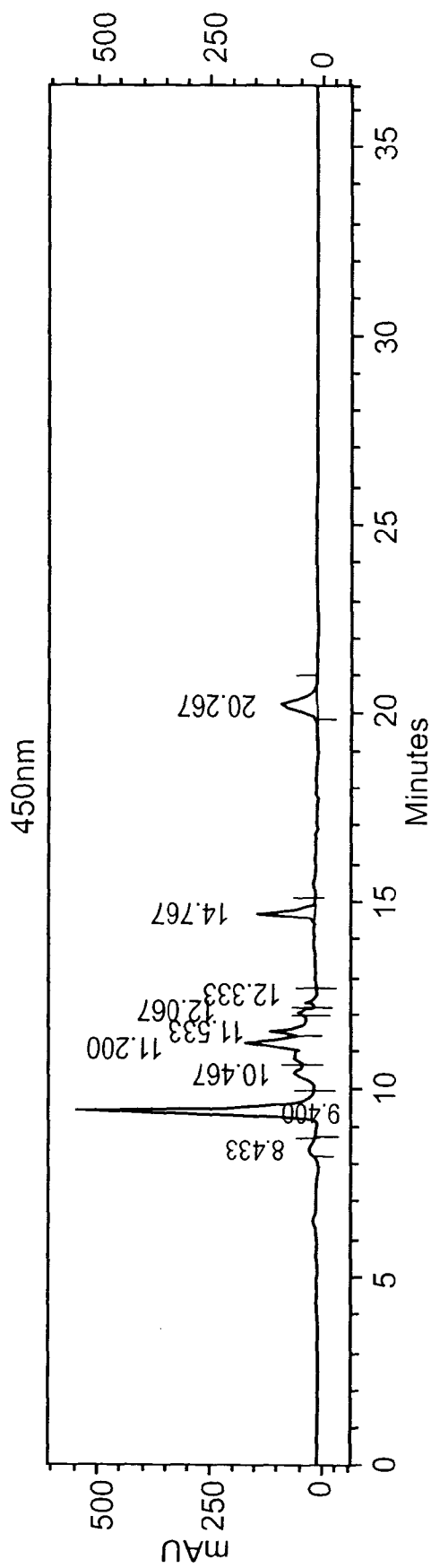

FIGS. 5a–c demonstrate deesterification of paprika oleoresin following incubation of the oleoresin in the presence of deoxycholate (2%, 3% or 4% by weight, respectively) and lipase (amano 30, 0.1% by weight) for 48 hours at 37° C. Note that similar carotenoid deesterification results are obtained with 3% and 4% deoxycholate, yet somewhat inferior carotenoid deesterification results are obtained with 2% deoxycholate. It will be appreciated that similar reaction optimizations can be performed for all other reaction ingredients.

These results demonstrate that treatment with esterase, under the conditions described herein, can efficiently deesterify red pepper carotenoids. As described hereinabove, enzymatic deesterification of paprika carotenoids according to the methods described herein, prior to ingestion of the red pepper carotenoids by human or animals, can significantly enhance the bioavailability of these compound from the gut to the plasma.

Example 2

The Effect of $CaCl_2$ and NaCl on the Lipase Activity

The activity of lipase at pH 7.6 at 37.0° C. for 18 hours on the deestrification of red-pepper carotenoids was measured in the presence of $CaCl_2$ and NaCl. As shown in Table 1, below, the addition of $CaCl_2$ to the reaction mixture, significantly increased lipase activity.

TABLE I

| Treatment | % Deestrification |
| --- | --- |
| Enzyme alone* | 73 |
| Enzyme + $CaCl_2$ 1.875 mM | 78 |
| Enzyme + $CaCl_2$ 3.75 mM | 82 |
| Enzyme + $CaCl_2$ 7.5 mM | 89 |

*50 mg oleoresin, 400 mg deoxycholate, 250 mg lipase.

In the presence of 150 mM NaCl without $CaCl_2$, the deestrification was of 87%. Thus, the addition of a metal salt to the lipase reaction mixture led to improved efficiency of lipase hydrolysis of the oleoresin carotenoids.

Example 4

Extraction of Oleoresin from Fresh or Frozen Red-pepper Fruits

Figure 6:
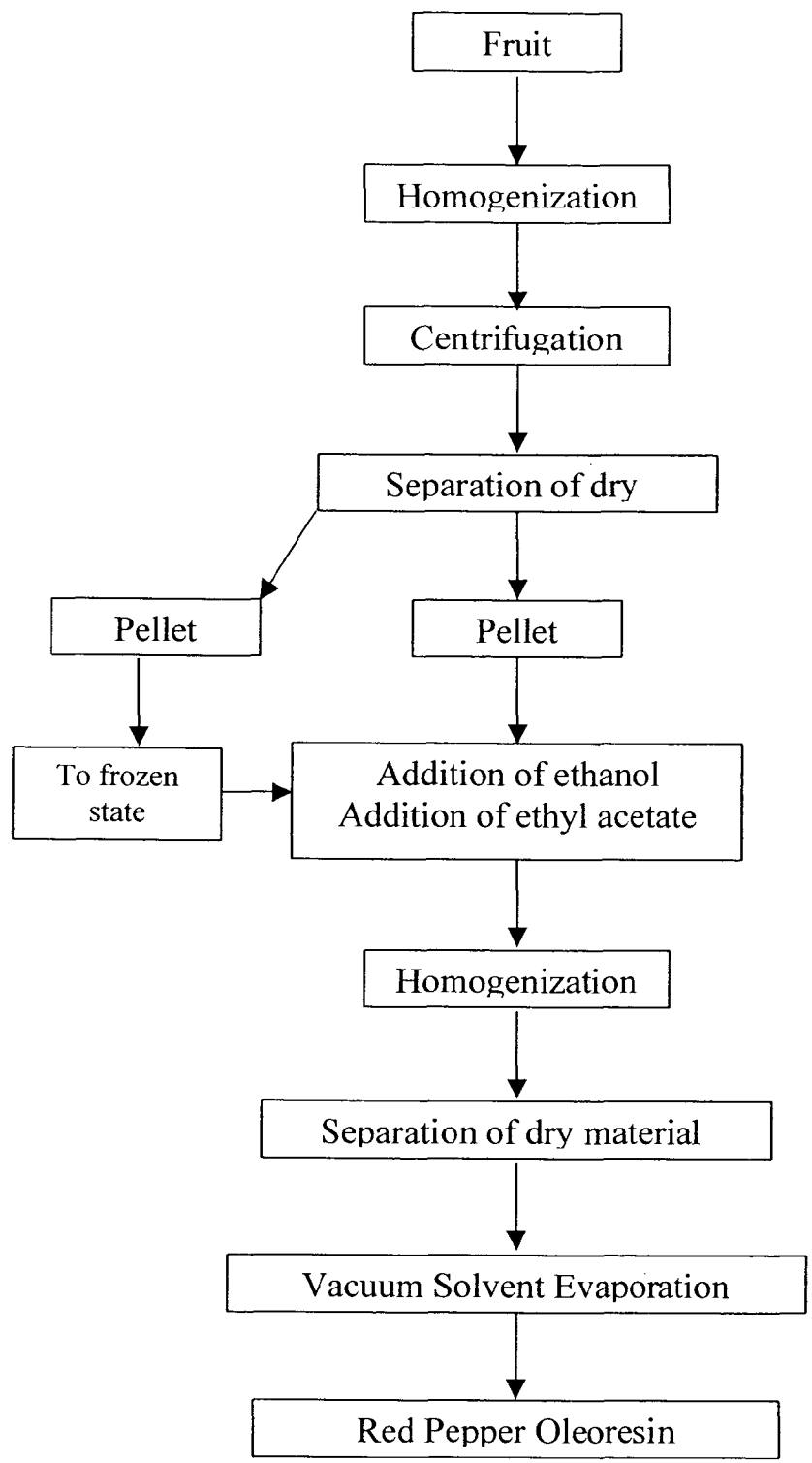
FIG. 6 demonstrates the steps of a method of extracting oleoresin from red pepper fruits, according to the present invention.

Fresh or frozen red-pepper fruits (100 parts) were homogenized with distilled water (40 parts) for 5 minutes to a juice. The juice was centrifuged at 25,000 g for 20 minutes and the pellet, either directly, or frozen, was mixed with 2 parts of ethanol and 10 parts of ethyl acetate. The elluent was homogenized for 1 minute. The solvents were separated from the dry material by centrifugation and evaporated at 45° C. under vacuum to receive red pepper oleoresin. The steps of the method are schematically presented in the flow chart of FIG. 6.

Example 5

Enzymatic Deesterification of Carotenoids from Paprika Oleoresin with Recycled Immobilized Lipase Enzymatic deesterification in solution requires large amounts of lipase enzyme, which is removed along with the aqueous phase during the extraction and washes of the deesterified carotenoid. In order to determine the effect of immobilization and reuse of lipase enzymes on efficiency and quality of deesterification of red pepper carotenoids, paprika oleoresin was deesterified with freshly prepared, and recycled matrix-immobilized *C. rugosa* lipase.

As is shown in the HPLC chromatogram of the carotenoids following deesterification and extraction, (FIG. 7a) matrix-immobilized lipase equivalent to 100 mg enzyme is equally efficient in deesterifying red pepper carotenoids in paprika oeloresin as freshly-prepared, unbound lipase in suspension (compared with FIG. 5a–5c).

Figure 8:
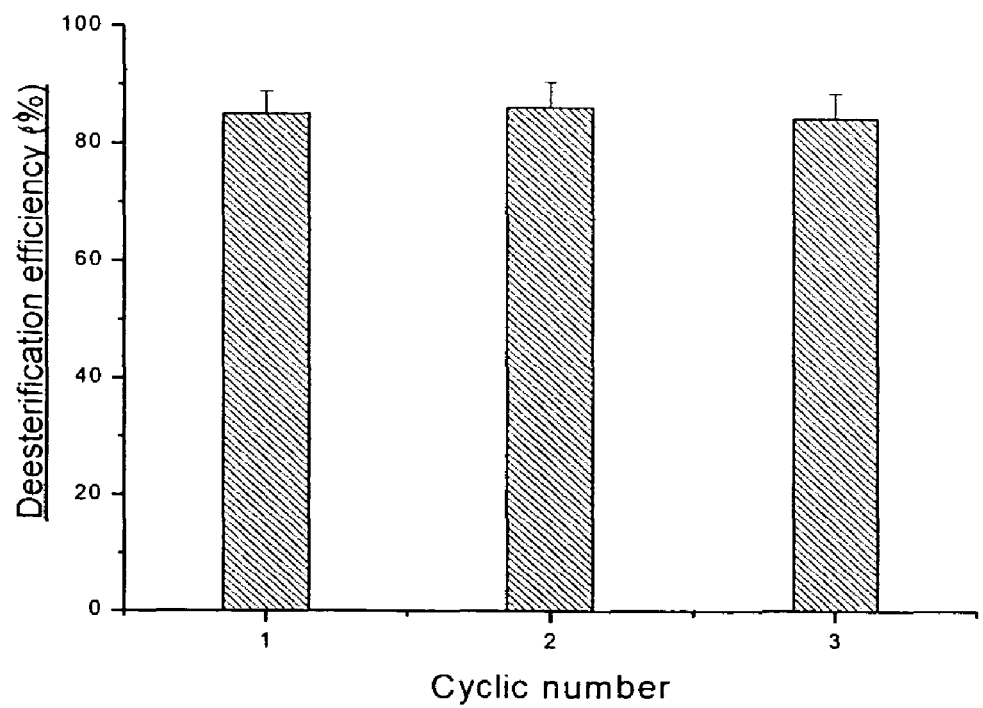
FIG. 8 shows the retention of lipase activity in the recycled matrix-bound lipase. Enzyme activity (expressed as percent deesterification of paprika oleoresin as compared with fresh matrix bound lipase) remained stable with no significant loss through 3 cycles of extraction and recovery of lipase.

Immobilized lipase beads may be recycled by precipitation, and reused. However, reuse of immobilized enzymes often incurs deterioration or alteration of activity. Thus, the immobilized lipase was tested for efficiency of deesterification of carotenoids in paprika oleoresin following 1 and 2 cycles of recovery. 20 mg of paprika oleoresin in deoxycholate and water emulsion was incubated with shaking for 24 hours with the lipase beads, followed by removal of the beads, extraction and analysis of the carotenoids. The identity of the HPLC chromatograms using freshly-prepared immobilized lipase (FIG. 7a), once recycled (FIG. 7b) and even twice recycled (FIG. 7c) enzyme indicate the near total retention of deesterification activity of recycled, immobilized lipase. FIG. 8 compares the efficiency of deesterification with fresh, once-, and twice-recycled immobilized lipase, quantifying the efficient reuse of the immobilized enzyme with paprika oleoresin. Loss of enzyme activity was less than 6% after 3 cycles of recovery and reuse. Thus, the immobilized lipase can be recycled numerous times without significant loss or alteration of activity.

Example 6

Enzymatic Deesterification of Carotenoids from Paprika Oleoresin with Recycled Deoxycholate Enzymatic deesterification in solution requires large amounts of the emulsifier, deoxycholate, which is removed along with the aqueous phase during the extraction and washes of the deesterified carotenoid. Recovery and reuse of the deoxycholate could be a significant improvement, reducing the amounts of deoxycholate in waste, and decreasing costs of the deesterification process. In order to determine the effect of recovery and reuse of deoxycholate on efficiency and quality of deesterification of red pepper carotenoids, paprika oleoresin was deesterified in the presence of freshly prepared, and dried, recycled deoxycholate.

Figure 9A:
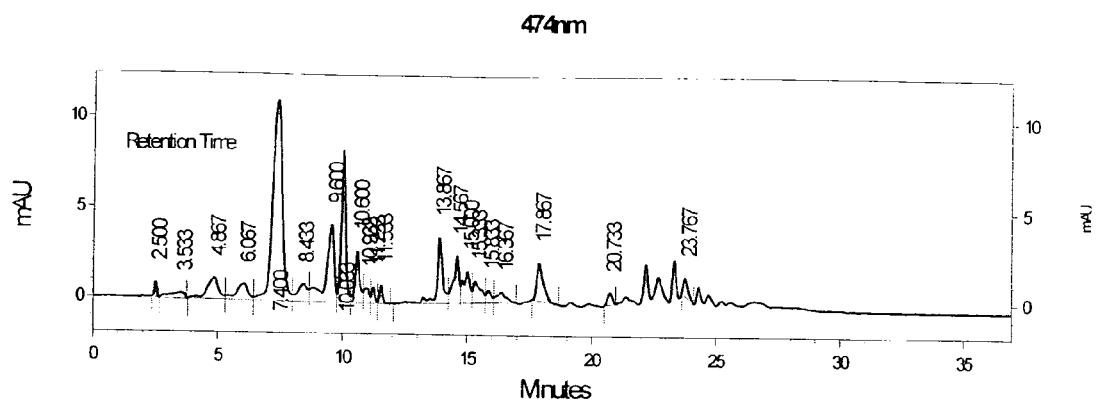
FIGS. 9a–9d are HPLC chromatograms of paprika oleoresin carotenoids extracted with fresh and recycled deoxycholate. 20 mg of paprika oleoresin was extracted with immobilized lipase in the presence of 200 mg fresh or recycled deoxycholate and water by shaking for 24 hours at 37° C., followed by ethyl acetate extraction, as describe in Materials and Experimental Methods hereinbelow.
Figure 9B:
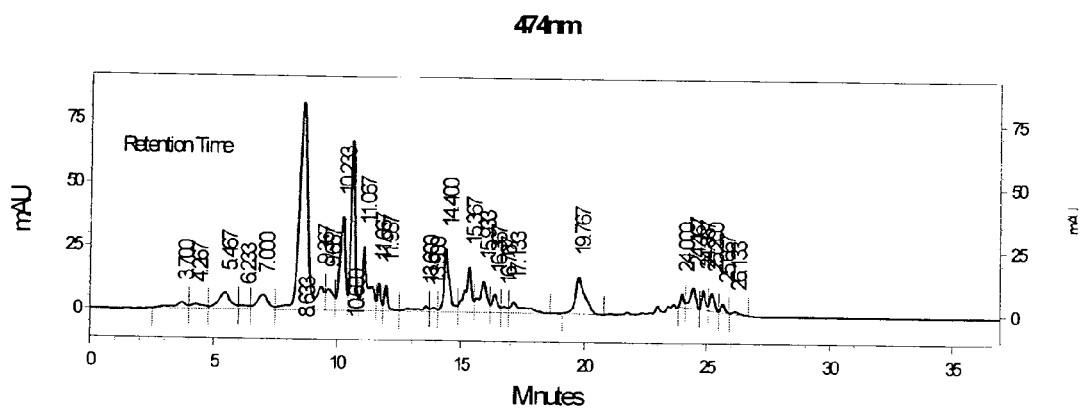
Figure 9C:
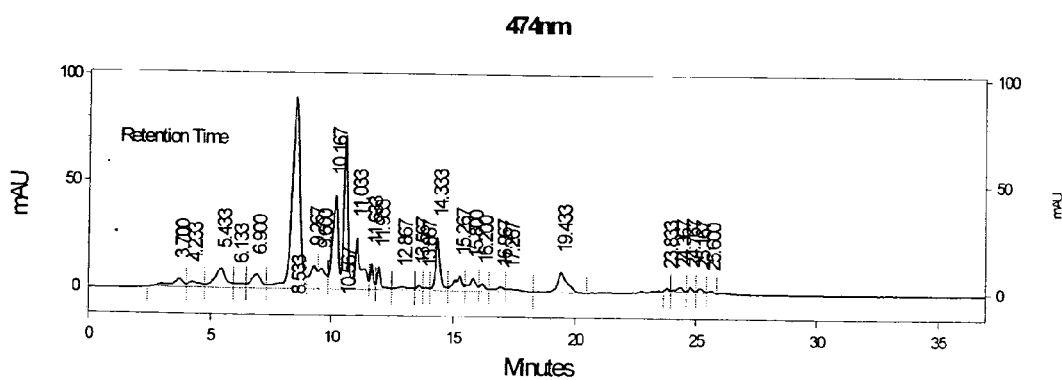
Figure 9D:
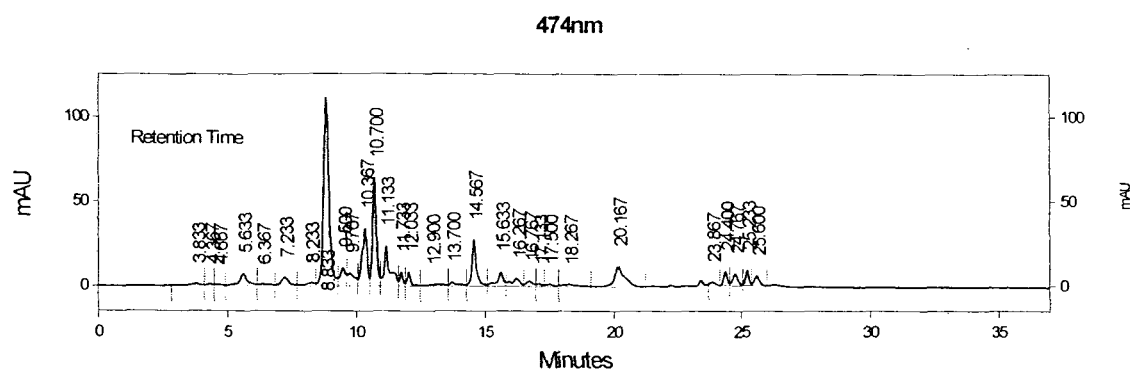

As is shown in the HPLC chromatograms of the carotenoids following deesterification and extraction, (FIG. 9b to 9d), recovered and reconstituted deoxycholate is equally efficient in deesterifying red pepper carotenoids in paprika oeloresin as freshly-prepared deoxycholate (compared with FIG. 9a). Deoxycholate was recovered from the aqueous phase following extraction and wash by either drying to a powder in an oven at 95° C. or freeze-drying (Ilshin Laboratories). Reconstitution was with water.

Figure 10:
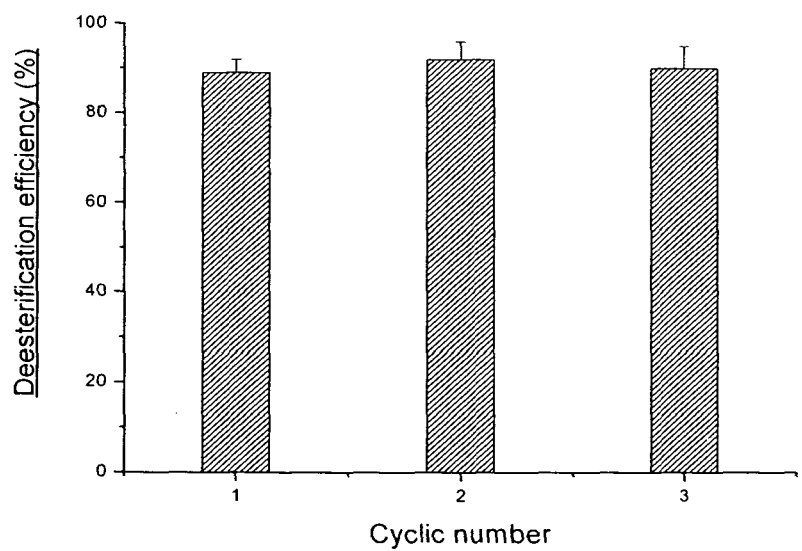
FIG. 10 shows the retention of emulsification activity in the recycled deoxycholate. Enzyme activity (expressed as percent deesterification of paprika oleoresin as compared with freshly prepared deoxycholate) remained stable with no significant loss, and apparent increase, through 3 cycles of drying and reconstitution of deoxycholate.

While reducing the present invention to practice, it was surprisingly discovered that recovery and recycling of deoxycholate resulted in increased efficiency of enzymatic deesterification of red pepper carotenoids, compared with freshly prepared deoxycholate. FIG. 10 compares the efficiency of deesterification with fresh (100%), once-, twice- and thrice-recycled deoxycholate, quantifying the efficient reuse of the emulsifier with paprika oleoresin. Clearly, the recovery and reuse of the deoxycholate enhances the enzymatic deesterification.

Without wishing to be limited by single hypothesis, the enhanced efficiency with recycling of deoxycholate may be due to the repeated extraction of natural emulsifiers present in the paprika oleoresin, and their cumulative addition to the deesterification reaction.

Example 7

Mild Alkaline Extraction of Enzymatically Deesterified Carotenoids with Ethyl-acetate and Production of a Novel, Vitamin E Enriched Carotenoid Composition Extraction of the enzymatically deesterified paprika oleoresin carotenoids has traditionally involved nonpolar solvents such as hexane. However, without wishing to be limited by one hypothesis, it is possible that since deeseterification of the carotenoids renders them more polar than the esterified starting material, extraction with highly nonpolar solvents incurs a loss of carotenoid material, increased time of extraction, and need for large volumes. Equally important, hexane and other highly non-polar solvents have been designated "Solvents That Should Be Limited" by the FDA, while more polar solvents such as ethyl acetate are considered solvents with "Low Toxic Potential" (see VICH GL18, "Impurities Solvents, June 2000, FDA, U.S. Department of Health and Human Services). In order to test the effects of extraction of enzymatically deesterified carotenoids with a more polar solvent, mild alkaline extraction of deesterified red pepper carotenoids with ethyl acetate was performed.

The separation by ethyl acetate was found to be simple, fast and required 4 times less solvent than separation by hexane (2–3 ml ethyl acetate/5 ml deesterification reaction, compared to 7–8 ml hexane/5 ml deesterification reaction). Further efficiency of extraction was effected by performing the extraction in a basic environment. In order to increase the concentration of the carotenoids in the organic phase, free fatty acids from the deesterification were titered to the salt form by increasing the pH to 9.5, using NaOH. Ethyl acetate (about 1 volume solvent to about 5 volumes of aqueous solution) was added, the carotenoids extracted, and the extracted oeloresin washed at least 3× with water (1:1 v/v). In the next stage, sodium sulfate was added to ethyl acetate to remove water from the ethyl acetate and dry it. The extracted carotenoids were concentrated by evaporation of ethyl acetate by a vacuum evaporator (Büichi) to a paprika oleoresin with free carotenoids. After mild alkaline ethyl acetate extraction, and concentration, the enzymatically deeseterified paprika oleoresin contains about 3 fold greater carotenoids in the oil than the paprika oleoresin before enzymatic deesterification (from 74 mg carotenoids/1 g oil to 210 mg/1 g oil).

Figure 13B:
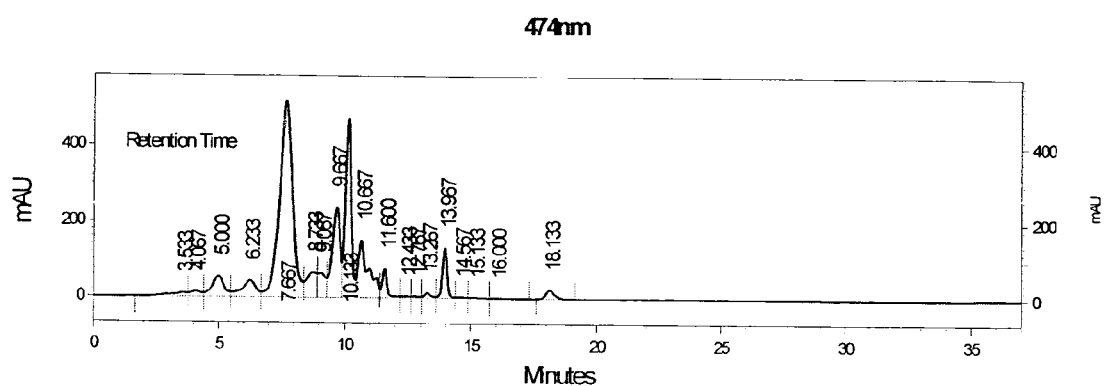

FIGS. 13a and 13b show the qualitative and quantitative advantage of ethyl acetate extraction. Whereas the HPLC chromatograms of the two enzymatically deesterified paprika oleoresin carotenoin preparations indicate an identical profile of highly deesterified carotenoids (from about 6.8 minutes to about 11.6 minutes), the concentrations of carotenoids (162 mg carotenoids/1 g deesterified extract with ethyl acetate, compared with 12.5 mg carotenoids/g with hexane) is far greater with the mild alkaline ethyl acetate extraction.

Figure 13C:
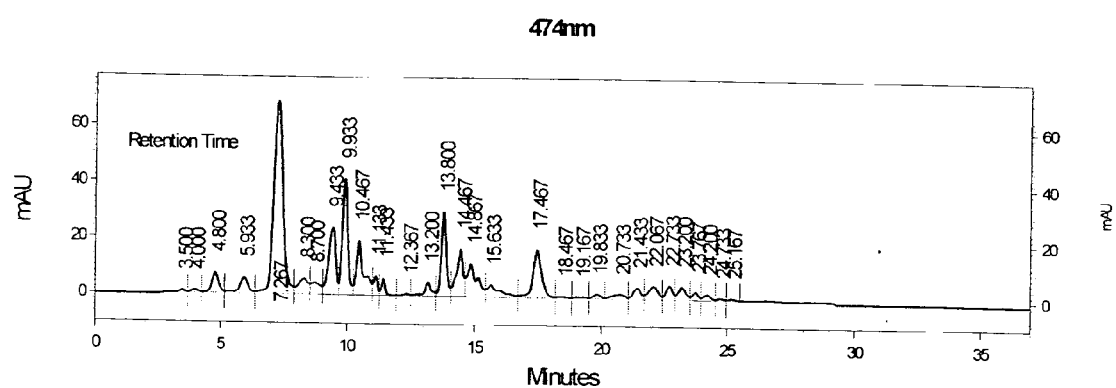
Figure 13D:
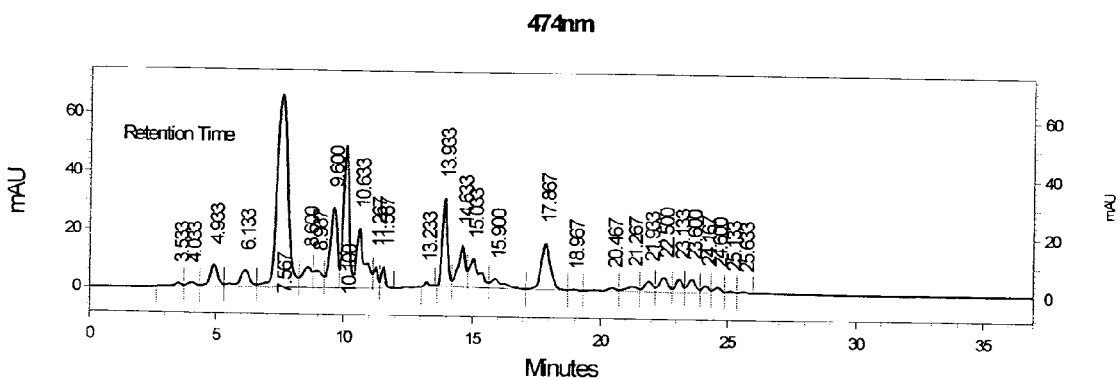

FIGS. 13c and 13d show the importance of mild alkalinization for efficient ethyl acetate extraction of enzymatically deesterified red pepper carotenoids. Whereas the HPLC chromatograms of the two enzymatically deesterified paprika oleoresin carotenoin preparations indicate an identical profile of highly deesterified carotenoids (from about 6.8 minutes to about 11.6 minutes), the concentrations of carotenoids (210 mg carotenoids/1 g deesterified extract with mildl alkaline ethyl acetate extraction, compared with 74.9 mg carotenoids/g with ethyl acetate extraction without pH adjustment) is far greater with the mild alkaline ethyl acetate extraction.

Paprika oleoresin is rich in Vitamin E, an extremely important antioxidant and nutritional supplement. While reducing the present invention to practice, it was surprisingly discovered that the mild alkaline ethyl acetate extraction of enzymatically deesterified red pepper carotenoids produced a novel red pepper oeloresin composition highly enriched in capsanthin, zeaxanthin, capsolutein and Vitamin E. FIGS. 14a and 14b show the previously unattainable enrichment of these important carotenoids, as well as that of Vitamin E, by mild alkaline ethyl acetate extraction after enzymatic deesterification.

Free fatty acids removed from the enzymatically deesterified carotenoids by the mild alkaline ethyl acetate extraction remain in the aqueous phase due to their conversion to salts in the elevated pH. Collection and re-acidificaction of this fraction, after separation from the organic phase, can render the free fatty acids extractable with a solvent such as methyl acetate, which, after a number of re-extractions, can be evaporated as described hereinabove, to provide a composition comprising concentrated, purified natural red pepper free fatty acids suitable for nutritional, food or feed supplementation.

Example 8

Antioxidant Activity of Enzymatically Deesterified Red Pepper Carotenoids

Inhibition of Lipid Oxidation

As described in the Background section hereinabove, carotenoids are important as food additives and nutritional supplements for their antioxidant properties. Oxidative modification of lipids and lipoproteins, which is thought to be a key step in the pathogenesis of cancer, cardiovascular disease and other conditions, is protected by antioxidants. However, certain of the carotenoids shows less consistent protective ability (Gaziano et al., 1995; Reaven et al., 1994). Mixtures of carotenoids have been found to be more effective as antioxidants than any single carotenoid (Stahl et al., 1998). Moreover, it has been reported that carotenoids enhance vitamin E antioxidant efficiency (Bohm et al., 1997; Fuhrman et al., 1997; Fuhrman and Aviram, 1999). In order to assess the antioxidant character of enzymatically deesterified red pepper carotenoids, the effect of enzymatically deesterified carotenoids on lipid oxidation in a carotene-linoleic acid assay was determined.

As described hereinabove, Vitamin E (mostly mixed tocopherols) is a significant component of natural sources of carotenoids, such as red pepper oleoresin. Vitamin E is also extracted and concentrated along with the carotenoid fraction, as demonstrated in FIG. 14. As an important antioxidant micronutrient, the presence of Vitamin E in the carotenoid composition is advantageous. However, in order to accurately assess the antioxidant properties of enzymatically deesterified red pepper carotenoids, a method of depleting Vitamin E without altering the intrinsic properties of the enzymatically deesterified carotenoids is required.

While reducing the present invention to practice, it was found that passage of the concentrated, enzymatically deesterified red pepper oleoresin over a column of magnesium silicate (Florisil, Supelco, Bellefonte, Pa., USA) equilibrated with hexane allowed separation of yellow and red (xanthophyll) carotenoids. Elution of the retained red carotenoids with ethyl acetate yielded quantitative recovery of red carotenoids, depleted of Vitamin E by more than 40-fold (compare HPLC of Vitamin E in FIGS. 11a and FIG. 11b). Thus, the antioxidant effects of the enzymatically deesterified red pepper oleoresin carotenoids could then be accurately asessed.

When compared to lycopene (x's, FIGS. 15a and b) and beta carotene (stars, FIGS. 15a and 15b), the enzymatically deesterified red pepper carotenoids showed superior inhibition of lipid oxidation (FIGS. 15a and 15b, closed squares and closed triangles), at both neutral pH (as is found in the blood, for example) (FIG. 15a), and strongly acidic pH (as is found in the stomach, for example) (FIG. 15b). Both Vitamin E containing (closed squares, FIGS. 15a and 15b), and Vitamin E-depleted deesterified red pepper carotenoids (closed triangles, FIGS. 15a and 15b) showed similar, superior antioxidant properties irrespective of pH.

Figure 16A:
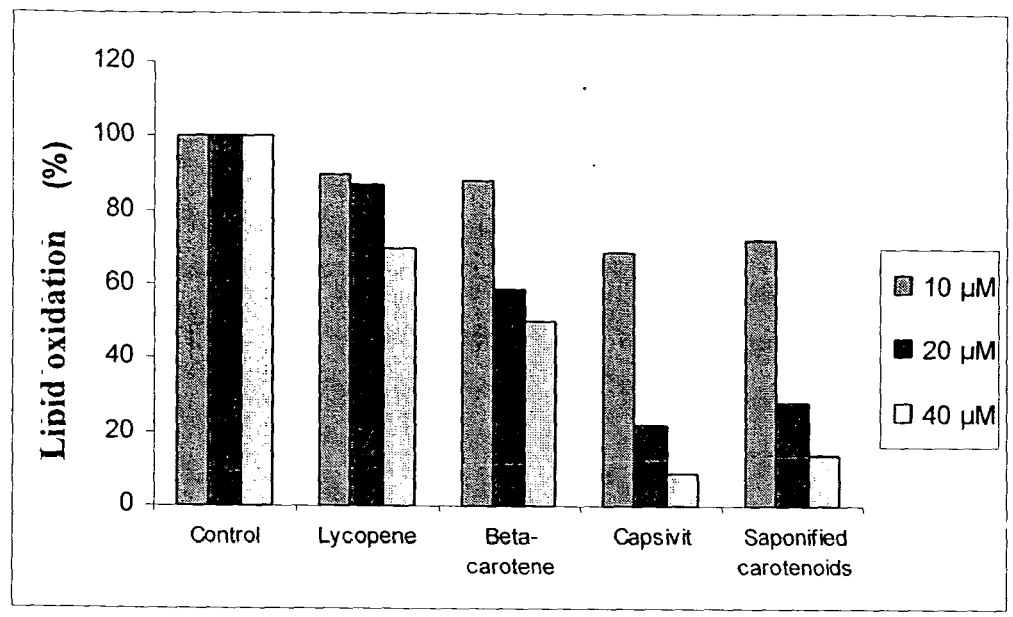
FIGS. 16a and 16b are bar graphs showing the superior antioxidant effects of enzymatically deesterified carotenoids, as compared to other carotenoid antioxidants. Note the superior inhibition of lipid oxidation by enzymatically deesterified carotenoids (Capsivit and Saponified carotenoids) at 10 µM (grey squares), 20 µM (dark grey squares) and 40 µM (light squares) antioxidant concentration, with nearly 6 times greater protection of the lipids from oxidation, compared to the beta-carotene and lycopene, at 40 µM.
Figure 16B:
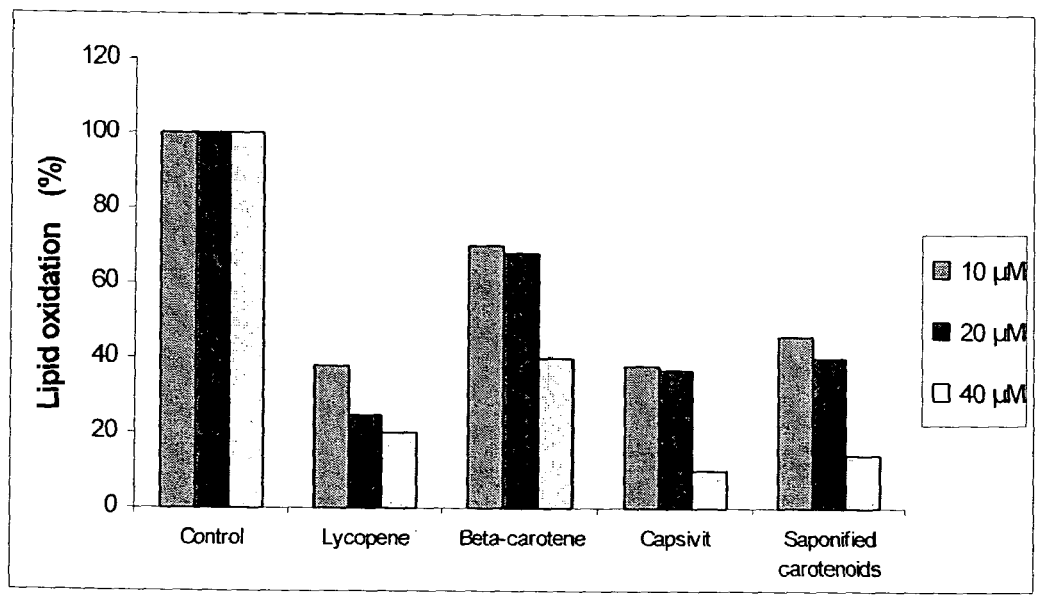

The bar graphs of the effect of carotenoid concentration on the antioxidant character of enzymatically deesterified carotenoids in FIGS. 16a and 16b clearly demonstrate that at all concentrations and at both neutral and alkaline pH, both Vitamin E containing ("Capsivit", FIGS. 16a and 16b), and Vitamin E-depleted deesterified red pepper carotenoids ("saponified carotenoids", FIGS. 16a and 16b) showed similar, superior antioxidant properties.

Example 9

Stability of Enzymatically Deesterified Red Pepper Carotenoids

In order to determine the stability of enzymatically deesterified red pepper carotenoids, the color concentrations of emulsions prepared from paprika oleoresin before and after enzymatic deesterification and mild alkaline ethyl acetate extraction were compared over a 30 day storage period. The color concentration was determined in the presence of two concentrations of non-ionic, non-denaturing detergent (Tween 20) to assess the dispersal of the carotenoids in the water.

The Table in FIG. 12 shows the superior stability of the enzymatically deesterified paprika oleoresin in water, upon preparation (Time 0), and after 10 days storage (After 10 days). Comparing the absorbance values at 474 nm, the enzymatically deesterified oleoresin (1 mg/100 ml water) clearly retained greater than 97% of the color concentration at 0.15% Tween-20 (1.402 vs 1.377) and at 0.03% Tween 20 (1.352 vs 1.326), with only a small difference between the color concentration of the emulsion in higher (0.15%) and lower (0.03%) Tween concentrations. In sharp contrast, the untreated, esterified paprika oleoresin (1 mg/100 ml water) retained only around 70% of initial color concentration after 10 days storage (0.912 vs 0.662) in lower Tween (0.03%) concentration, and only 95% (1.220 vs 1.159) at the higher Tween (0.15%) concentration.

Further, it was observed that upon standing, the emulsion prepared from the untreated, esterified paprika oleoresin, but not the enzymatically deesterified paprika oleoresin, developed a ring of oil at the bottleneck of it's container, along with the loss of color concentration. Without wishing to be limited to a single hypothesis, the loss of color concentration is most likely caused by hydrophobic interactions and accumulation of the untreated, esterified carotenoids in the oily ring.

Thus, the enzymatically deesterified, mild alkaline ethyl acetate paprika oleoresin has superior storage and dispersive properties in an aqueous solution, even at low detergent concentrations.

Taken together, these results show that: i) red carotenoids, such as those found in red pepper fruits, can be efficiently and quantitatively deesterified by gentle enzymatic hydrolysis, using the novel conditions described hereinabove, to produce a deesterified red carotenoid composition equal if not superior to that produced by chemical saponification; ii) immobilized enzymes and recovered, recycled emulsifiers, such as deoxycholate, can be used and reused in the deesterification process without significant loss of quality or quantity of the deesterified carotenoid product; iii) novel, efficient extraction methods using ethyl acetate and mild alkaline conditions produce a previously unattainable composition comprising high concentrations of enzymatically deesterified red carotenoids and Vitamin E, as well as purified, isolated carotenoid free fatty acids; Vitamin E can be quantitatively depleted from the enzymatically deesterified red pepper carotenoids chromatography; and v) enzymatically deesterified red pepper carotenoids have superior antioxidant characteristics, with, or without the Vitamin E component enriched by enzymatic deesterification and extraction described hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

Akhtar P., Gray I J., Thomas H C., Garling D L. And Booren Am. Dietary pigmentation and carotenoids in rainbow trout muscle and liver tissue. J. Food Chem. 1999, 64, 234–239.

Aviram M. Review of human studies on oxidative damage and antioxidant protection related to cardiovascular diseases. Free Radic. Res. 1999, (in press).

Aviram M. Paraoxonase protects lipoproteins foam oxidation and attenuates atherosclerosis. Cardiovas. Res. 1999 (in press).

Aviram M, Maro I, Keidar S, Hayck T et al., Lesioned low-density lipoprotein in atheroscelrotic aplipoprotein E-deficient transgenic mice and human is oxidized and aggregated. Biochem. Biophys. Res. Commun. 1995, 16, 501–513.

Aviram M. Oxidized low density lipoproteins (OX-LDL) interaction with macrophages in atherosclerosis and the antiatherogenicity of antioxidants. Europ. J. Clin. Chem. Clin Biochem. 1996, 34, 599–608.

Birchall M A, Schock E, Harmon B V, Gobe G. Apoptosis, mitosis, PCNA and bcl-2 in normal, leukoplakic and malignant epithelia of the human oral cavity: prospective, in vivo study. Oral Oncol 1997,33, 419–425

Block G, Patterson B, Subar A. Fruit, vegetables and cancer prevention. A review of the epidemiological evidence. Nutr. Cancer, 1992, 18, 3–4.

Bohm F, Edge R, Land J E, McGravey D J, Triscott J G. Carotenoids enhance vitamin E antioxidant efficiency. J. Am. Chem. Soc. 1997, 119, 621–622.

Bosland P W. Breeding for quality in Capsicum. Capsicum Eggplan Newsl. 1993. 12, 25–28.

Bras A, Sanches R, Cristovao L, et al. Oxidative stress in familial adenomatous polyposis. Eur J Cancer Prev 1999, 8, 305–310.

Britton G. In Natural Food Clorants (Hendry G A Fand Houghton J. D. eds) Blockie Academic Professional, London, 1996, p. 197.

Bundgaard T, Wildt J, Frydenberg M, Elbrond 0, Nielsen J E. Case-control study of squamous cell cancer of the oral cavity in Denmark. Crit Rev Oral Biol Med 1995, 6, 5–17.

Burton G W, Ingold K U. β-carotene: An unusual type of lipid antioxidant. Science, 1984, 224, 569–573.

Collins A R, Gedik C M, Olmedilla B, Southon S, Bellizi M. Oxidative DNA damage measured in human lymphocytes: large differences between sexes and between countries, and correlation with mortality rates. FASEB J 1998, 12, 1397–400.

Cowan C G, Calwell E I L, Young I S, McKillop D J, Lamey P-J: Antioxidant status of oral mucosal tissue and plasma levels in smokers and non-smokers. J Oral Path Med 1999, 28, 360–363.

Dammer R, Neiderdelman H, Friesenecker J, Fleisschmann H, Hermann J, Kreft M. Withdrawal therapy of patients with alcoholism and nicotine dependence with carcinomas in the area of the head a neck. Luxury or necessity? Carcinogenesis 1998, 19, 509–514.

De Stefani E, Boffetta P, Oreggia F, Mendilaharsu M, Deneo-Pellegrini H. Smoking patterns and cancer of the oral cavity and pharynx: a case control study in Urugay. Indian J Cancer 1998, 35, 65–72.

Dugas T R, Morel D W, Harrison E H. Dietary supplementation with β-carotene, but not with lycopene, inhibits endothelial all-mediated oxidation of low-density lipoprotein. Free Rad. Biol. Med. 1999, 26, 1238–1244.

Esterbauer H, Dieber-Rotheneder M, Striegl G, Waeg G. Role of vitamin E in preventing the oxidation of low-density lipoproteins. Am. J. Chim. Nutr. 1991, 53, 3145–3215.

Esterbaur H, Cheseman K H. Determination of aldehydic lipid peroxidation products: malonaldehyde and 4-hydroxynonenal. Methods Enzymol 186, 407–421.

Everett J A, Dennis M F, Patel K B, Maddix S, Kunder S C, Wilson R L. Scavenging of nitrogen dioxide, thiyl and sulfonyl free radicals by the nutritional antioxidant β-carotene. J. Biol. Chem. 1996, 271, 2988–2991.

Frankel E N, Kanner J, German J B, Kinsella E J. Inhibition of oxidation of human low-density lipoprotein with phenolic substances in red-wine Lancet 1993, 341, 454–457.

Fuhrman B, Elis A. and Aviram M. Antiathrogenic effects of lycopene and β-carotene: inhibition of LDL oxidation, and suppression of cellular cholesterol synthesis. Natural Antioxidants and Anticarcinogenesis in Nutrition Health and Disease. Eds. Kumpulainen J. T. and Salonen J. T. Society of Chemistry, Cambridge, U.K. 1999, pp. 226–230.

Fuhrman B, Lavy A, and Aviram M. Consumption of red wine with meals reduces the susceptibility of human plasma and LDL to undergo lipid peroxidation. Am. J. Clin. Nutr. 1995, 61, 549–554.

Gaziano J M, Hatta A, Flynn M, Johnson E J et al., N I, Ridker P M, Henekens C H, Frei B. Supplementation with beta-carotene in vivo and in vitro does not inhibit low density lipoprotein oxidation. Atherosclerosis 1995, 112, 187–195.

Gerster H. The potential role of lycopene for human health. J. Am. Cell. Nutr. 1997, 16, 109–126.

Goldsworthy T L, Conolly R B, Fransson-Steen R. Apoptosis and cancer risk assessment. Mutat Res 1996, 365, 71–90.

Goodwin T W: "The Biochemistry of the Carotenoids" Vol. 1: "Plants". New York, Chapman and Hall, 1980, p. 203.

Gravis G, Pech-Gourgh F, Viens P, Alzieu C, Camerlo J, Oziel-Taieb S, Jausseran M, Maraninchi D. Phase II study of a combination of low-dose 13-cis-retinoic acid and interferon-alpha in patients with advanced head and neck squamous cell carcinoma. Anticancer Drugs 1999, 10, 369–374.

Halliwell B. Cellular stress and protection mechanism. Biochem. Soc. Trans. 1996, 24, 1023–1027.

Hart A k, Karakala D W, Pitman K T, Adams J F. Oral and oropharyngeal squamous cell carcinoma in young adults: a report on 13 cases and review of the literature. Carcinogenesis 1999, 20 743–748.

Hennekens C H, Buring J E, Manson J E, Stampfer M et al. Lack of effect of long-term supplementation with beta-carotene on the incidence of malignant neoplams and cardiovascular disease. N. Engl. J. Med. 1996, 334, 1145–1149.

Hertog M G L, Feskens E J M, Hollman P C H, Katan M B, et al. Dietary antioxidants flavonoids and risk of coronary heart disease: The Zutphen Eldery Study Lancet 1993, 342, 1007–1011.

Hirayama O, Nakamura K, Hamda S, Kobayasi Y. Singlet oxygen quenching ability of naturally occurring carotenoids. Lipid, 1994, 29, 149–151.

Hong W K, Lippman S M, Itri L M, et al. Prevention of second primary tumors with isotretinoin in squamous-cell carcinoma of the head and neck. N Engl J Med 1990; 323:795–801

Ilyas M, Straub J, Tomlinson I P, Bodmer W F. Genetic pathways in colorectal and other cancers. Eur J Cancer 1999, 35, 335–351.

Iribarren C, Folsom A R, Jacobs D R Jr et al. Association of serum vitamin levels, LDL susceptibility to oxidation and autoantibodies against MDA-LDL with carotid atherosclerosis. Arterioscler. Tromb. Vase Biol. 1997, 17, 1171–1177.

Jain C K, Agarwal S, Venketeshwer R. The effect of dietary lycopene on bioavailability, tissue distribution, in vivo antioxidant properties and colonic preneoplasia in rats. NutrRes 1999, 191, 383–391.

Kanner J, and Kinsella, J E, Lipid deterioration: β-carotene destruction and oxygen evolution in a system containing lactoperoxidase, hydrogen peroxide and halides. Lipids. 1983, 18, 198.

Kanner J, Frankel E, Granit R, German B, and Kinsella E, Natural antioxidants in grapes and wines. J. Agric. Food Chem. 1994, 42, 64–69.

Kennedy T A, Liebler D C. Peroxyl radical scavenging by β-carotene in lipid bilayers. J. Biol. Chem. 1992, 267, 4658–4663.

Khachik F. Beecher G R, Smith J C. Lutein, lycopene and their oxidative metabolites in chemoprevention of cancer. J. Cell Biochem. 1995, 22, 236–246.

Kim D J, Takasuka N, Kim J M, Sekine K, Ota T, Asamoto M, Murakoshi M, Nishino H, Nir Z, Tsuda H (1997) Chemoprevention by lycopene of mouse lung neoplasia after combined initiation treatment with DEN, MNU and DMH. Cancer Lett 120,15–22.

Kim J M, Araki S, Kim D J, Park C B, Takasuka N, Baba-Toriyama H, Ota T, Nir Z, Khachik F, Shimidzu N, Tanaka Y, Osawa T, Uraji T, Murakoshi M, Nishino H, Tsuda H (1998) Chemopreventive effects of carotenoids and curcumins on mouse colon carcinogenesis after 1,2-dimethylhydrazine initiation. Carcinogenesis 19,81–85.

Knekt P, Jarvinen R, Reunaneu A, Maatek. Flavonoid intake and coronary mortality in Finland: a cohort study. Brit. Med. J. 1996, 312, 478–481.

Knudsen K E, Weber E, Arden K C, Cavenee W K, Feramisco J R, Knudsen E S. The retinoblastoma tumor suppressor inhibits cellular proliferation through two distinct mechanisms inhibition of cell cycle progression and induction of cell death. Oncogene 1999, 16, 5239–5245.

Kohlmeier L, Hossting S B. Epidemiologic evidence of a role of carotenoids in cardiovascular disese prevention. Am. J.Clin. Nutr. 1995, 62, 137s–146s.

Kohlmeier L, Kark J D, Gomez-Grania E, et al. Lycopene and mycoradial infraction risk in the EURAMIC study. Am. J. Epidemiol. 1997, 146, 618–622.

Kondo K, Matsumoto A k, Kusata H, Tenahashi H, Koda H, et al. Inhibition of oxidation of low-density lipoprotein with red-wine. Lancet, 344, 1152–1152.

Kristenson M, Zieden B, Kuinkiene S, et al. Antioxidant state and mortality from coronary heart disease in Lithuanian and Swedish men. B.M.J. 1997, 314, 629–632.

Lapidot, T. Harel, S. Akiri, B. Granit, R. and Kanner, J. PH-Dependent forms of red wine anthocyanins as antioxidants. J. Agric. Food Chem. 1999, 47, 67–70.

Lapidot, T. Harel, S. Granit, R. Kanner, J. Anthocyanins in red wines: Antioxidant activity and bioavailability in human. In Natural 1999, 151–161.

Lee C M. Borleau A. Boileau T W M, Williams A W. Et al. Review of animal models in carotenoid research. J. Nutr. 1999, 129, 2271–2277.

Lee I M. Cook N R. Monson J E. Buring J E. Hennekens C H. B-carotene supplementation and incidence of cancer and cardiovascular disease: the women's study. J. Natl. Cancer Inst. 1999, 91, 2102–2102.

Lefebvre V, Kunz M, Camara B. and Palloix A. The capsanthin-capsorubin synthase gene: candidate for the y locus controlling the red fruit color in pepper. Plant Molec. Biol. 1998. 36, 785–789.

Levy A, Harel S, Palevich D, Akiri B, Menagem E, and Kanner J. Carotenoid pigments and β-carotene in paprika fruit (Capsicum spp.) with different genotypes. J. Agric. Food Chem. 1995. 43, 362–367.

Levy A, Levy Talia, S, Elikin Y, Menagem E, Barzilai M, and Kanner J. Carotenoid and vitamin C and E contents in isogenic chlorophyll and color mutants of paprika (Capsicum annuum L.). Proc. Xth. Eucarpia Meeting on Genetics and Breeding of Capsicum and Eggplant. 1998, 257–260.

Levy J. Bosin E, Feldman B, Giat Y et al. Lycopene is a more potent inhibitor of human cancer cell proliferation than lither α-carotene of β-carotene. Nutr. Cancer 1995, 24, 257–267.

Lin Y, Burri B J, Neidlinger T R, Muller H G, Ducker S R, Cliford A J. Estimating the concentration of beta-carotene required for maximal protection of low-density lipoprotein in women. Am. J. Clin. Nutr. 1998, 67, 837–845.

Mao L. Leukoplakia: Molecular understanding of premalignant lesions and implications for clinical management. *Mol Med Today* 1997, 3, 442–448

Mathews Roth M M, Welankiwar S, Sehgal P K, Lausen N L G et al. Distribution of ($^{14}$C) lycopene in rats and monkey. J. Nutr. 1990, 120, 1205–1213.

Matsufuji H, Nakamura H, Chino M and Takeda M. Antioxidant activity of capsanthin and the fatty acid estess in paprika (*Capsicum* annuum). J. Agric. Food Chem. 1998, 46–49.

Mayne S T, Beta-carotene, carotenoids and disease prevention in human, FASEB J. 1996, 10, 690–699.

Murakoshi M, Nishino H, Satomi Y, Takayasu J et al. Potent preventive action of α-carotene against carcinogenesis spontaneous liver carcinogenesis in mice are suppressed more effectively by β-carotene. Cancer Res. 1992, 52, 6583–6587.

Narisawa T, Fukaura Y, Hasebe M, Ito M, Aizawa R, Murakoshi M, Uemura S, Khachik F, Nishino H (1996) Inhibitory effects of natural carotenoids, alpha-carotene, beta-carotene, lycopene and lutein, on colonic aberrant crypt foci formation in rats. Cancer Lett 107,137–142.

Ojima F, Sakamoto H, Ishiguro Y, Ferao J. Consumption of carotenoids in photosensitized oxidation of human plasma and low-density lipoprotein. Free Rad. Biol. Med. 1993, 15, 377–384.

Olson J A. Carotenoids, In: Modern Nutrition in Health and Disease (Shils M E, Olson J A, Shike M. & Ross A C eds) Williams and Wilkins, Baltimore, Md. 1999, p. 525.

Oshima S, Sakamoto H, Ishiguro Y and Terao J. Accumulation and clearnce of capsanthin in blood plasma after the ingestion of paprika juice in men. J. Nut. 1997, 127, 1475–1479.

Pappalardo G, Maiani G, Mobarhan S, Guadalaxara A, Azzini E, Raguzzini A, Salucci M, Serafini M, Trifero M, Illomei G, Ferro-Luzzi A (1997) Plasma (carotenoids, retinol, alpha-tocopherol) and tissue (carotenoids) levels after supplementation with beta-carotene in subjects with precancerous and cancerous lesions of sigmoid colon. Eur J Clin Nutr 51, 661–666.

Poulos J. Pepper breeding (Capsicum spp.): achievements, challenges and possibilities. Plant Breeding Absr. 1994, 64, 143–146.

Rao A V and Agarwal S. Role of lycopene as antioxidant carotenoid in the prevention of chronic disease: A review. Nutr. Res. 1999, 19, 305–323.

Reaven P D, Ferguson E, Navab M, Powell F L. Susceptibility of human LDL to oxidative modification. Effects of variations in beta-carotene concentration and oxygen tension. Alterioscler. Troub. 1994, 14, 1162–1169.

Romanchik J E, Morel D W, Horrison E H. Distribution of carotenoids and alpha-tocopherol among lipoproteins do not change when human plasma is incubated in vitro. J. Nutr. 1995, 88, 1646–1650.

Ross R. The pathogenesis of atherosclerosis: a perspective for the 1990. Nature, 1993, 362, 801–809.

Schildt E B, Eriksson M, Hardell M, Magnuson A. Oral snuff, smoking habits and alcohol consumption in relation to oral cancer in a Swedish case-control study. Int J Cancer 1998, 77, 333–336

Schoelch M L, Le Q T, Silverman S Jr, McMillan A, Dekker N P, Fu K K, Ziober B L, Regezi J A. Apoptosis-associated proteins and the development of oral squamous cell carcinoma. Oral Oncol 1999, 35, 77–85.

Schroeder W A and Johnson E A. Singlet oxygen and peroxyl radical regulate carotenoid biosynthesis in Phaffia Rhodozyma. J. Biol. Chem. 1995, 270, 18374–18379.

Schwartz J L and Shklar G. Retinoid and carotenoid angiogenesis: a possible explanation for enhanced oral carcinogenesis. Nutr Cancer 1997, 27, 192–99.

Schwartz J L and Shklar G. The selective cytotoxic effect of carotenoids and alpha tocopherol on human cancer cell lines in vitro. J Oral Maxill Surg 1992, 50, 367–373.

Schwartz J L Tanaka J, Khandekar V, Herman T S, Teicher B. Beta carotene and/or vitamin E as modulators of alkakylating agents in SSC-25 human squamous carcinoma cells. Cancer Chem and Pharmacol 1991, 29, 207–213.

Schwartz J L, Antoniades D Z, Zhao S. Molecular and biochemical reprogramming of oncogenesis through the activity of antioxidants and prooxidants. Ann NY Acad Sci 1992, 686, 292–279.

Schwartz J L, Flynn E A, Shklar G. The effect of carotenoids on antitumor immune response in vivo and in vitro with hamster and mouse immune effectors. Ann NY Acad Sci 1990, 587, 92–109.

Schwartz J L, Shklar G, Trickler D. p53 in the anticancer mechanism of vitamin E. Oral Oncol 1993, 29B, 313–183.

Sies H, Stahl W. Vitamins E, C, β-carotene and other carotenoids as antioxidants as antioxidants. Am. J. Clin. Nutr. 1995, 62, 1315–1321.

Smith E M, Hoffman H T, Summersgill K S, Kirchner H L, Turek L P, Haugen T H. Human papillomavirus and risk of oral cancer. Int J Cancer 1998, 77, 341–346

Stahl W, Junghans A, deBoer B, Driomina E S. et al. Caroteoid mixtures protect multieamillar liposomes against oxidative damage; synergistic effects of lycopene and lutein. FEBS Lett 1998, 427, 305–308.

Steinberg D, et al. Antioxidants in the prevention of human atheroscelrosis. Summary of the proceedings of a National Heart, Lung and Blood Institute Workshop: Circulation 1992, 85, 2337–2344.

Steinberg D, Parthasarathy S, Carew T E, Khoo J C and Witztum J L. Beyond cholesterol: modifications of low-density lipoprotein that increase its atherogenecity. N Engl. J. Med. 1989, 320, 915–924.

Sthal W, Sies H. Uptake of lycopene and its geometrical isomers is greater from heat-processed than form unprocessed tomato juice in humans. J. Nutr. 1992, 122, 2161–2166.

Stich H F, Roisin M P, Hornby A P et al: Remission of oral leukoplakias and micronuclei in tobacco/betel quid chewers treated with beta-carotene and with beta-carotene plus vitamin A. Int J Cancer 1998, 421, 195–199.

Tanaka T, Morishita Y, Suzui M, Kojima T et al. Chemo prevention of mouse urinary bladder carcinogenesis by the naturally occuring carotenoid astaxanthin. Carcinogenesis. 1994, 15, 15–19.

Wagner J R, Motchnik P A, Stocker R, Sies H, Ames B N. The oxidation of blood plasma and low-density lipoprotein components by chemically generated single oxygen. J. Biol. Chem. 1993, 268, 18502–18506.

Watson A D, Navab M, Hama S Y, Sevanian A et al. Effect of platelet activating factor-acetyl hydrolase on the formation and action of minimally oxidized low-density lipoproteins. J. Clin. Invest. 1995, 95, 774–782.

Weisburger J H. Mechanisms of action of antioxidants as exemplified in vegetables, tomatoes and tea. Food Chem Toxicol 1999, 37, 943–948.

Woodall A A, Lee S W, Wesie R J, Jackson M J and Britton G. Oxidation of carotenoids by free radicals: relationship between structure and reactivity. Biochim. Biophys. Acta 1997, 1336, 33–42.

Yao l, Iwai M, Furuta I. Correlation of bcl-2 and p53 expression with clinicopathological features in tongue sqamous cell carcinomas. Oral Oncol 1999, 35, 56–62.

Yla-Herttuala S, Palinski W, Rosenfeld M E, Parthasarathy S. et al. Evidence for the presence of oxidatively modified low-density lipoprotein in atherosclerotic lesions of rabbit and mice. J. Clin. Invest. 1989, 84, 1086–1095.

Ziegler R G, A view of the epidemiological evidence that carotenoids reduce the risk of cancer. J. Nutr. 1988, 119, 116–122.

What is claimed is:

1. A method of increasing a fraction of free carotenoids from a source of carotenoids in which at least some of the carotenoids are fatty acid esterified carotenoids, the method comprising the steps of
   (a) contacting the source of carotenoids with an effective amount of an esterase and a recycled emulsifier under conditions effective in deesterifying fatty acid esterified carotenoids, wherein said conditions effective in deesterifying the fatty acid esterified carotenoids are characterized by addition of at least one additive selected from the group consisting of:
   a cellulose degrading enzyme;
   a protein degrading enzyme;
   a pectin degrading enzyme; and
   at least one metal ion; and
   (b) extracting resulting deesterified carotenoids with ethyl acetate under alkaline conditions,
   thereby increasing the fraction of free carotenoids from the source of carotenoids.

2. The method of claim 1, wherein said emulsifier is a non-ester emulsifier.

3. The method of claim 1, wherein said emulsifier is lecithin.

4. The method of claim 1, wherein said emulsifier is deoxycholate.

5. The method of claim 1, wherein said emulsifier is a non-ionic detergent.

6. The method of claim 2, wherein said emulsifier is derived from bile, gum Arabic or salt of free fatty acids.

7. The method of claim 1, wherein said source of carotenoids is characterized in that a majority of the carotenoids in said source of carotenoids are said fatty acid esterified carotenoids.

8. The method of claim 1, wherein said source of carotenoids is red pepper.

9. The method of claim 1, wherein said source of carotenoids is red pepper powder.

10. The method of claim 1, wherein said source of carotenoids is paprika.

11. The method of claim 1, wherein said source of carotenoids is red pepper oil extract.

12. The method of claim 1, wherein said source of carotenoids is red pepper oleoresin.

13. The method of claim 1, wherein said source of carotenoids is selected from the group consisting of apple, apricot, avocado, blood orange, cape goosberry, carambola, chilli, clementine, kumquat, loquat, mango, minneola, nectarine, orange, papaya, peach, persimmon, plum, potato, pumpkin, tangerine and zucchini.

14. The method of claim 1, wherein said esterase is selected from the group consisting of a lipase, a carboxyl ester esterase and a chlorophylase.

15. The method of claim 1, wherein said esterase is a lipase.

16. The method of claim 15, wherein said lipase is selected from the group consisting of bacterial lipase, yeast lipase, mold lipase and animal lipase.

17. The method of claim 1, wherein said esterase is an immobilized lipase.

18. The method of claim 17, wherein said immobilized lipase is a recycled immobilized lipase.

19. The method of claim 1, wherein said at least one metal ion is selected from the group consisting of $Ca^{++}$ and $Na^+$.

20. The method of claim 1, wherein said addition of said at least one metal ion is by addition of at least one salt of said metal ion.

21. The method of claim 20, wherein said at least one salt is selected from the group consisting of $CaCl_2$ and NaCl.

22. The method of claim 1, wherein said cellulose degrading enzyme is selected from the group consisting of C1 type beta-1,4 glucanase, exo-beta-1,4 glucanase, endo-beta-1,4 glucanase and beta-glucosidase.

23. The method of claim 1, wherein said proteins degrading enzyme is selected from the group consisting of trypsin, papain, chymotrypsins, ficin, bromelin, cathepsins and rennin.

24. The method of claim 1, wherein said pectin degrading enzyme is selected from the group consisting of a pectin esterase, pectate lyase and a polygalacturonase.

25. The method of claim 1, wherein said alkaline conditions are characterized by pH from about 8.0 to about 10.

26. The method of claim 1, wherein said alkaline conditions are pH 9.5.

* * * * *